(12) United States Patent
Stevens et al.

(10) Patent No.: US 7,307,099 B2
(45) Date of Patent: Dec. 11, 2007

(54) 4-(1-(SULFONYL)-1H-INDOL-2-YL)-4-(HYDROXY)-CYCLOHEXA-2,5-DIENONE COMPOUNDS AND ANALOGS THEREOF AS THERAPEUTIC AGENTS

(75) Inventors: Malcolm Francis Graham Stevens, Nottingham (GB); Andrew David Westwell, Nottingham (GB); Tracey Dawn Poole, Nottingham (GB); Geoffrey Wells, Hull (GB); Jane Marie Berry, Walmer (GB)

(73) Assignee: Cancer Research Technology Limited, London (GB)

( * ) Notice: Subject to any disclaimer, the term of this patent is extended or adjusted under 35 U.S.C. 154(b) by 0 days.

(21) Appl. No.: 10/539,451

(22) PCT Filed: Dec. 20, 2002

(86) PCT No.: PCT/GB02/05842

§ 371 (c)(1),
(2), (4) Date: Jun. 20, 2005

(87) PCT Pub. No.: WO2004/056361

PCT Pub. Date: Jul. 8, 2004

(65) Prior Publication Data

US 2006/0100265 A1    May 11, 2006

(51) Int. Cl.
*A61K 31/404*    (2006.01)
*C07D 209/04*    (2006.01)
(52) U.S. Cl. .................................... 514/418; 548/509
(58) Field of Classification Search ................ 514/418; 548/509
See application file for complete search history.

(56) References Cited

U.S. PATENT DOCUMENTS

| 4,357,345 | A | 11/1982 | Moore |
| 4,535,165 | A | 8/1985 | Moore |
| 5,391,570 | A | 2/1995 | Catt et al. |
| 6,153,611 | A | 11/2000 | Mattson et al. |

FOREIGN PATENT DOCUMENTS

| EP | 0 469 984 A | 2/1992 |
| EP | 0 546 583 | 12/1992 |
| WO | WO 83/01775 | 5/1983 |
| WO | WO 01/92239 | 12/2001 |
| WO | 03 004479 A | 1/2003 |

OTHER PUBLICATIONS

Berry et al. "Quinols as Novel Therapeutic Agents. 2" J. Med. Chem. 2005, vol. 48, pp. 639-644.*
Wells et al. "Antitmour Benzothiazoles. Part 10: The Synthesis and Antitumour Activity of Benzothiazole Substituted Quinol Derivatives" Bioorganic & Medicinal Chemistry Letters, 2000, vol. 10, pp. 513-515.*

International Search Report of PCT/GB02/05842, mailed Apr. 2, 2003.
Alcaraz, L., et al., 1998, "Manumycin A: synthesis of the (+)-enantiomer and revision of stereochemical assignment," *J. Org. Chem.*, vol. 63, pp. 3526-3527.
Alley et al., 1988, "Feasibility of drug screening with panels of human tumor cell lines using a microculture tetrazolium assay," *Cancer Research*, vol. 48, p. 589.
Boyd, M.R., Paull, K.D., 1995, "Some practical considerations and applications of the National Cancer Institute in vitro anticancer drug discovery system," *Drug Dev. Res.*, vol. 34, pp. 91-104.
Callinan et al., 1990, "Spiro-annulated 2,5-cyclohexadienones via oxidation of 2'-alkenyl-p-phenyl phenols with iodobenzene diacetate," *Tetraderon Letters*, vol. 31, No. 32, pp. 4551-4552.
Capparelli et al., 1987, "Structural and solvent/electrolyte effects on the selectivity and efficiency of the anodic oxidation of para-substituted aromatic ethers. An efficient route to quinol ether ketals and quinol ethers," *J. Org. Chem.*, vol. 52, pp. 4953-4961.
Collins, L.; Franzblau, S.G.; 1997, "Microplate Alamar Blue Assay versus BACTEC 460 System for High-throughput Screening of Compounds against *Mycobacterium tuberculosis* and *Mycobacterium avium*," *Antimicrob. Agents Chemother.*, vol. 41, pp. 1004-1009.
Dengler et al., 1995, "Development of a propidium iodide fluorescence assay for proliferation and cytotoxicity assays," *Anti-cancer drugs*, vol. 6, pp. 522-532.
Dodge, J.A., et al., 1988, "Competitive dienone-phenol type rearrangements for the regioselective preparation of 2,4-disubstituted-naphth-1-ols," *Tetrahedron Letters*, vol. 29, No. 38, p. 4827-4830.

(Continued)

*Primary Examiner*—Kamal A. Saeed
*Assistant Examiner*—Joseph R. Kosack
(74) *Attorney, Agent, or Firm*—Nixon & Vanderhye P.C.

(57) ABSTRACT

This invention pertains to certain 4-(1-(sulfonyl)-1H-indol-2-yl)-4-(hydroxy)-cyclohexa-2,5-dienone compounds, and analogs thereof, including compounds of the following formula, which are, inter alia, antiproliferative agents, anticancer agents, and/or thioredoxin/thioredoxin reductase inhibitors: formula (I) wherein: Ar is a 1-(sulfonyl)-1H-indol-2-yl group; the bond marked α is independently: (a) a single bond; or: (b) a double bond; the bond marked β is independently: (a) a single bond; or: (b) a double bond; the group —$OR^Q$ is independently: (a) —OH; (b) an ether group (e.g., —OMe); or: (c) an acyloxy (i.e., reverse ester) group (e.g., —OC(=O)Me); each of $R^2$, $R^3$, $R^5$, and $R^6$, is independently a ring substituent and is: (a) H; (b) a monovalent monodentate substituent; or: (c) a ring substituent which, together with an adjacent ring substituent, and together with the ring atoms to which these ring substituents are attached, form a fused ring; and pharmaceutically acceptable salts, esters, amides, solvates, hydrates, and protected forms thereof. The present invention also pertains to pharmaceutical compositions comprising such compounds, and the use of such compounds and compositions, both in vitro and in vivo, for example, in the treatment of proliferative conditions, (e.g., cancer), and/or conditions mediated by thioredoxin/thioredoxin reductase.

52 Claims, No Drawings

OTHER PUBLICATIONS

Faaland et al., 1991, "Rapid uptake of tyrphostin into A431 human epidermoid cells is followed by delayed inhibition of epidermal growth factor (EGF) stimulated EFG receptor tyrosine kinase activity," *Mol. Cell Biol.*, vol. 11, pp. 2697-2703.

Gasdaska et al., 1994, "The predicted amino acid sequence of human thioredoxin is identical to that of the autocrine growth factor human adult T-cell derived cofactor (ADF): thioredoxin mRNA is elevated in some human tumors," *Biochimica et Biophysica Acta*, vol. 1218, p. 292.

Geran et al., 1972, "Protocols for screening chemical agents and natural products against tumor and other biological systems," *Cancer Chemother. Rep.*, vol. 3, p. 1-103.

Hutchinson et al., 2001, Antitumour benzothiazoles. 14. Synthesis and in vitro biological properties of fluroinated 2-(4-aminophenyl)benzothiazoles, *J. Med. Chem.*, vol. 44, pp. 1446-1455.

Kirkpatrick et al., 1999, "Parallel synthesis of disulfide inhibitors of the thioredoxin redox system as potential antitumor agents," *Anti-Cancer Drug Design*, vol. 14, pp. 421-432.

Kunkel et al., 1997, "Cell line-directed screening assay for inhibitors of thioredoxin reductase signaling as potential anti-cancer drugs," *Anti-Cancer Drug Design*, vol. 12, pp. 659-670.

McKillop et al., 1993, "A concise synthesis of the novel antibiotic aranorosin," *Tetrahedron Lett.*, vol. 34, pp. 5519-5522.

Milić, D. R., et al., "X-Ray crystal structure of 10β-hydroxy-4β,5β-epoxyestr-1-en-3, 17-dione and antitumor activity of its congeners," *Molecules*, vol. 4, pp. 338-352.

Oblong et al., 1993, "Purification of human thioreductase; properties and characterization by absorption and circular dichroism spectroscopy," *Biochemistry*, vol. 32, p. 7271.

Pelter, A., Elgendy, S.M.A., 1993, "Phenolic oxidations with phenyliodonium diacetate," *J. Chem. Soc., Perkin Trans. 1*, pp. 1891-1896.

Powis, G., Mustacich, D, Coon, A., 2000, "The role of the redox protein thioredoxin in cell growth and cancer," *Free Radical Biology & Medicine*, vol. 29, Nos. 3/4, pp. 312-322.

Ramdas et al., 1994, "The degree of inhibition of protein tyrosine kinase activity by Tyrphostin 23 and 25 is related to their instability," *Cancer Research*, vol. 54, pp. 867-869.

Reddy et al., 1992, "Inhibition of breast cancer cell growth in vitro by a tyrosine kinase inhibitor," *Cancer Research*, vol. 52, pp. 3631-3641.

Sonnenwirth, A.C., and Jarett, L. (eds.), Gradwohl's Clinical Laboratory Methods and Diagnosis, 8th edition, vol. 2, pp. 1707-1708.

Takeya, T., et al., 1999, "Total synthesis of (+/−)-plumbzaeylanone, a naphthoquinone trimer frum plumbago zeylandica," *Chemical and Pharmaceutical Bulletin*, vol. 47, No. 2, pp. 209-219.

Umezawa et al., 1991, "Use of erbstatin as protein tyrosine kinase inhibitor," *Methods Enzymol.*, vol. 201, pp. 379-385.

Wada, H., et al., 1987, "Chemical and chemotaxonomical studies of ferns. LXXIII. New flavonoids with modified B-ring from the genus *Pseudophegopteris* (*Thelypteridacae*)," *Chem. Pharm. Bull.*, vol. 35, pp. 4757-4762.

Weinstein, J. N., et al., 1997, "An information-intensive approach to the molecular pharmacology of cancer," *Science*, vol. 275, pp. 343-349.

Wells et al., Mar. 6, 2000, "Antitumour benzothiazoles. Part 10: The synthesis and antitumour activity of benzothiazole substituted quinol derivatives," *Bioorganic & Medicinal Chemistry Letters*, vol. 10, No. 5, pp. 513-515.

Wessely et al., 1952, "Uber die Einwirkung von metallorganischen Verbingungen auf Chinole I," *Monatsch. Chem.*, vol. 83, pp. 1253-1261.

Wipf, P., et al., "Synthesis of the antitumor antibiotic LL-C10037a," *J. Org. Chem.*, vol. 59, pp. 3518-3519.

De Costa et al, J. Chem. Soc. Perkin Trans. 1, 1992, pp. 1671-1680.

Fukushima et al, Yakugaku Zasshi, 1969, vol. 89, No. 9, pp. 1272-1275 (with English language abstract.

Noro et al, Yakugaku Zasshi, 1969, vol. 89, No. 6, pp. 851-856 (with English language Abstract).

Netherland (NL) Patent No. 6513784 dated Apr. 27, 1966 (with English language Abstract).

Nimz et al, Chemical Abstracts CA 93:222093.

Ershov et al, Chemical Abstracts CA 59:3192.

\* cited by examiner

4-(1-(SULFONYL)-1H-INDOL-2-YL)-4-(HYDROXY)-CYCLOHEXA-2,5-DIENONE COMPOUNDS AND ANALOGS THEREOF AS THERAPEUTIC AGENTS

This application is a 371 U.S. national phase of international application PCT/GB2002/005842, filed 20 Dec. 2002, which designated the U.S.; the entire content of which is incorporated herein by reference.

TECHNICAL FIELD

This invention pertains generally to the field of therapeutic agents, and more specifically to certain 4(1-(sulfonyl)-1H-indol-2-yl)4-(hydroxy)-cyclohexa-2,5-dienone compounds, and analogs thereof, which are, inter alia, antiproliferative agents, anticancer agents, and/or thioredoxin/thioredoxin reductase inhibitors. The present invention also pertains to compositions comprising such compounds, and the use of such compounds and compositions, both in vitro and in vivo, for example, in the treatment of proliferative conditions, cancer, and/or conditions mediated by thioredoxin/thioredoxin reductase.

BACKGROUND

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiments.

Phenolic xenobiotics can be modified by cellular systems in a number of ways, e.g., oxidation, glucuronidation, sulphation, methylation, acetylation, etc., and the instability of certain phenolic protein tyrosine kinase (PTK) inhibitors has been documented. For example, the antitumor PTK inhibitor erbstatin, shown below, is known to have a short half-life (<30 min) in fetal calf serum (see, e.g., Umezawa et al., 1991), and the lack of correlation between the activity of tyrphostins, shown below, against isolated enzymes and their effects in vitro and in vivo, is noteworthy (see, e.g., Rambas et al., 1994). Di- and tri-phenolic tyrphostins decompose in solution to more active PTK inhibitors (see, e.g., Faaland et al., 1991), whereas tyrphostins devoid of hydroxy groups have a rapid onset of cellular activity (see, e.g., Reddy et al., 1992), implicating metabolic oxidation to a quinone (or other) moiety as a possible bioactivating step.

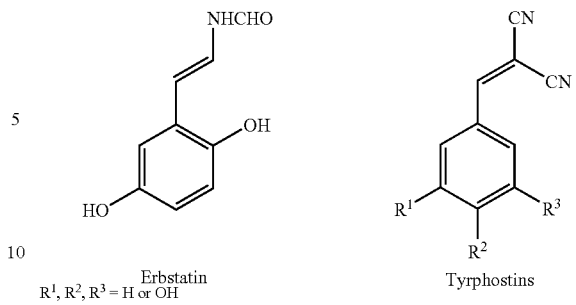

Erbstatin
$R^1, R^2, R^3$ = H or OH

Tyrphostins

Wells et al., 2000, describe several benzothiazole substituted quinol derivatives, shown below, where $R^1$ is —Ac, -Me, -Et, -nPr, or —CH$_2$C≡CH, and $R^2$ is -Me or -Et. These compounds were reported to have activity against certain colon (HCT-116 and HT29) and breast (MCF-7 and MDA468) cancer cell lines in vitro. Note that there is no mention of possible application as thioredoxin/thioredoxin reductase inhibitors.

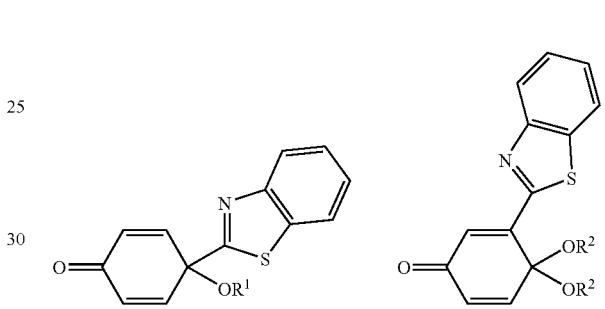

Stevens et al., 2003, describe various 4-aryl quinols and analogs thereof, including 4-(1H-indol-2-yl)quinols (see page 20 therein), wherein the 1H-indol-2-yl group bears an optional N-substituent (i.e., 1-substituent), denoted $R^N$, which is —H. $C_{1-7}$alkyl, $C_{3-20}$heterocyclyl, or $C_{5-20}$aryl (see page 22 therein). Nowhere in this document is there any teaching or suggestion of a 1-sulfonyl substituent on the 1H-indol-2-yl group (e.g., as $R^N$).

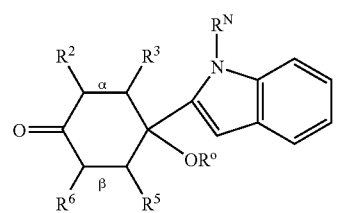

Two compounds that contain a hydroxycyclohexadienone structure and which apparently have antitumor activity have been reported: a hydroxylated flavone-substituted quinol (i.e., a chromone substituted quinol) (see, e.g., Wada et al., 1987) and an oxidized estrone (see, e.g., Milic et al., 1999).

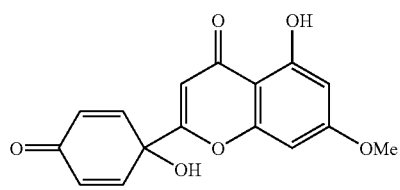

-continued

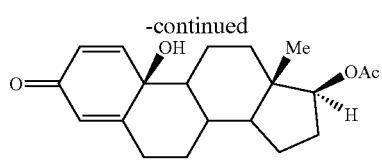

Several related antitumor epoxyquinols, such as Manumycin A (see, e.g., Alcaraz et al., 1998) and LL-C 10037α (see, e.g., Wipf et al., 1994) are known.

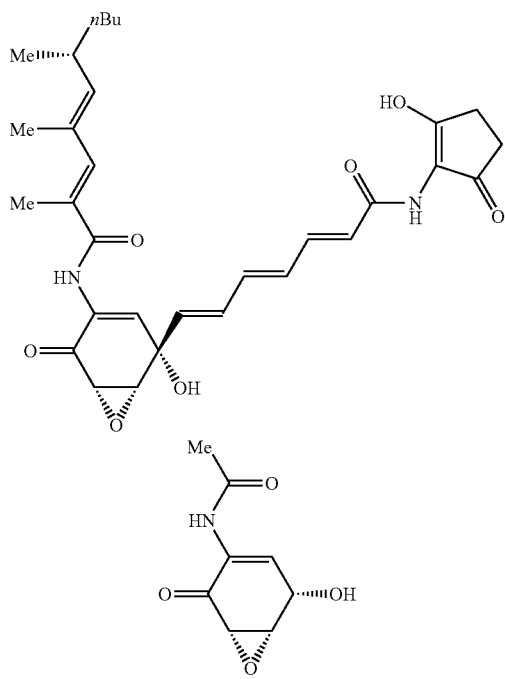

SUMMARY OF THE INVENTION

One aspect of the invention pertains to novel active compounds as described herein.

Another aspect of the invention pertains to a composition comprising an active compound as described herein and a pharmaceutically acceptable carrier or diluent.

Another aspect of the invention pertains to an active compound as described herein for use in a method of treatment of the human or animal body.

Another aspect of the invention pertains to use of an active compound as described herein for the manufacture of a medicament for use in the treatment of, for example, a proliferative condition (e.g., cancer), a condition mediated by thioredoxin/thioredoxin reductase, etc.

Another aspect of the invention pertains to a method of inhibiting thioredoxin/thioredoxin reductase, in vitro or in vivo, comprising contacting a cell with an effective amount of an active compound as described herein.

Another aspect of the invention pertains to a method of regulating cell proliferation, in vitro or in vivo, comprising contacting a cell with an effective amount of an active compound as described herein.

Another aspect of the invention pertains to a method of (a) inhibiting cell proliferation; (b) inhibiting cell cycle progression; (c) promoting apoptosis; or (d) a combination of one or more of these, in vitro or in vivo, comprising contacting a cell with an effective amount of a compound as described herein.

Another aspect of the invention pertains to a method for the treatment of, for example, a proliferative condition (e.g., cancer), a condition mediated by thioredoxin/thioredoxin reductase, etc., comprising administering to a subject suffering from said condition a therapeutically-effective amount of an active compound, as described herein.

Another aspect of the present invention pertains to a kit comprising (a) the active compound, preferably provided as a pharmaceutical composition and in a suitable container and/or with suitable packaging; and (b) instructions for use, for example, written instructions on how to administer the active compound.

Another aspect of the present invention pertains to compounds obtainable by a method of synthesis as described herein, or a method comprising a method of synthesis as described herein.

Another aspect of the present invention pertains to compounds obtained by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

As will be appreciated by one of skill in the art, features and preferred embodiments of one aspect of the invention will also pertain to other aspect of the invention.

DETAILED DESCRIPTION OF THE INVENTION

Compounds

One aspect of the present invention pertains compounds having the following formula:

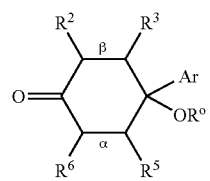

(1)

wherein:
Ar is a 1-(sulfonyl)-1H-indol-2-yl group;
the bond marked α is independently:
  (a) a single bond; or:
  (b) a double bond;
the bond marked β is independently:
  (a) a single bond; or:
  (b) a double bond;
the group —OR$^O$ is independently:
  (a) —OH;
  (b) an ether group (e.g., —OMe); or:
  (c) an acyloxy (i.e., reverse ester) group (e.g., —OC(=O)Me);
each of R$^2$, R$^3$, R$^5$, and R$^6$, is independently a ring substituent and is:
  (a) H;
  (b) a monovalent monodentate substituent; or:

(c) a ring substituent which, together with an adjacent ring substituent, and together with the ring atoms to which these ring substituents are attached, form a fused ring;

and pharmaceutically acceptable salts, esters, amides, solvates, hydrates, and protected forms thereof.

Optical Isomers

Note that, in these compounds, one, two, or three of the ring atoms (marked with an asterisk (*) in the following formula) may be chiral (for example, depending on the bonds α and β, and the substituents, $R^2$, $R^3$, $R^5$ and $R^6$) and if so, may be in R or S configuration. Unless otherwise specified, the resulting optical isomers (discussed below) are encompassed by the corresponding structure, which is silent as to configuration.

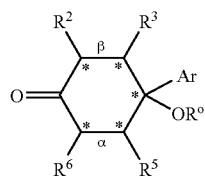

The Bonds, α and β

The bond marked α is independently a single bond or a double bond.

The bond marked β is independently a single bond or a double bond.

In one embodiment:

(a) α is independently a double bond and β is independently a double bond; or:

(b) α is independently a single bond and β is independently a single bond.

In one embodiment, α is independently a double bond and β is independently a double bond (and the compound is substituted cyclohexa-2,5-dienone):

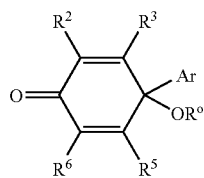

(2)

In one embodiment, α is independently a single bond and β is independently a single bond (and the compound is substituted cyclohexan-2-one):

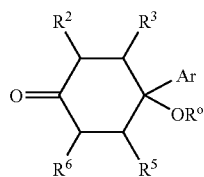

(3)

In one embodiment, α is independently a single bond and β is independently a double bond (and the compound is substituted cyclohex-2-enone):

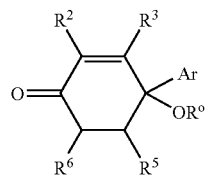

(4)

Note that, in the context of α and β, a "double" bond includes both a simple double bond, such as the double bond in cyclohexene, and an aromatic "double" bond, such as, for example, the carbon-carbon bonds in benzene.

Quinol Ring Substituents, $R^2$, $R^3$, $R^5$, and $R^6$

The ring substituents, $R^2$, $R^3$, $R^5$, and $R^6$, may be selected to improve the physical or biological properties of the compound, for example, to improve water solubility and/or bioavailability.

In one embodiment, each of $R^2$, $R^3$, $R^5$, and $R^6$, is independently a ring substituent and is:

(a) H;

or:

(b) a monovalent monodentate substituent (for example, as described below under the heading "Quinol Ring Substituents: Monovalent Monodentate Substituents");

or:

(c) a ring substituent which, together with an adjacent ring substituent, and together with the ring atoms to which these ring substituents are attached, form a fused ring (for example, as described below under the heading "Quinol Ring Substituents: Fused Rings").

Quinol Ring Substituents: Monovalent Monodentate Substituents

In one embodiment, said monovalent monodentate substituent (e.g., mentioned above in reference to $R^2$, $R^3$, $R^5$, and $R^6$) is independently as defined below for $R^P$, or a thiol or thioether group (for example, as described below under the heading "Quinol Ring Substituents: Thiols and Thioethers").

In one embodiment, said monovalent monodentate substituent is independently selected from:

hydroxy (—OH);

halo;

azido;

$C_{1-7}$alkyl, including, e.g., halo-$C_{1-7}$alkyl;

amino-$C_{1-7}$alkyl (e.g., —$(CH_2)_w$-amino);

carboxy-$C_{1-7}$alkyl (e.g., —$(CH_2)_w$—COOH);

hydroxy-$C_{1-7}$alkyl (e.g., —$(CH_2)_w$—OH);

$C_{5-20}$aryl-$C_{1-7}$alkyl;

ether, including, e.g., $C_{1-7}$alkoxy;

halo-$C_{1-7}$alkoxy;

amino-$C_{1-7}$alkoxy (e.g., —$O(CH_2)_w$-amino);

carboxy-$C_{1-7}$alkoxy (e.g., —$O(CH_2)_w$—COOH);

hydroxy-$C_{1-7}$alkoxy (e.g., —$O(CH_2)_w$—OH);

$C_{5-20}$aryl-$C_{1-7}$alkoxy;

acyl, including, e.g., $C_{1-7}$alkyl-acyl;

halo-$C_{1-7}$alkyl-acyl;

amino-$C_{1-7}$alkyl-acyl (e.g., —C(=O)$(CH_2)_w$-amino);

carboxy-$C_{1-7}$alkyl-acyl (e.g., —C(=O)$(CH_2)_w$—COOH);

hydroxy-$C_{1-7}$alkyl-acyl (e.g., —C(=O)$(CH_2)_w$—OH);

$C_{5-20}$aryl-$C_{1-7}$alkyl-acyl;
$C_{5-20}$aryl-acyl; and
thiol (—SH);
thioether;
wherein w is an integer from 1 to 7, preferably 1 to 4, preferably 1, 2, or 3.

In one embodiment, said monovalent monodentate substituent is independently selected from:
—OH;
—F, —Cl, —Br, —I;
—$N_3$;
-Me, -Et, -nPr, -iPr, -tBu;
—OMe, —OEt, —O-nPr, —O-iPr, —O-tBu;
—C(=O)Me, —C(=O)Et, —C(=O)nPr, —C(=O)iPr, —C(=O)tBu, —C(=O)Ph, —C(=O)Bn;
—SH;
—SMe, —SEt, —SnPr, —S-iPr, —S-nBu, —S-iBu, —S-sBu, —S-tBu, —S—$CH_2$-Ph, —S-Ph;
a thioether group derived from cysteine, homocysteine, glutathione, or a peptide of the type -Cys-$(X)_y$-Cys-, where X is an amino acid, and y is an integer from 1 to 6.

In one embodiment, said monovalent monodentate substituent is independently selected from: hydroxy, halo, $C_{1-7}$alkoxy, thiol, and thioether.

In one embodiment, said monovalent monodentate substituent is independently selected from:
—OH;
—F, —Cl, —Br, —I;
—OMe, —OEt, —O-nPr, —O-iPr, —O-tBu;
—SH;
—SMe, —SEt, —SnPr, —S-iPr, —S-nBu, —S-iBu, —S-sBu, —S-tBu, —S—$CH_2$-Ph, —S-Ph;
a thioether group derived from cysteine, homocysteine, glutathione, or a peptide of the type -Cys-$(X)_y$-Cys-, where X is an amino acid, and y is an integer from 1 to 6.

In one embodiment, said monovalent monodentate substituent is independently selected from: halo, thiol, and thioether.

In one embodiment, said monovalent monodentate substituent is independently selected from:
—F, —Cl, —Br, —I;
—SH;
—SMe, —SEt, —SnPr, —S-iPr, —S-nBu, —S-iBu, —S-sBu, —S-tBu, —S—$CH_2$-Ph, —S-Ph;
a thioether group derived from cysteine, homocysteine, glutathione, or a peptide of the type -Cys-$(X)_y$-Cys-, where X is an amino acid, and y is an integer from 1 to 6.

Quinol Ring Substituents: Thiols and Thioethers

In one embodiment, one or more of said monovalent monodentate substituent(s), $R^2$, $R^3$, $R^5$, and $R^6$, is a thiol (—SH) or a thioether group.

In one embodiment, if: α is a double bond and β is a double bond; then: thiols and thioethers are excluded from the alternatives for said monovalent monodentate substituents, $R^2$, $R^3$, $R^5$, and $R^6$.

In one embodiment, one or both of $R^3$ and $R^5$, is a thiol or thioether group.

In one embodiment, exactly one of $R^3$ and $R^5$, is a thiol or thioether group.

In one embodiment, each of $R^3$ and $R^5$ is a thiol or thioether group.

In one embodiment, if: one or both of $R^3$ and $R^5$ is a thiol or thioether group; then: α is a single bond; and β is a single bond.

In one embodiment, if: $R^3$ is a thiol or thioether group; then: β is a single bond.

In one embodiment, if: $R^5$ is a thiol or thioether group; then: α is a single bond.

In one embodiment, if: each of $R^3$ and $R^5$ is a thiol or thioether group; then: α is a single bond; and β is a single bond.

In one embodiment, α is a single bond, β is a single bond, and: one or more of said monovalent monodentate substituent, $R^2$, $R^3$, $R^5$, and $R^6$, is a thiol or a thioether group.

In one embodiment, α is a single bond, β is a single bond, and: one or both of $R^3$ and $R^5$ is a thiol or thioether group.

In one embodiment, α is a single bond, β is a single bond, and: exactly one of $R^3$ and $R^5$ is a thiol or thioether group.

In one embodiment, α is a single bond, β is a single bond, and: each of $R^3$ and $R^5$ is a thiol or thioether group.

In one embodiment, α is a single bond, β is a single bond, and: each of $R^3$ and $R^5$ is a thioether group, and: $R^3$ and $R^5$ are linked. For example, $R^3$ and $R^5$ may, together, form a part of a peptide comprising the sequence -Cys-$(X)_y$-Cys-, where X is an amino acid (e.g., α-amino acid), and y is an integer from 1 to 6 (e.g., 1, 2, 3, 4, 5, or 6), and the —SH groups of the two cysteine residues are attached to the cyclohexa-2,5-dienone ring.

Such compounds may be considered to be mono- and di-thiol adducts of the corresponding cyclohex-2,5-dienone (see below).

In such cases, the thiol and thioether group may collectively be denoted —$SR^S$.

In one embodiment, $R^S$ is —H or an organic group (typically from 1 to 30 atoms other than hydrogen) which optionally bears one or more substituents, such as hydroxy, carboxy, carboxylate, acyloxy, amino, amido, and acyl amido groups.

In one embodiment:
(a) $R^S$ is —H, $C_{1-7}$alkyl (including, e.g., $C_{5-20}$aryl-$C_{1-7}$alkyl), $C_{3-20}$heterocyclyl, or $C_{5-20}$aryl; and is optionally substituted; or
(b) —$SR^S$ is a thioether group derived from a thiol-containing amino acid or peptide.

In one embodiment:
(a) $R^S$ is —H, $C_{1-7}$alkyl (including, e.g., $C_{5-20}$aryl-$C_{1-7}$alkyl) or $C_{5-20}$aryl; and is optionally substituted; or
(b) —$SR^S$ is a thioether group derived from a thiol-containing amino acid or peptide.

In one embodiment:
(a) $R^S$ is —H, $C_{1-7}$alkyl (including, e.g., $C_{5-20}$aryl-$C_{1-7}$alkyl) or $C_{5-20}$aryl; and is optionally substituted.

In one embodiment:
(b) —$SR^S$ is a thioether group derived from a thiol-containing amino acid or peptide.

In one embodiment, —$SR^S$ is a thioether group derived from a thiol-containing compound, such as, for example, a thiol-containing amino acid, e.g., cysteine, homocysteine, etc., or a thiol-containing peptide, e.g., a peptide comprising a thiol-containing amino acid, for example, glutathione and peptides (e.g., comprising from 4 to 100, preferably from 4 to 20, more preferably 4 to 10, amino acids) comprising the sequence -Cys-$(X)_y$-Cys-, where X is an amino acid (e.g., α-amino acid), and y is an integer from 1 to 6 (e.g., 1, 2, 3, 4, 5, or 6); as well as and esters (e.g., methyl esters) and amides (e.g., acetic acid amides) thereof.

Some examples of such groups are shown below (where n is e.g., 1, 2, or 3):

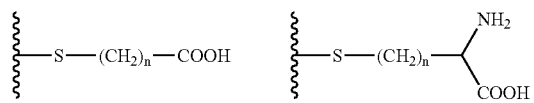

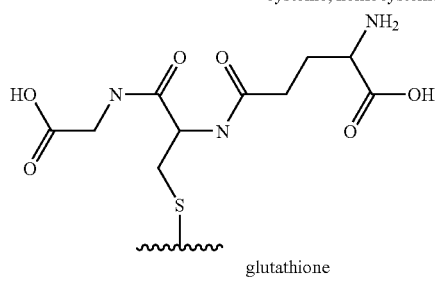

cysteine, homocysteine, etc.

glutathione

In one embodiment:

(a) $R^S$ is selected from: —H, -Me, -Et, -nPr, -iPr, -nBu, -iBu, -sBu, -tBu, —CH$_2$-Ph, -Ph; or:

(b) —SR$^S$ is a thioether group derived from cysteine, homocysteine, glutathione, or a peptide comprising the sequence -Cys-(X)$_y$-Cys-, where X is an amino acid, and y is an integer from 1 to 6.

The cyclohexa-2,5-dienone compounds described herein undergo addition reactions with thiols, to yield thiol mono- and/or di-adducts (see "Synthesis" below). Without wishing to be bound by any particular theory, it is believed that the addition reaction is reversible, and that such adducts may undergo elimination reaction, e.g., in vivo, to yield the original cyclohexa-2,5-dienone compound. In this way, the thiol mono- and/or di-adducts may act as prodrugs for the corresponding cyclohexa-2,5-dienone compounds; the thiol mono- and/or di-adducts may also have improved properties, e.g., water solubility, as compared to the corresponding cyclohexa-2,5-dienone compounds.

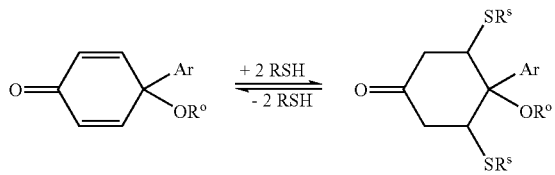

Quinol Ring Substituents: No Fused Rings

In one embodiment, each of $R^2$, $R^3$, $R^5$, and $R^6$, is independently a ring substituent and is:

(a) H;

or:

(b) a monovalent monodentate substituent (for example, as described below under the heading "Quinol Ring Substituents: Monovalent Monodentate Substituents").

In one embodiment, $R^5$ and $R^6$ are —H; and α, β, $R^2$, $R^3$, Ar, and $R^O$ are as defined herein, but $R^2$ and $R^3$ do not also form a fused ring:

(5)

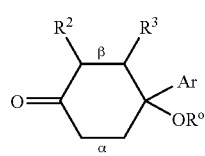

In one embodiment, $R^2$ and $R^3$ are —H; and α, β, $R^5$, $R^6$, Ar, and $R^O$ are as defined herein, but $R^5$ and $R^6$ do not also form a fused ring:

(6)

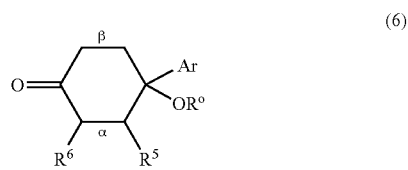

In one embodiment, $R^2$ and $R^6$ are —H; and α, β, $R^3$, $R^5$, Ar, and $R^O$ are as defined herein:

(7)

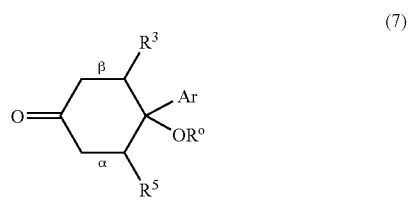

In one embodiment, $R^3$ and $R^5$ are —H; and α, β, $R^2$, $R^6$, Ar, and $R^O$ are as defined herein:

(8)

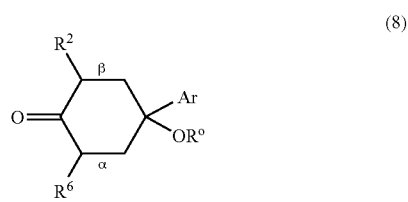

In one embodiment, $R^2$, $R^3$, $R^5$ and $R^6$ are —H; and α, β, Ar, and $R^O$ are as defined herein:

(9)

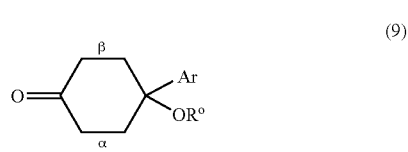

In one embodiment, $R^2$, $R^3$, $R^5$ and $R^6$ are —H; α is a double bond; β is a double bond; and Ar and $R^O$ are as defined herein:

(11)

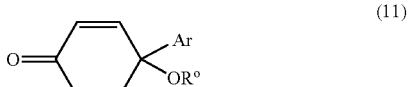

In one embodiment, $R^2$, $R^3$, $R^5$ and $R^6$ are —H; α is a single bond; β is a single bond; and Ar and $R^O$ are as defined herein:

(12)

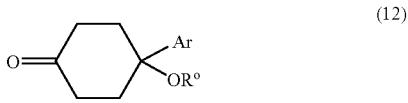

In one embodiment, $R^2$, $R^3$, $R^5$ and $R^6$ are —H; α is a single bond; β is a double bond; and Ar and $R^O$ are as defined herein:

(13)

Ring Substituents: Fused Rings

In one embodiment, one or more ring substituents (e.g., $R^3$, $R^4$, $R^5$, or $R^6$), together with an adjacent ring substituent (i.e., selected from the remainder of $R^3$, $R^4$, $R^5$, and $R^6$), and together with the ring atoms to which these ring substituents are attached, form a fused ring (fused to the main ring).

In one embodiment, (a) $R^2$ and $R^3$, together with the ring atoms to which they are attached, form a fused ring;

(b) $R^5$ and $R^6$, together with the ring atoms to which they are attached, form a fused ring; or:

(c) or both (a) and (b).

In one embodiment, the fused ring (or, if there are two fused rings, one of them, or each of them) is a fused aromatic ring.

In one embodiment, the fused ring (or, if there are two fused rings, one of them, or each of them) is a fused aromatic ring with 5 or 6 ring atoms.

In one embodiment, the fused ring (or, if there are two fused rings, one of them, or each of them) is a fused aromatic ring with 6 ring atoms.

In one embodiment, the fused ring (or, if there are two fused rings, one of them, or each of them) is a fused aromatic ring with 6 ring carbon atoms.

Where ring substituents, together with the ring atoms to which they are attached, form an aromatic ring (fused to the main ring), that ring may itself be substituted with one or more aryl substituents, for example, as defined for $R^P$.

In one embodiment, $R^2$ and $R^3$, together with the ring atoms to which they are attached, form a fused ring, as described above (e.g., a fused aromatic ring; a fused aromatic ring with 5 or 6 ring atoms; a fused aromatic ring with 6 ring atoms; a fused aromatic ring with 6 ring carbon atoms).

In one embodiment, $R^2$ and $R^3$ form a fused benzene ring; β is a double bond; and α, Ar, $R^O$, $R^5$, and $R^6$ are as defined herein:

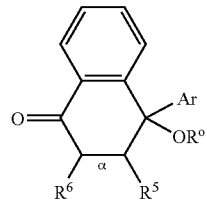
(14)

In a further embodiment, $R^5$ and $R^6$ do not also form a fused ring.

In one embodiment, $R^2$ and $R^3$ form a fused benzene ring; β is a double bond; $R^5$ is —H; and α, $R^6$, Ar, and $R^O$ are as defined herein:

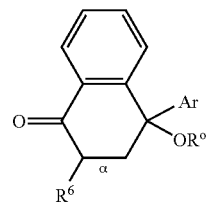
(15)

In one embodiment, $R^2$ and $R^3$ form a fused benzene ring; β is a double bond; $R^6$ is —H; and α, $R^5$, Ar, and $R^O$ are as defined herein:

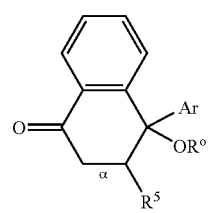
(16)

In one embodiment, $R^2$ and $R^3$ form a fused benzene ring; β is a double bond; $R^5$ and $R^6$ are —H; and α, Ar, and $R^O$ are as defined herein:

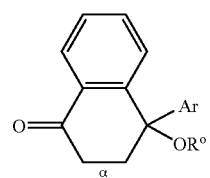
(17)

In one embodiment, $R^2$ and $R^3$ form a fused benzene ring; β is a double bond; $R^5$ and $R^6$ are —H; α is a double bond; and Ar and $R^O$ are as defined herein:

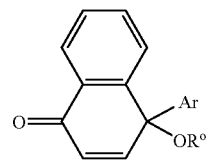
(18)

In one embodiment, $R^5$ and $R^6$, together with the ring atoms to which they are attached, form a fused ring, as described above (e.g., a fused aromatic ring; a fused aromatic ring with 5 or 6 ring atoms; a fused aromatic ring with 6 ring atoms; a fused aromatic ring with 6 ring carbon atoms).

In one embodiment, $R^5$ and $R^6$ form a fused benzene ring; α is a double bond; and β, $R^2$, $R^3$, Ar, and $R^O$ are as defined herein:

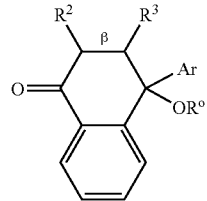
(19)

In a further embodiment, $R^2$ and $R^3$ do not also form a fused ring.

In one embodiment, $R^5$ and $R^6$ form a fused benzene ring; α is a double bond; $R^3$ is —H; and β, $R^2$, Ar, and $R^O$ are as defined herein:

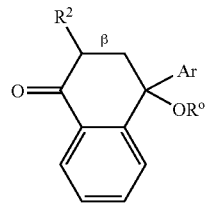
(20)

In one embodiment, $R^5$ and $R^6$ form a fused benzene ring; α is a double bond; $R^2$ is —H; and β, $R^3$, Ar, and $R^O$ are as defined herein:

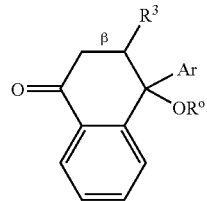
(21)

Oxy Subsitutents, $R^O$

The oxy substituent, $R^O$, is independently: (a) —H; or: (b) other than —H.

In one embodiment, the group —$OR^O$ is independently:
(a) —OH;
(b) an ether group (e.g., —OMe); or
(c) an acyloxy (i.e., reverse ester) group (e.g., —OC(=O)Me);

In one embodiment, $R^O$ is independently:
(a) —H;
(b) $C_{1-7}$alkyl, $C_{3-20}$heterocyclyl, or $C_{5-20}$aryl; and is optionally substituted; or
(c) $C_{1-7}$alkyl-acyl, $C_{3-20}$heterocyclyl-acyl, or $C_{5-20}$aryl-acyl; and is optionally substituted.

In one embodiment, $R^O$ is unsubstituted.
In one embodiment, $R^O$ is substituted.

Oxy Subsitutent, $R^O$, is —H

In one embodiment, $R^O$ is independently —H.

In one embodiment, $R^O$ is —H; and $R^2$, $R^3$, $R^5$, $R^6$, α, β, and Ar are as defined herein:

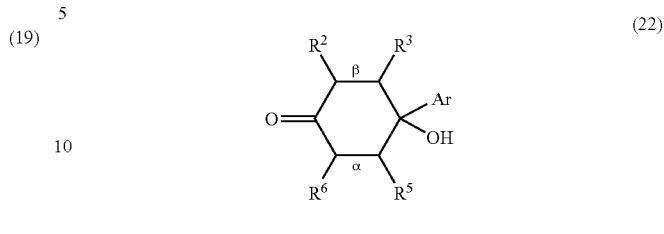
(22)

In one embodiment, $R^O$ is —H; α is a double bond; β is a double bond; and $R^2$, $R^3$, $R^5$, $R^6$, and Ar are as defined herein:

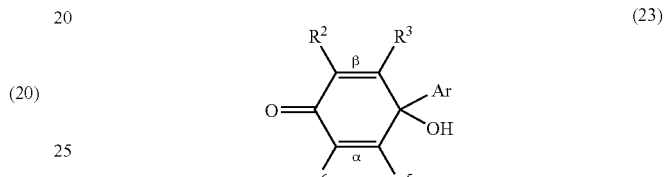
(23)

In one embodiment, $R^O$ is —H; α is a single bond; β is a single bond; and $R^2$, $R^3$, $R^5$, $R^6$, and Ar are as defined herein:

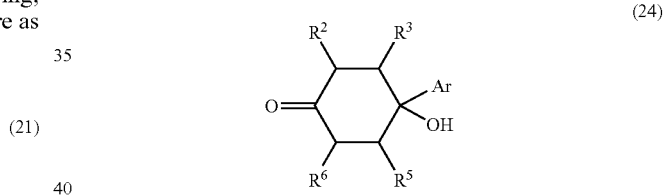
(24)

In one embodiment, $R^O$ is —H; α is a single bond; β is a double bond; and $R^2$, $R^3$, $R^5$, $R^6$, and Ar are as defined herein:

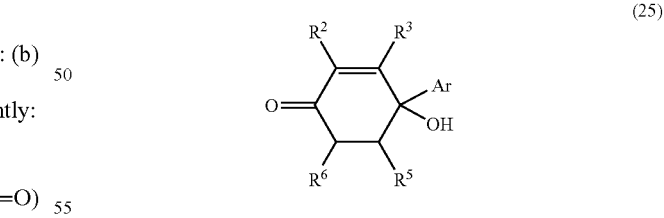
(25)

In one embodiment, $R^O$ is —H; $R^2$, $R^3$, $R^5$ and $R^6$ are —H; α is a double bond; β is a double bond; and Ar is as defined herein:

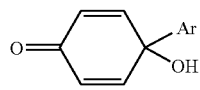
(26)

In one embodiment, $R^O$ is —H; $R^2$, $R^3$, $R^5$ and $R^6$ are —H; α is a single bond; β is a single bond; and Ar is as defined herein:

 (27)

In one embodiment, $R^O$ is —H; $R^2$, $R^3$, $R^5$ and $R^6$ are —H; α is a single bond; β is a double bond; and Ar is as defined herein:

 (28)

In one embodiment, $R^O$ is —H; $R^2$ and $R^3$ form a fused benzene ring; $R^5$ and $R^6$ are —H; α is a double bond; β is a double bond; and Ar is as defined herein:

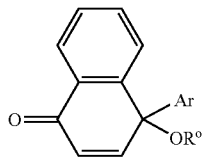 (29)

Oxy Substituent, $R^O$, is Other Than —H

In one embodiment, $R^O$ is independently other than —H.

Without wishing to be bound by any particular theory, it is believed that the group —$OR^O$ is converted (e.g., hydrolyzed, metabolized, etc.) to give the group —OH, in vivo. Consequently, in one embodiment, the group —$OR^O$ is selected to be readily hydrolyzed in vivo.

In one embodiment, the group —$OR^O$ is independently:
(b) an ether group; or
(c) an acyloxy (i.e., reverse ester) group.

In one embodiment, the group —$OR^O$ is independently (b).

In one embodiment, the group —$OR^O$ is independently (c).

In one embodiment, $R^O$ is independently:
(b) $C_{1-7}$alkyl, $C_{3-20}$heterocyclyl, or $C_{5-20}$aryl; and is optionally substituted;
(c) $C_{1-7}$alkyl-acyl, $C_{3-20}$heterocyclyl-acyl, or $C_{5-20}$aryl-acyl; and is optionally substituted.

In one embodiment, the group —$OR^O$ is independently (b).

In one embodiment, the group —$OR^O$ is independently (c).

In one embodiment, $R^O$ is unsubstituted.

In one embodiment, $R^O$ is substituted.

In one embodiment, $R^O$ is optionally substituted with one or more of the following groups:
hydroxy (—OH);
halo;
carboxy (—COOH);
amino; and,
$C_{5-20}$aryl.

In one embodiment, $R^O$ is an amino-$C_{1-7}$alkyl-acyl group, of the formula —C(=O)-J-K, wherein J is a $C_{1-7}$alkylene group, and K is an amino group. In one embodiment, $R^O$ is —C(=O)(CH$_2$)$_n$—K, where n is an integer from 1 to 7, preferably 1 to 3, and K is an amino group. For example, in one embodiment, $R^O$ is —C(=O)CH$_2$CH$_2$CH$_2$NH$_2$.

The Aryl Group, Ar

The aryl group, Ar, is a 1-(sulfonyl)-1H-indol-2-yl group.

In one embodiment, Ar is a group of the following formula:

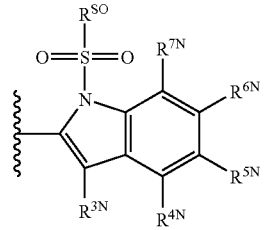

wherein:
$R^{SO}$ is independently a sulfonyl substituent; and
each of $R^{3N}$, $R^{4N}$, $R^{5N}$, $R^{6N}$, and $R^{7N}$ is independently an indolyl subsitutent.

The Sulfonyl Substituent, $R^{SO}$

In one embodiment, the sulfonyl substituent, $R^{SO}$, is $C_{1-7}$alkyl, $C_{3-20}$heterocyclyl, or $C_{5-20}$aryl; and is optionally substituted.

In one embodiment, $R^{SO}$ is $C_{1-7}$alkyl or $C_{5-20}$aryl; and is optionally substituted.

In one embodiment, $R^{SO}$ is $C_{1-7}$alkyl; and is optionally substituted.

In one embodiment, $R^{SO}$ is $C_{3-20}$heterocyclyl; and is optionally substituted.

In one embodiment, $R^{SO}$ is $C_{5-20}$aryl; and is optionally substituted.

In one embodiment, $R^{SO}$ is unsubstituted.

In one embodiment, $R^{SO}$ is substituted.

Examples of substituents are described below, for example, as defined for $R^P$.

The Sulfonyl Substituent, $R^{SO}$: Alkyl Sulfonyl

In one embodiment, $R^{SO}$ is $C_{1-7}$alkyl; and is optionally substituted.

In one embodiment, $R^{SO}$ is $C_{1-6}$alkyl; and is optionally substituted.

In one embodiment, $R^{SO}$ is $C_{1-5}$alkyl; and is optionally substituted.

In one embodiment, $R^{SO}$ is $C_{1-4}$alkyl; and is optionally substituted.

In one embodiment, $R^{SO}$ is $C_{1-3}$alkyl; and is optionally substituted.

In one embodiment, $R^{SO}$ is methyl or ethyl; and is optionally substituted.

In one embodiment, $R^{SO}$ is methyl; and is optionally substituted.

In one embodiment, $R^{SO}$ is substituted.

In one embodiment, $R^{SO}$ is unsubstituted.

Examples of substituents are described below, for example, as defined for $R^P$.

When $R^{SO}$ is -Me, the sulfonyl group, —SO$_2$R$^{SO}$, is "mesyl."

When $R^{SO}$ is —$CF_3$, the sulfonyl group, —$SO_2R^{SO}$, is "triflyl."

When $R^{SO}$ is -Et, the sulfonyl group, —$SO_2R^{SO}$, is "esyl."

When $R^{SO}$ is —$C_4F_9$, the sulfonyl group, —$SO_2R^{SO}$, is "nonaflyl."

When $R^{SO}$ is —$CH_2CF_3$, the sulfonyl group, —$SO_2R^{SO}$, is "tresyl."

The Sulfonyl Substituent, $R^{SO}$: Alkyl Sulfonyl: Substituents

In one embodiment, $R^{SO}$ is $C_{1-7}$alkyl (or as defined above), optionally substituted with one more substituents as defined for $R^P$.

In one embodiment, $R^{SO}$ is $C_{1-7}$alkyl (or as defined above), optionally substituted with one more of the following groups:
hydroxy (—OH);
halo;
carboxy (—COOH);
amino; and,
$C_{5-20}$aryl.

In one embodiment, $R^{SO}$ is selected from:
hydroxy-$C_{1-7}$alkyl (e.g., —$(CH_2)_w$—OH);
halo-$C_{1-7}$alkyl;
carboxy-$C_{1-7}$alkyl (e.g., —$(CH_2)_w$—COOH);
amino-$C_{1-7}$alkyl (e.g., —$(CH_2)_w$-amino); and,
$C_{5-20}$aryl-$C_{1-7}$alkyl;
wherein w is an integer from 1 to 7, preferably 1 to 4, preferably 1, 2, or 3.

The Sulfonyl Substituent, $R^{SO}$: Heterocyclyl Sulfonyl

In one embodiment, $R^{SO}$ is $C_{3-20}$heterocyclyl; and is optionally substituted.

In one embodiment, $R^{SO}$ is $C_{5-20}$heterocyclyl; and is optionally substituted.

In one embodiment, $R^{SO}$ is $C_{5-15}$heterocyclyl; and is optionally substituted.

In one embodiment, $R^{SO}$ is $C_{5-12}$heterocyclyl; and is optionally substituted.

In one embodiment, $R^{SO}$ is $C_{5-10}$heterocyclyl; and is optionally substituted.

In one embodiment, $R^{SO}$ is $C_{5-9}$heterocyclyl; and is optionally substituted.

In one embodiment, $R^{SO}$ is $C_{5-7}$heterocyclyl; and is optionally substituted.

In one embodiment, $R^{SO}$ is $C_{5-6}$heterocyclyl; and is optionally substituted.

In one embodiment, $R^{SO}$ is substituted.
In one embodiment, $R^{SO}$ is unsubstituted.
Examples of substituents are described below, for example, as defined for $R^P$.

The Sulfonyl Substituent, $R^{SO}$: Aryl Sulfonyl

In one embodiment, $R^{SO}$ is $C_{5-20}$aryl; and is optionally substituted.

In one embodiment, $R^{SO}$ is $C_{5-20}$carboaryl; and is optionally substituted.

In one embodiment, $R^{SO}$ is $C_{5-10}$aryl; and is optionally substituted.

In one embodiment, $R^{SO}$ is $C_{5-10}$carboryl; and is optionally substituted.

In one embodiment, $R^{SO}$ is naphthyl or phenyl; and is optionally substituted.

In one embodiment, $R^{SO}$ is naphthyl; and is optionally substituted.

In one embodiment, $R^{SO}$ is $C_{5-6}$aryl; and is optionally substituted.

In one embodiment, $R^{SO}$ is $C_{5-6}$carboaryl; and is optionally substituted.

In one embodiment, $R^{SO}$ is phenyl; and is optionally substituted.

In one embodiment, $R^{SO}$ is unsubstituted.
In one embodiment, $R^{SO}$ is substituted.
Examples of substituents are described below, for example, as defined for $R^P$.

The Sulfonyl Substituent, $R^{SO}$: Phenyl Sulfonyl

In one embodiment, $R^{SO}$ is (an optionally substituted phenyl group):

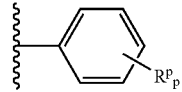

wherein p is an integer from 0 to 5, and each $R^P$ is a phenyl substituent.

In one embodiment, $R^{SO}$ is an unsubstituted phenyl group.
In one embodiment, $R^{SO}$ is a substituted phenyl group.
In one embodiment, p is 0, 1, 2, 3, 4 or 5.
In one embodiment, p is 0, 1, 2, 3, or 4.
In one embodiment, p is 0, 1, 2 or 3.
In one embodiment, p is 0, 1 or 2.
In one embodiment, p is 0 or 1.
In one embodiment, p is 1, 2, 3, 4 or 5.
In one embodiment, p is 1, 2, 3, or 4.
In one embodiment, p is 1, 2 or 3.
In one embodiment, p is 1 or 2.
In one embodiment, p is 0.
In one embodiment, p is 1.
In one embodiment, p is 2.
In one embodiment, p is 3.
In one embodiment, p is 4.
In one embodiment, p is 5.

If the phenyl group has less than the full complement of substituents, they may be arranged in any combination. For example, if the phenyl group has a single substituent other than hydrogen, it may be in the 2-, 3-, or 4-position. Similarly, if the phenyl group has two substituents other than hydrogen, they may be in the 2,3-, 2,4-, 2,5-, 2,6-, 3,4-, or 3,5-positions. If the phenyl group has three substituents other than hydrogen, they may be in, for example, the 2,3,4-, 2,3,5-, 2,3,6-, 2,4,5-, 2,5,6-, or 3,4,5-positions. If the phenyl group has four substituents other than hydrogen, they may be in, for example, the 3,4,5,6-, 2,4,5,6-, 2,3,5,6-, 2,3,4,6-, or 2,3,4,5-positions.

In one embodiment, p is 3 and the $R^P$ groups are in the 2-, 4-, and 6-positions.

In one embodiment, p is 3 and the $R^P$ groups are in the 3-, 4-, and 5-positions.

In one embodiment, p is 2 and the $R^P$ groups are in the 2- and 4-positions.

In one embodiment, p is 2 and the $R^P$ groups are in the 2- and 5-positions.

In one embodiment, p is 2 and the $R^P$ groups are in the 2- and 6-positions.

In one embodiment, p is 2 and the $R^P$ groups are in the 3- and 4-positions.

In one embodiment, p is 2 and the $R^P$ groups are in the 3- and 5-positions.

In one embodiment, p is 1 and $R^P$ is in the 2-, 3-, or 4-position.

In one embodiment, p is 1 and $R^P$ is in the 2- or 4-position.
In one embodiment, p is 1 and $R^P$ is in the 2-position.

In one embodiment, p is 1 and $R^P$ is in the 3-position.
In one embodiment, p is 1 and $R^P$ is in the 4-position.
Examples of substituents are described below.
When $R^{SO}$ is -Ph, the sulfonyl group, —$SO_2R^{SO}$, is "besyl."
When $R^{SO}$ is 4-Me, the sulfonyl group, —$SO_2R^{SO}$, is "tosyl."
When $R^{SO}$ is 4-Cl, the sulfonyl group, —$SO_2R^{SO}$, is "closyl."
When $R^{SO}$ is 4-Br, the sulfonyl group, —$SO_2R^{SO}$, is "brosyl."
When $R^{SO}$ is 4-$NO_2$, the sulfonyl group, —$SO_2R^{SO}$, is "nosyl."

The Sulfonyl Substituent, $R^{SO}$: Naphthyl Sulfonyl

In one embodiment, $R^{SO}$ is (an optionally substituted naphth-1-yl group or naphth-2-yl group):

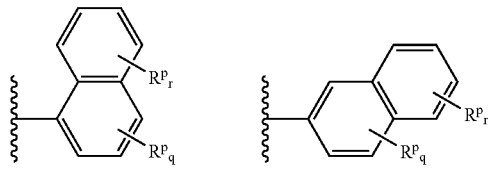

wherein q is an integer from 0 to 3; r is an integer from 0 to 4; and each $R^P$ is a naphthyl substituent.

In one embodiment, $R^{SO}$ is an unsubstituted naphth-1-yl group or naphth-2-yl group.
In one embodiment, $R^{SO}$ is a substituted naphth-1-yl group or naphth-2-yl group.
In one embodiment, $R^{SO}$ is an optionally substituted naphth-1-yl group.
In one embodiment, $R^{SO}$ is an unsubstituted naphth-1-yl group.
In one embodiment, $R^{SO}$ is a substituted naphth-1-yl group.
In one embodiment, $R^{SO}$ is an optionally substituted naphth-2-yl group.
In one embodiment, $R^{SO}$ is an unsubstituted naphth-2-yl group.
In one embodiment, $R^{SO}$ is a substituted naphth-2-yl group.
In one embodiment, q is 0, 1, 2 or 3.
In one embodiment, q is 0, 1 or 2.
In one embodiment, q is 0 or 1.
In one embodiment, q is 1, 2 or 3.
In one embodiment, q is 1 or 2.
In one embodiment, q is 0.
In one embodiment, q is 1.
In one embodiment, q is 2.
In one embodiment, q is 3.
In one embodiment, r is 0, 1, 2, 3, or 4.
In one embodiment, r is 0, 1, 2 or 3.
In one embodiment, r is 0, 1 or 2.
In one embodiment, r is 0 or 1.
In one embodiment, r is 1, 2, 3, or 4.
In one embodiment, r is 1, 2 or 3.
In one embodiment, r is 1 or 2.
In one embodiment, r is 0.
In one embodiment, r is 1.
In one embodiment, r is 2.
In one embodiment, r is 3.
In one embodiment, r is 4.

Examples of substituents are described below.
When $R^{SO}$ is 5-dimethylaminonaphth-1-yl, the sulfonyl group, —$SO_2R^{SO}$, is "dansyl."

The Sulfonyl Substituent, $R^{SO}$: Phenyl and Naphthyl Sulfonyl: Substituents $R^P$ In one embodiment, each $R^P$ is independently selected from:
halo; hydroxy; ether (e.g., $C_{1-7}$alkoxy); formyl; acyl (e.g., $C_{1-7}$alkylacyl, $C_{5-20}$arylacyl); carboxy; ester; acyloxy; amido; acylamido; thioamido; tetrazolyl; amino; nitro; azido; cyano; cyanato; thiocyano; isothiocyano; sulfhydryl; thioether (e.g., $C_{1-7}$alkylthio); sulfonic acid; sulfonate; sulfonyl; sulfonyloxy; sulfinyloxy; sulfamino; sulfonamino; sulfinamino; sulfamyl; sulfonamido; $C_{1-7}$alkyl (including, e.g., unsubstituted $C_{1-7}$alkyl, $C_{1-7}$haloalkyl, $C_{1-7}$hydroxyalkyl, $C_{1-7}$carboxyalkyl, $C_{1-7}$aminoalkyl, $C_{5-20}$aryl-$C_{1-7}$alkyl); $C_{3-20}$heterocyclyl; and $C_{5-20}$aryl (including, e.g., $C_{5-20}$carboaryl, $C_{5-20}$heteroaryl, $C_{1-7}$alkyl-$C_{5-20}$aryl and $C_{5-20}$haloaryl).

In one embodiment, each $R^P$ is independently selected from:
hydroxy (—OH);
halo;
cyano (—CN);
carboxy (—COOH);
azido;
ester;
amino, including e.g.,
    $C_{1-7}$alkyl-amino;
    amino-$C_{1-7}$alkyl-amino (e.g., —NH($CH_2)_w$-amino);
$C_{1-7}$alkyl, including, e.g.,
    halo-$C_{1-7}$alkyl;
    amino-$C_{1-7}$alkyl (e.g., —$(CH_2)_w$-amino);
    carboxy-$C_{1-7}$alkyl (e.g., —$(CH_2)_w$—COOH);
    hydroxy-$C_{1-7}$alkyl (e.g., —$(CH_2)_w$—OH);
    $C_{5-20}$aryl-$C_{1-7}$alkyl;
ether, including, e.g.,
    $C_{1-7}$alkoxy;
    halo-$C_{1-7}$alkoxy;
    amino-$C_{1-7}$alkoxy (e.g., —O$(CH_2)_w$-amino);
    carboxy-$C_{1-7}$alkoxy (e.g., —O$(CH_2)_w$—COOH);
    hydroxy-$C_{1-7}$alkoxy (e.g., —O$(CH_2)_w$—OH);
    $C_{5-20}$aryl-$C_{1-7}$alkoxy;
acyl, including, e.g.,
    $C_{1-7}$alkyl-acyl;
    halo-$C_{1-7}$alkyl-acyl;
    amino-$C_{1-7}$alkyl-acyl (e.g., —C(=O)$(CH_2)_w$-amino);
    carboxy-$C_{1-7}$alkyl-acyl (e.g., —C(=O)$(CH_2)_w$—COOH);
    hydroxy-$C_{1-7}$alkyl-acyl (e.g., —C(=O)$(CH_2)_w$—OH);
    $C_{5-20}$aryl-$C_{1-7}$alkyl-acyl;
    $C_{5-20}$aryl-acyl;
$C_{5-20}$aryl;
wherein w is an integer from 1 to 7, preferably 1 to 4, preferably 1, 2, or 3.

In one embodiment, each $R^P$ is independently selected from:
—OH;
—F, —Cl, —Br, —I;
—CN;
—COOH;
—$N_3$;
—COOMe, —COOEt, —COOtBu, —COOPh, —COOCH$_2$Ph;
—$NH_2$, —NHMe, —NHEt, —NMe$_2$, —NEt$_2$;

piperidino, morpholino, piperazino, N-methyl-piperazino;

—NH(CH$_2$)$_w$—NH$_2$, —NH(CH$_2$)$_w$—NHMe, —NH(CH$_2$)$_w$—NMe$_2$, —NH(CH$_2$)$_w$—NEt$_2$;

-Me, -Et, -nPr, -iPr, -nBu, -iBu, -sBu, -tBu;

—CH$_2$F, —CH$_2$Cl, —CF$_3$, —CCl$_3$, —CF$_2$CF$_3$, —CH$_2$CF$_3$, —C(CF$_3$)$_3$;

—(CH$_2$)$_w$—NH$_2$, —(CH$_2$)$_w$—NHMe, —(CH$_2$)$_w$—NMe$_2$, —(CH$_2$)$_w$—NEt$_2$;

—(CH$_2$)$_w$—COOH;

—(CH$_2$)$_w$—OH;

—CH$_2$Ph;

—OMe, —OEt, -OnPr, -OiPr, -OnBu, -OiBu, —OsBu, -OtBu;

—OCH$_2$F, —OCH$_2$Cl, —OCF$_3$, —OCCl$_3$, —OCF$_2$CF$_3$, —OCH$_2$CF$_3$, —OC(CF$_3$)$_3$;

—O(CH$_2$)$_w$—NH$_2$, —O(CH$_2$)$_w$—NHMe, —O(CH$_2$)$_w$—NMe$_2$, —O(CH$_2$)$_w$—NEt$_2$;

—O(CH$_2$)$_w$—COOH;

—O(CH$_2$)$_w$—OH;

—OCH$_2$Ph;

—C(=O)Me, —C(=O)Et, —C(=O)-nPr, —C(=O)-iPr, —C(=O)-nBu, —C(=O)-iBu, —C(=O)-sBu, —C(=O)-tBu;

—C(=O)CH$_2$F, —C(=O)CH$_2$Cl, —C(=O)CF$_3$, —C(=O)CCl$_3$, —C(=O)CF$_2$CF$_3$, —C(=O)CH$_2$CF$_3$, —C(=O)C(CF$_3$)$_3$;

—C(=O)(CH$_2$)$_w$—NH$_2$, —C(=O)(CH$_2$)$_w$—NHMe, —C(=O)(CH$_2$)$_w$—NMe$_2$, —C(=O)(CH$_2$)$_w$—NEt$_2$;

—C(=O)(CH$_2$)$_w$—COOH;

—C(=O)(CH$_2$)$_w$—OH;

—C(=O)CH$_2$Ph;

-Ph;

wherein w is an integer from 1 to 7, preferably 1 to 4, preferably 1, 2, or 3.

In one embodiment, each $R^P$ is independently selected from:
hydroxy (—OH);
halo;
C$_{1-7}$alkyl;
halo-C$_{1-7}$alkyl;
C$_{1-7}$alkoxy;
halo-C$_{1-7}$alkyl.

In one embodiment, each $R^P$ is independently selected from:
—OH;
—F, —Cl, —Br, —I;
-Me, -Et;
—CF$_3$, —CH$_2$CF$_3$, —C$_4$F$_9$;
—OMe, —OEt;
—OCF$_3$, —OCH$_2$CF$_3$, —OC$_4$F$_9$.

In one embodiment, each $R^P$ is independently selected from:
halo;
C$_{1-7}$alkyl;
C$_{1-7}$alkoxy.

In one embodiment, each $R^P$ is independently selected from:
—F, —Cl, —Br, —I, -Me, -Et, —OMe, —OEt.

In one embodiment, each $R^P$ is independently selected from:
—F, -Me, —OMe.

The Indol-2-yl Ring Substituents: $R^{3N}$, $R^{4N}$, $R^{5N}$, $R^{6N}$, and $R^{7N}$ In one embodiment, each of $R^{3N}$, $R^{4N}$, $R^{5N}$, $R^{6N}$, and $R^{7N}$ is independently —H, or as defined above for $R^P$.

In one embodiment, each of $R^{3N}$, $R^{4N}$, $R^{5N}$, $R^{6N}$, and $R^{7N}$ is independently —H, or selected from:
hydroxy (—OH);
halo;
C$_{1-7}$alkyl;
C$_{1-7}$alkoxy.

In one embodiment, each of $R^{3N}$, $R^{4N}$, $R^{5N}$, $R^{6N}$, and $R^{7N}$ is independently selected from:
—H, —OH, —F, —Cl, —Br, —I, -Me, -Et, —OMe, —OEt.

In one embodiment, each of $R^{3N}$, $R^{4N}$, $R^{5N}$, $R^{6N}$, and $R^{7N}$ is independently —H, or selected from:
halo;
C$_{1-7}$alkyl;
C$_{1-7}$alkoxy.

In one embodiment, each of $R^{3N}$, $R^{4N}$, $R^{5N}$, $R^{6N}$, and $R^{7N}$ is independently selected from:
—H, —F, —Cl, —Br, —I, -Me, -Et, —OMe, —OEt.

In one embodiment, each of $R^{3N}$, $R^{4N}$, $R^{5N}$, $R^{6N}$, and $R^{7N}$ is independently selected from:
—H, —F, —OMe.

In one embodiment, $R^{3N}$ is —H.

In one embodiment, each of $R^{4N}$ and $R^{7N}$ is —H.

In one embodiment, each of $R^{3N}$, $R^{4N}$ and $R^{7N}$ is —H.

In one embodiment, each of $R^{4N}$, $R^{6N}$, and $R^{7N}$ is —H.

In one embodiment, each of $R^{3N}$, $R^{4N}$, $R^{6N}$, and $R^{7N}$ is —H.

In one embodiment, each of $R^{4N}$, $R^{5N}$, and $R^{7N}$ is —H.

In one embodiment, each of $R^{3N}$, $R^{4N}$, $R^{5N}$, and $R^{7N}$ is —H.

In one embodiment, each of $R^{5N}$, $R^{6N}$, and $R^{7N}$ is —H.

In one embodiment, each of $R^{3N}$, $R^{5N}$, $R^{6N}$, and $R^{7N}$ is —H.

In one embodiment, each of $R^{4N}$, $R^{5N}$, and $R^{6N}$ is —H.

In one embodiment, each of $R^{3N}$, $R^{4N}$, $R^{5N}$, and $R^{6N}$ is —H.

In one embodiment, each of $R^{3N}$, $R^{4N}$, $R^{5N}$, $R^{6N}$, and $R^{7N}$ is —H.

Examples of Specific Embodiments

Some individual embodiments of the present invention include the following compounds:

SIQ-01

-continued
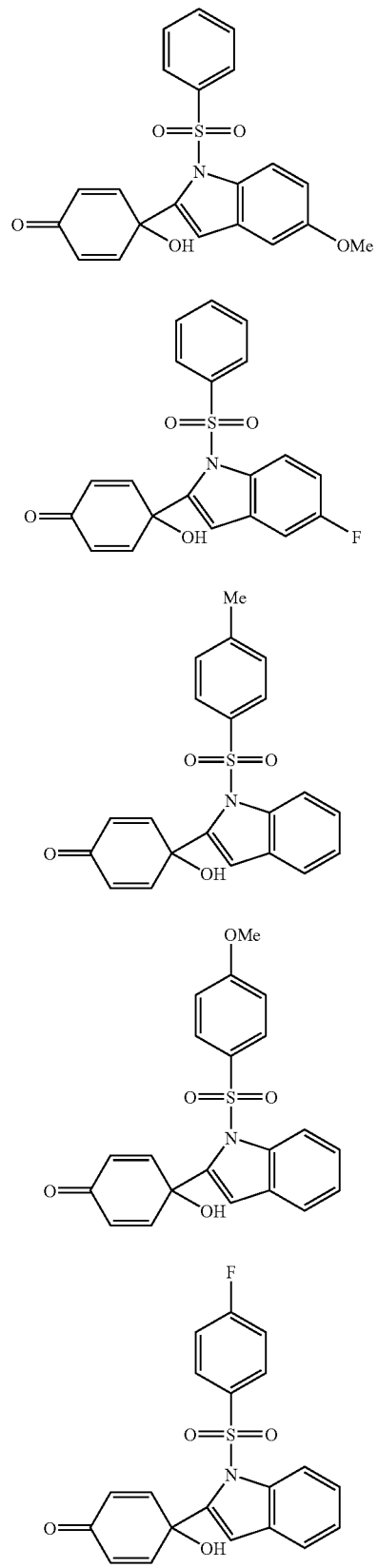
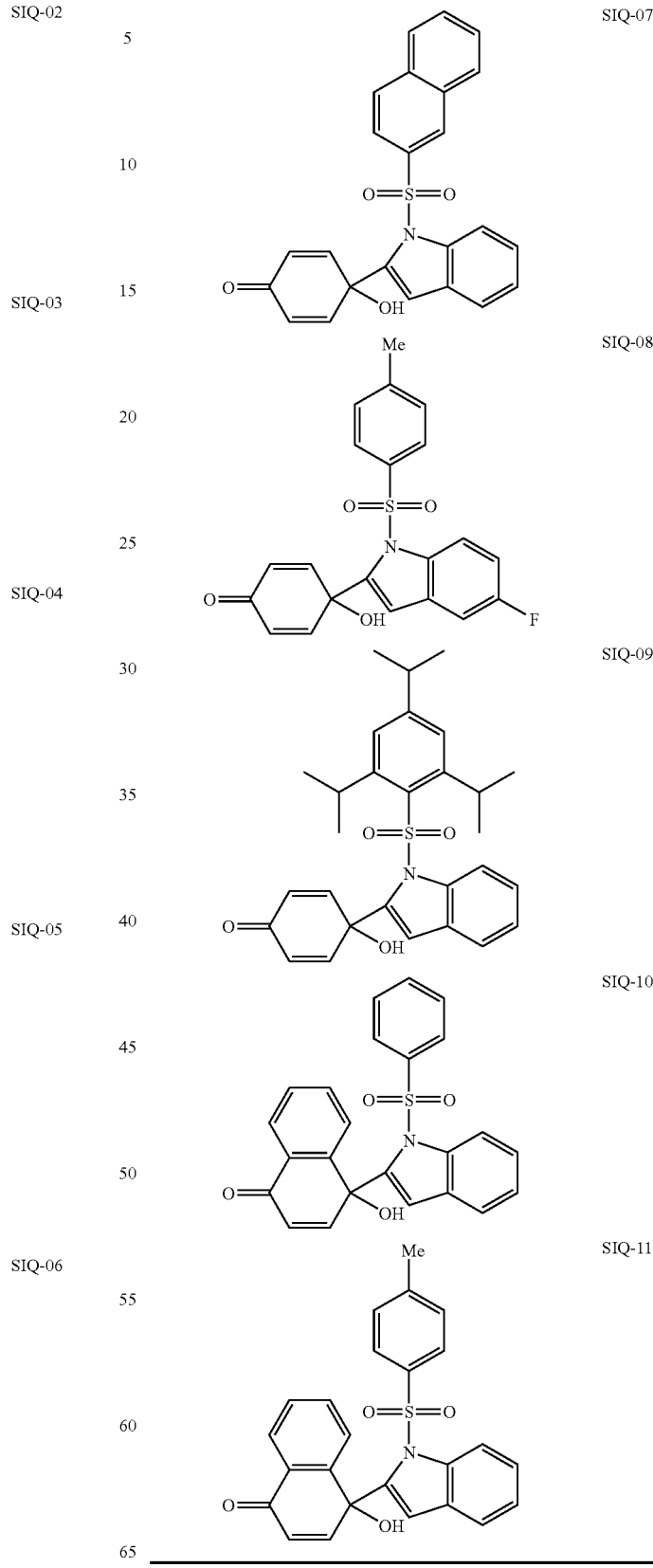

Examples of additional individual embodiments of the present invention include the following compounds:

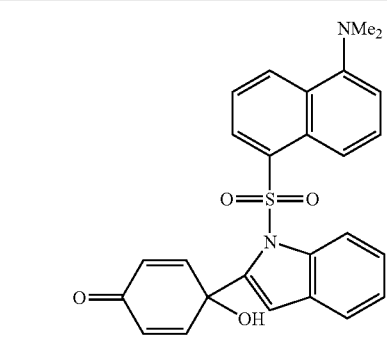
SIQ-12

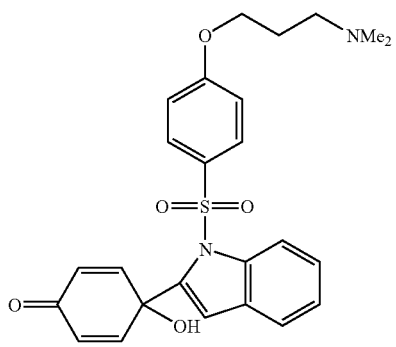
SIQ-13

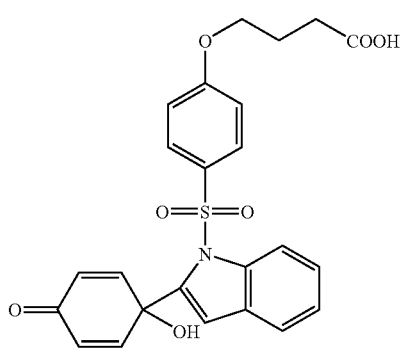
SIQ-14

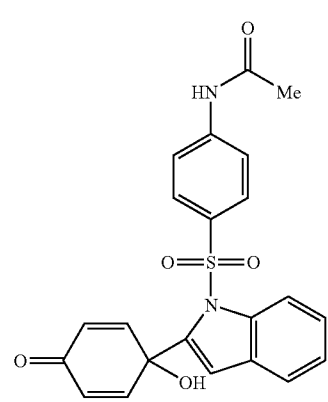
SIQ-15

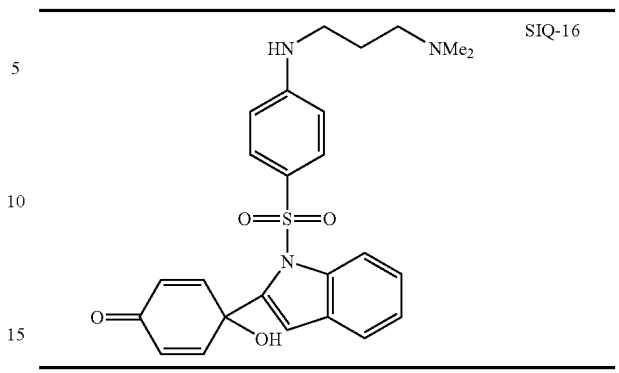
SIQ-16

Chemical Terms

The term "carbo," "carbyl," "hydrocarbon" and "hydrocarbyl," as used herein, pertain to compounds and/or groups which have only carbon and hydrogen atoms (but see "carbocyclic" below).

The term "hetero," as used herein, pertains to compounds and/or groups which have at least one heteroatom, for example, multivalent heteroatoms (which are also suitable as ring heteroatoms) such as boron, silicon, nitrogen, phosphorus, oxygen, sulfur, and selenium (more commonly nitrogen, oxygen, and sulfur) and monovalent heteroatoms, such as fluorine, chlorine, bromine, and iodine.

The term "saturated," as used herein, pertains to compounds and/orgroups which do not have any carbon-carbon double bonds or carbon-carbon triple bonds.

The term "unsaturated," as used herein, pertains to compounds and/or groups which have at least one carbon-carbon double bond or carbon-carbon triple bond. Compounds and/or groups may be partially unsaturated or fully unsaturated.

The term "aliphatic," as used herein, pertains to compounds and/or groups which are linear or branched, but not cyclic (also known as "acyclic" or "open-chain" groups).

The term "ring," as used herein, pertains to a closed ring of from 3 to 10 covalently linked atoms, more preferably 3 to 8 covalently linked atoms, yet more preferably 5 to 6 covalently linked atoms. A ring may be an alicyclic ring or an aromatic ring. The term "alicyclic ring," as used herein, pertains to a ring which is not an aromatic ring.

The term "carbocyclic ring," as used herein, pertains to a ring wherein all of the ring atoms are carbon atoms.

The term "carboaromatic ring," as used herein, pertains to an aromatic ring wherein all of the ring atoms are carbon atoms.

The term "heterocyclic ring," as used herein, pertains to a ring wherein at least one of the ring atoms is a multivalent ring heteroatom, for example, nitrogen, phosphorus, silicon, oxygen, or sulfur, though more commonly nitrogen, oxygen, or sulfur. Preferably, the heterocyclic ring has from 1 to 4 heteroatoms.

The term "cyclic compound," as used herein, pertains to a compound which has at least one ring. The term "cyclyl," as used herein, pertains to a monovalent moiety obtained by removing a hydrogen atom from a ring atom of a cyclic compound.

Where a cyclic compound has two or more rings, they may be fused (e.g., as in naphthalene, decalin, etc.), bridged (e.g., as in norbornane, adamantane, etc.), spiro (e.g., as in spiro[3.3]heptane), or a combination thereof. Cyclic compounds with one ring may be referred to as "monocyclic" or "mononuclear," whereas cyclic compounds with two or more rings may be referred to as "polycyclic" or "polynuclear."

The term "carbocyclic compound," as used herein, pertains to a cyclic compound which has only carbocyclic ring(s).

The term "heterocyclic compound," as used herein, pertains to a cyclic compound which has at least one heterocyclic ring.

The term "aromatic compound," as used herein, pertains to a cyclic compound which has at least one aromatic ring.

The term "carboaromatic compound," as used herein, pertains to a cyclic compound which has only carboaromatic ring(s).

The term "heteroaromatic compound," as used herein, pertains to a cyclic compound which has at least one heteroaromatic ring.

The term "monodentate substituents," as used herein, pertains to substituents which have one point of covalent attachment.

The term "monovalent monodentate substituents," as used herein, pertains to substituents which have one point of covalent attachment, via a single bond. Examples of such substituents include halo, hydroxy, and alkyl.

The term "multivalent monodentate substituents," as used herein, pertains to substituents which have one point of covalent attachment, but through a double bond or triple bond. Examples of such substituents include oxo, imino, alkylidene, and alklidyne.

The term "bidentate substituents," as used herein, pertains to substituents which have two points of covalent attachment, and which act as a linking group between two other moieties. Examples of such substituents include alkylene and arylene.

Substituents

The phrase "optionally substituted," as used herein, pertains to a parent group which may be unsubstituted or which may be substituted.

Unless otherwise specified, the term "substituted," as used herein, pertains to a parent group which bears one or more substitutents. The term "substituent" is used herein in the conventional sense and refers to a chemical moiety which is covalently attached to, or if appropriate, fused to, a parent group. A wide variety of substituents are well known, and methods for their formation and introduction into a variety of parent groups are also well known.

Examples of substituents are described in more detail below.

Alkyl: The term "alkyl," as used herein, pertains to a monovalent moiety obtained by removing a hydrogen atom from a carbon atom of a hydrocarbon compound having from 1 to 20 carbon atoms (unless otherwise specified), which may be aliphatic or alicyclic, and which may be saturated or unsaturated (e.g., partially unsaturated, fully unsaturated). Thus, the term "alkyl" includes the sub-classes alkenyl, alkynyl, cycloalkyl, cycloalkyenyl, cycloalkynyl, etc., discussed below.

In the context of alkyl groups, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkyl," as used herein, pertains to an alkyl group having from 1 to 4 carbon atoms. Examples of groups of alkyl groups include $C_{1-4}$alkyl ("lower alkyl"), $C_{1-7}$alkyl, and $C_{1-20}$alkyl. Note that the first prefix may vary according to other limitations; for example, for unsaturated alkyl groups, the first prefix must be at least 2; for cyclic alkyl groups, the first prefix must be at least 3; etc.

Examples of (unsubstituted) saturated alkyl groups include, but are not limited to, methyl ($C_1$), ethyl ($C_2$), propyl ($C_3$), butyl ($C_4$), pentyl ($C_5$), hexyl ($C_6$), heptyl ($C_7$), octyl ($C_8$), nonyl ($C_9$), decyl ($C_{10}$), undecyl ($C_{11}$), dodecyl ($C_{12}$), tridecyl ($C_{13}$), tetradecyl ($C_{14}$), pentadecyl ($C_{15}$), and eicodecyl ($C_{20}$).

Examples of (unsubstituted) saturated linear alkyl groups include, but are not limited to, methyl ($C_1$), ethyl ($C_2$), n-propyl ($C_3$), n-butyl ($C_4$), n-pentyl (amyl) ($C_5$), n-hexyl ($C_6$), and n-heptyl ($C_7$).

Examples of (unsubstituted) saturated branched alkyl groups include iso-propyl ($C_3$), iso-butyl ($C_4$), sec-butyl ($C_4$), tert-butyl ($C_4$), iso-pentyl ($C_5$), and neo-pentyl ($C_5$).

Alkenyl: The term "alkenyl," as used herein, pertains to an alkyl group having one or more carbon-carbon double bonds. Examples of groups of alkenyl groups include $C_{2-4}$alkenyl, $C_{2-7}$alkenyl, $C_{2-20}$alkenyl.

Examples of (unsubstituted) unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$), butenyl ($C_4$), pentenyl ($C_5$), and hexenyl ($C_6$).

Alkynyl: The term "alkynyl," as used herein, pertains to an alkyl group having one or more carbon-carbon triple bonds. Examples of groups of alkynyl groups include $C_{2-4}$alkynyl, $C_{2-7}$alkynyl, $C_{2-20}$alkynyl.

Examples of (unsubstituted) unsaturated alkynyl groups include, but are not limited to, ethynyl (ethinyl, —C≡CH) and 2-propynyl (propargyl, —CH$_2$C≡CH).

Cycloalkyl: The term "cycloalkyl," as used herein, pertains to an alkyl group which is also a cyclyl group; that is, a monovalent moiety obtained by removing a hydrogen atom from an alicyclic ring atom of a carbocyclic ring of a carbocyclic compound, which carbocyclic ring may be saturated or unsaturated (e.g., partially unsaturated, fully unsaturated), which moiety has from 3 to 20 carbon atoms (unless otherwise specified), including from 3 to 20 ring atoms. Thus, the term "cycloalkyl" includes the sub-classes cycloalkyenyl and cycloalkynyl. Preferably, each ring has from 3 to 7 ring atoms. Examples of groups of cycloalkyl groups include $C_{3-20}$cycloalkyl, $C_{3-15}$cycloalkyl, $C_{3-10}$cycloalkyl, $C_{3-7}$cycloalkyl.

Examples of cycloalkyl groups include, but are not limited to, those derived from:
saturated monocyclic hydrocarbon compounds: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);
unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);
saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);
unsaturated polycyclic hydrocarbon compounds: camphene ($C_{10}$), limonene ($C_{10}$), pinene ($C_{10}$);

polycyclic hydrocarbon compounds having an aromatic ring: indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

Alkylidene: The term "alkylidene," as used herein, pertains to a divalent monodentate moiety obtained by removing two hydrogen atoms from an aliphatic or alicyclic carbon atom of a hydrocarbon compound having from 1 to 20 carbon atoms (unless otherwise specified). Examples of groups of alkylidene groups include $C_{1-20}$alkylidene, $C_{1-7}$alkylidene, $C_{1-4}$alkylidene.

Examples of alkylidene groups include, but are not limited to, methylidene (=$CH_2$), ethylidene (=CH—$CH_3$), vinylidene (=C=$CH_2$), isopropylidene (=C($CH_3$)$_2$), cyclopentylidene. An example of a substituted alkylidene group is benzylidene (=CH-Ph).

Alkylidyne: The term "alkylidyne," as used herein, pertains to a trivalent monodentate moiety obtained by removing three hydrogen atoms from an aliphatic or alicyclic carbon atom of a hydrocarbon compound having from 1 to 20 carbon atoms (unless otherwise specified). Examples of groups of alkylidyne groups include $C_{1-20}$alkylidyne, $C_{1-7}$alkylidyne, $C_{1-4}$alkylidyne.

Examples of alkylidyne groups include, but are not limited to, methylidyne (≡CH) and ethylidyne (≡C—$CH_3$). An example of a substituted alkylidene group is benzylidyne (≡C-Ph).

Carbocyclyl: The term "carbocyclyl," as used herein, pertains to a monovalent moiety obtained by removing a hydrogen atom from a ring atom of a carbocyclic compound, which moiety has from 3 to 20 ring atoms (unless otherwise specified). Preferably, each ring has from 3 to 7 ring atoms.

In this context, the prefixes (e.g., $C_{3-20}$, $C_{3-7}$, $C_{5-6}$, etc.) denote the number of ring atoms, or range of number of ring atoms. For example, the term "$C_{5-6}$carbocyclyl," as used herein, pertains to a carbocyclyl group having 5 or 6 ring atoms. Examples of groups of carbocyclyl groups include $C_{3-20}$carbocyclyl, $C_{3-10}$carbocyclyl, $C_{5-10}$ocarbocyclyl, $C_{3-7}$carbocyclyl, and $C_{5-7}$carbocyclyl.

Examples of carbocyclic groups include, but are not limited to, those described above as cycloalkyl groups; and those described below as carboaryl groups.

Heterocyclyl: The term "heterocyclyl," as used herein, pertains to a monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms.

In this context, the prefixes (e.g., $C_{3-20}$, $C_{3-7}$, $C_{5-6}$, etc.) denote the number of ring atoms, or range of number of ring atoms, whether carbon atoms or heteroatoms. For example, the term "$C_{5-6}$heterocyclyl," as used herein, pertains to a heterocyclyl group having 5 or 6 ring atoms. Examples of groups of heterocyclyl groups include $C_{3-20}$heterocyclyl, $C_{5-20}$heterocyclyl, $C_{3-15}$heterocyclyl, $C_{5-15}$heterocyclyl, $C_{3-12}$heterocyclyl, $C_{5-12}$heterocyclyl, $C_{3-10}$heterocyclyl, $C_{5-10}$heterocyclyl, $C_{3-7}$heterocyclyl, $C_{5-7}$heterocyclyl, and $C_{5-6}$heterocyclyl.

Examples of (non-aromatic) monocyclic heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietahe ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of heterocyclyl groups which are also heteroaryl groups are described below with aryl groups.

Aryl: The term "aryl," as used herein, pertains to a monovalent moiety obtained by removing a hydrogen atom from an aromatic ring atom of an aromatic compound, which moiety has from 3 to 20 ring atoms (unless otherwise specified). Preferably, each ring has from 5 to 7 ring atoms.

In this context, the prefixes (e.g., $C_{3-20}$, $C_{5-7}$, $C_{5-6}$, etc.) denote the number of ring atoms, or range of number of ring atoms, whether carbon atoms or heteroatoms. For example, the term "$C_{5-6}$aryl," as used herein, pertains to ani aryl group having 5 or 6 ring atoms. Examples of groups of aryl groups include $C_{3-20}$aryl, $C_{5-20}$aryl, $C_{5-15}$aryl, $C_{5-12}$aryl, $C_{5-10}$aryl, $C_{5-7}$aryl, $C_{5-6}$aryl, $C_5$aryl, and $C_6$aryl.

The ring atoms may be all carbon atoms, as in "carboaryl groups." Examples of carboaryl groups include $C_{3-20}$carboaryl, $C_{5-20}$carboaryl, $C_{5-15}$carboaryl, $C_{5-12}$carboaryl, $C_{5-10}$carboaryl, $C_{5-7}$carboaryl, $C_{5-6}$carboaryl, $C_5$carboaryl, and $C_6$carboaryl.

Examples of carboaryl groups include, but are not limited to, those derived from benzene (i.e., phenyl) ($C_6$), naphthalene ($C_{10}$), azulene ($C_{10}$), anthracene ($C_{14}$), phenanthrene ($C_{14}$), naphthacene ($C_{18}$), and pyrene ($C_{16}$).

Examples of aryl groups which comprise fused rings, at least one of which is an aromatic ring, include, but are not limited to, groups derived from indane (e.g., 2,3-dihydro-1H-indene) ($C_9$), indene ($C_9$), isoindene ($C_9$), tetraline (1,2,3,4-tetrahydronaphthalene ($C_{10}$), acenaphthene ($C_{12}$), fluorene ($C_{13}$), phenalene ($C_{13}$), acephenanthrene ($C_{15}$), and aceanthrene ($C_{16}$).

Alternatively, the ring atoms may include one or more heteroatoms, as in "heteroaryl groups." Examples of heteroaryl groups include $C_{3-20}$heteroaryl, $C_{5-20}$heteroaryl, $C_{5-15}$heteroaryl, $C_{5-12}$heteroaryl, $C_{5-10}$heteroaryl, $C_{5-7}$heteroaryl, $C_{5-6}$heteroaryl, $C_5$heteroaryl, and $C_6$heteroaryl.

Examples of monocyclic heteroaryl groups include, but are not limited to, those derived from:
$N_1$: pyrrole (azole) ($C_5$), pyridine (azine) ($C_6$);

$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$);
$N_3$: triazole ($C_5$), triazine ($C_6$); and,
$N_4$: tetrazole ($C_5$).

Examples of heterocyclic groups (some of which are also heteroaryl groups) which comprise fused rings, include, but are not limited to:

$C_9$heterocylic groups (with 2 fused rings) derived from benzofuran ($O_1$), isobenzofuran ($O_1$), indole ($N_1$), isoindole ($N_1$), indolizine ($N_1$), indoline ($N_1$), isoindoline ($N_1$), purine ($N_4$) (e.g., adenine, guanine), benzimidazole ($N_2$), indazole ($N_2$), benzoxazole ($N_1O_1$), benzisoxazole ($N_1O_1$), benzodioxole ($O_2$), benzofurazan ($N_2O_1$), benzotriazole ($N_3$), benzothiofuran ($S_1$), benzothiazole ($N_1S_1$), benzothiadiazole ($N_2S$);

$C_{10}$heterocylic groups (with 2 fused rings) derived from chromene ($O_1$), isochromene ($O_1$), chroman ($O_1$), isochroman ($O_1$), benzodioxan ($O_2$), quinoline ($N_1$), isoquinoline ($N_1$), quinolizine ($N_1$), benzoxazine ($N_1O_1$), benzodiazine ($N_2$), pyridopyridine ($N_2$), quinoxaline ($N_2$), quinazoline ($N_2$), cinnoline ($N_2$), phthalazine ($N_2$), naphthyridine ($N_2$), pteridine ($N_4$);

$C_{11}$heterocylic groups (with 2 fused rings) derived from benzodiazepine ($N_2$);

$C_{13}$heterocylic groups (with 3 fused rings) derived from carbazole ($N_1$), dibenzofuran ($O_1$), dibenzothiophene ($S_1$), carboline ($N_2$), perimidine ($N_2$), pyridoindole ($N_2$); and, $C_{14}$heterocylic groups (with 3 fused rings) derived from acridine ($N_1$), xanthene ($O_1$), thioxanthene ($S_1$), oxanthrene ($O_2$), phenoxathiin ($O_1S_1$), phenazine ($N_2$), phenoxazine ($N_1O_1$), phenbthiazine ($N_1S_1$), thianthrene ($S_2$), phenanthridine ($N_1$), phenanthroline ($N_2$), phenazine ($N_2$).

Heterocyclic groups (including heteroaryl groups) which have a nitrogen ring atom in the form of an —NH— group may be N-substituted, that is, as —NR—. For example, pyrrole may be N-methyl substituted, to give N-methylpyrrole. Examples of N-substitutents include, but are not limited to $C_{1-7}$alkyl, $C_{3-20}$heterocyclyl, $C_{5-20}$aryl, and acyl groups.

Heterocyclic groups (including heteroaryl groups) which have a nitrogen ring atom in the form of an —N= group may be substituted in the form of an N-oxide, that is, as —N(→O)= (also denoted —N$^+$(→O$^-$)=). For example, quinoline may be substituted to give quinoline N-oxide; pyridine to give pyridine N-oxide; benzofurazan to give benzofurazan N-oxide (also known as benzofuroxan).

Cyclic groups may additionally bear one or more oxo (=O) groups on ring carbon atoms.

Monocyclic examples of such groups include, but are not limited to, those derived from:

$C_5$: cyclopentanone, cyclopentenone, cyclopentadienone;
$C_6$: cyclohexanone, cyclohexenone, cyclohexadienone;
$O_1$: furanone ($C_5$), pyrone ($C_6$);
$N_1$: pyrrolidone (pyrrolidinone) ($C_5$), piperidinone (piperidone) ($C_6$), piperidinedione ($C_6$);
$N_2$: imidazolidone (imidazolidinone) ($C_5$), pyrazolone (pyrazolinone) ($C_5$), piperazinone ($C_6$), piperazinedione ($C_6$), pyridazinone ($C_6$), pyrimidinone ($C_6$) (e.g., cytosine), pyrimidinedione ($C_6$) (e.g., thymine, uracil), barbituric acid ($C_6$);
$N_1S_1$: thiazolone ($C_5$), isothiazolone ($C_5$);
$N_1O_1$: oxazolinone ($C_5$).

Polycyclic examples of such groups include, but are not limited to, those derived from:

$C_9$: indenedione;
$C_{10}$: tetralone, decalone;
$C_{14}$: anthrone, phenanthrone;
$N_1$: oxindole ($C_9$);
$O_1$: benzopyrone (e.g., coumarin, isocoumarin, chromone) ($C_{10}$);
$N_1O_1$: benzoxazolinone ($C_9$), benzoxazolinone ($C_{10}$);
$N_2$: quinazolinedione ($C_{10}$); benzodiazepinone ($C_{11}$); benzodiazepinedione ($C_{11}$);
$N_4$: purinone ($C_9$) (e.g., guanine).

Still more examples of cyclic groups which bear one or more oxo (=O) groups on ring carbon atoms include, but are not limited to, those derived from:

cyclic anhydrides (—C(=O)—O—C(=O)— in a ring), including but not limited to maleic anhydride ($C_5$), succinic anhydride ($C_5$), and glutaric anhydride ($C_6$);

cyclic carbonates (—O—C(=O)—O— in a ring), such as ethylene carbonate ($C_5$) and 1,2-propylene carbonate ($C_5$);

imides (—C(=O)—NR—C(=O)— in a ring), including but not limited to, succinimide ($C_5$), maleimide ($C_5$), phthalimide, and glutarimide ($C_6$);

lactones (cyclic esters, —O—C(=O)— in a ring), including, but not limited to, β-propiolactone, γ-butyrolactone, δ-valerolactone (2-piperidone), and ε-caprolactone;

lactams (cyclic amides, —NR—C(=O)— in a ring), including, but not limited to, β-propiolactam ($C_4$), γ-butyrolactam (2-pyrrolidone) ($C_5$), δ-valerolactam ($C_6$), and ε-caprolactam ($C_7$);

cyclic carbamates (—O—C(=O)—NR— in a ring), such as 2-oxazolidone ($C_5$); cyclicureas (—NR—C(=O)—NR— in a ring), such as 2-imidazolidone ($C_5$) and pyrimidine-2,4dione (e.g., thymine, uracil) ($C_6$).

The above alkyl, alkylidene, alkylidyne, heterocyclyl, and aryl groups, whether alone or part of another substituent, may themselves optionally be substituted with one or more groups selected from themselves and the additional substituents listed below.

Hydrogen: —H. Note that if the substituent at a particular position is hydrogen, it may be convenient to refer to the compound as being "unsubstituted" at that position.

Halo: —F, —Cl, —Br, and —I.

Hydroxy: —OH.

Ether: —OR, wherein R is an ether substituent, for example, a $C_{1-7}$alkyl group (also referred to as a $C_{1-7}$alkoxy group, discussed below), a $C_{3-20}$heterocyclyl group (also referred to as a $C_{3-20}$heterocyclyloxy group), or a $C_{5-20}$aryl group (also referred to as a $C_{5-20}$aryloxy group), preferably a $C_{1-7}$alkyl group.

$C_{1-7}$alkoxy: —OR, wherein R is a $C_{1-7}$alkyl group. Examples of $C_{1-7}$alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

Acetal: —CH(OR$^1$)(OR$^2$), wherein R$^1$ and R$^2$ are independently acetal substituents, for example, a $C_{1-7}$alkyl group, a $C_{3-20}$heterocyclyl group, or a $C_{5-20}$aryl group, preferably a $C_{1-7}$alkyl group, or, in the case of a "cyclic"

acetal group, $R^1$ and $R^2$, taken together with the two oxygen atoms to which they are attached, and the carbon atoms to which they are attached, form a heterocyclic ring having from 4 to 8 ring atoms. Examples of acetal groups include, but are not limited to, —CH(OMe)$_2$, —CH(OEt)$_2$, and —CH(OMe)(OEt).

Hemiacetal: —CH(OH)(OR$^1$), wherein $R^1$ is a hemiacetal substituent, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —CH(OH)(OMe) and —CH(OH)(OEt).

Ketal: —CR(OR$^1$)(OR$^2$), where $R^1$ and $R^2$ are as defined for acetals, and R is a ketal substituent other than hydrogen, for example, a $C_{1-7}$alkyl group, a $C_{3-20}$heterocyclyl group, or a $C_{5-20}$aryl group, preferably a $C_{1-7}$alkyl group. Examples ketal groups include, but are not limited to, —C(Me)(OMe)$_2$, —C(Me)(OEt)$_2$, —C(Me)(OMe)(OEt), —C(Et)(OMe)$_2$, —C(Et)(OEt)$_2$, and —C(Et)(OMe)(OEt).

Hemiketal: —CR(OH)(OR$^1$), where $R^1$ is as defined for hemiacetals, and R is a hemiketal substituent other than hydrogen, for example, a $C_{1-7}$alkyl group, a $C_{3-20}$heterocyclyl group, or a $C_{5-20}$aryl group, preferably a $C_{1-7}$alkyl group. Examples of hemiacetal groups include, but are not limited to, —C(Me)(OH)(OMe), —C(Et)(OH)(OMe), —C(Me)(OH)(OEt), and —C(Et)(OH)(OEt).

Oxo (keto, -one): =O.

Thione (thioketone): =S.

Imino (imine): =NR, wherein R is an imino substituent, for example, hydrogen, $C_{1-7}$alkyl group, a $C_{3-20}$heterocyclyl group, or a $C_{5-20}$aryl group, preferably hydrogen or a $C_{1-7}$alkyl group. Examples of ester groups include, but are not limited to, =NH, =NMe, NEt, and =NPh.

Formyl (carbaldehyde, carboxaldehyde): —C(=O)H.

Acyl (keto): —C(=O)R, wherein R is an acyl substituent, for example, a $C_{1-7}$alkyl group (also referred to as $C_{1-7}$alkylacyl or $C_{1-7}$alkanoyl), a $C_{3-20}$heterocyclyl group (also referred to as $C_{3-20}$heterocyclylacyl), or a $C_{5-20}$aryl group (also referred to as $C_{5-20}$arylacyl), preferably a $C_{1-7}$alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

Carboxy (carboxylic acid): —C(=O)OH.

Thiocarboxy (thiocarboxylic acid): —C(=S)SH.

Thiolocarboxy (thiolocarboxylic acid): —C(=O)SH.

Thionocarboxy (thionocarboxylic acid): —C(=S)OH.

Imidic acid: —C(=NH)OH.

Hydroxamic acid: —C(=NOH)OH.

Ester (carboxylate, carboxylic acid ester, oxycarbonyl): —C(=O)OR, wherein R is an ester substituent, for example, a $C_{1-7}$alkyl group, a $C_{3-20}$heterocyclyl group, or a $C_{5-20}$aryl group, preferably a $C_{1-7}$alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

Acyloxy (reverse ester): —OC(=O)R, wherein R is an acyloxy substituent, for example, a $C_{1-7}$alkyl group, a $C_{3-20}$heterocyclyl group, or a $C_{5-20}$aryl group, preferably a $C_{1-7}$alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

Amido (carbamoyl, carbamyl, aminocarbonyl, carboxamide): —C(=O)NR$^1$R$^2$, wherein $R^1$ and $R^2$ are independently amino substituents, as defined for amino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which $R^1$ and $R^2$, together with the nitrogen atom to which they are attached, form a heterocyclic structure as in, for example, piperidinocarbonyl, morpholinocarbonyl, thiomorpholinocarbonyl, and piperazinocarbonyl.

Acylamido (acylamino): —NR$^1$C(=O)R$^2$, wherein $R^1$ is an amide substituent, for example, hydrogen, a $C_{1-7}$alkyl group, a $C_{3-20}$heterocyclyl group, or a $C_{5-20}$aryl group, preferably hydrogen or a $C_{1-7}$alkyl group, and $R^2$ is an acyl substituent, for example, a $C_{1-7}$alkyl group, a $C_{3-20}$heterocyclyl group, or a $C_{5-20}$aryl group, preferably hydrogen or a $C_{1-7}$alkyl group. Examples of acylamide groups include, but are not limited to, —NHC(=O)CH$_3$, —NHC(=O)CH$_2$CH$_3$, and —NHC(=O)Ph. $R^1$ and $R^2$ may together form a cyclic structure, as in, for example, succinimidyl, maleimidyl, and phthalimidyl:

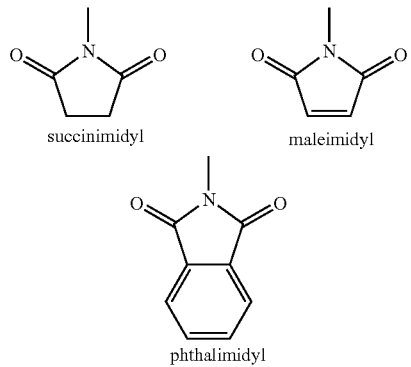

succinimidyl  maleimidyl phthalimidyl

Thioamido (thiocarbamyl): —C(=S)NR$^1$R$^2$, wherein $R^1$ and $R^2$ are independently amino substituents, as defined for amino groups. Examples of amido groups include, but are not limited to, —C(=S)NH$_2$, —C(=S)NHCH$_3$, —C(=S)N(CH$_3$)$_2$, and —C(=S)NHCH$_2$CH$_3$.

Ureido: —N(R$^1$)CONR$^2$R$^3$ wherein $R^2$ and $R^3$ are independently amino substituents, as defined for amino groups, and R1 is a ureido substituent, for example, hydrogen, a $C_{1-7}$alkyl group, a $C_{3-20}$heterocyclyl group, or a $C_{5-20}$aryl group, preferably hydrogen or a $C_{1-7}$alkyl group. Examples of ureido groups include, but are not limited to, —NHCONH$_2$, —NHCONHMe, —NHCONHEt, —NHCONMe$_2$, —NHCONEt$_2$, —NMeCONH$_2$, —NMeCONHMe, —NMeCONHEt, —NMeCONMe$_2$, and —NMeCONEt$_2$.

Guanidino: —NH—C(=NH)NH$_2$.

Tetrazolyl: a five membered aromatic ring having four nitrogen atoms and one carbon atom,

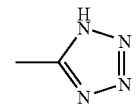

Amino: —NR$^1$R$^2$, wherein $R^1$ and $R^2$ are independently amino substituents, for example, hydrogen, a $C_{1-7}$alkyl group (also referred to as $C_{1-7}$alkylamino or di-$C_{1-7}$alkylamino), a $C_{3-20}$heterocyclyl group, or a $C_{5-20}$aryl group, preferably H or a $C_{1-7}$alkyl group, or, in the case of a "cyclic" amino group, $R^1$ and $R^2$, taken together with the nitrogen atom to which they are attached, form a heterocyclic ring having from 4 to 8 ring atoms. Amino groups may be primary (—NH$_2$), secondary (—NHR$^1$), or tertiary (—NHR$^1$R$^2$), and in cationic form, may be quaternary (—$^+$NR$^1$R$^2$R$^3$). Examples of amino groups include, but are not limited to, —NH$_2$, —NHCH$_3$, —NHC(CH$_3$)$_2$, —N(CH$_3$)$_2$, —N(CH$_2$CH$_3$)$_2$, and —NHPh. Examples of cyclic amino groups include, but are not limited to, aziridino, azetidino, pyrrolidino, piperidino, piperazino, morpholino, and thiomorpholino.

Imino: =NR, wherein R is an imino substituent, for example, for example, hydrogen, a C$_{1-7}$alkyl group, a C$_{3-20}$heterocyclyl group, or a C$_{5-20}$aryl group, preferably H or a C$_{1-7}$alkyl group. Examples of imino groups include, but are not limited to, =NH, =NMe, and =NEt.

Amidine (amidino): —C(=NR)NR$_2$, wherein each R is an amidine substituent, for example, hydrogen, a C$_{1-7}$alkyl group, a C$_{3-20}$heterocyclyl group, or a C$_{5-20}$aryl group, preferably H or a C$_{1-7}$alkyl group. Examples of amidine groups include, but are not limited to, —C(=NH)NH$_2$, —C(=NH)NMe$_2$, and —C(=NMe)NMe$_2$.

Nitro: —NO$_2$.

Azido: —N$_3$.

Cyano (nitrile, carbonitrile): —CN.

Cyanato: —OCN.

Thiocyano (thiocyanato): —SCN.

Isothiocyano (isothiocyanato): —NCS.

Sulfhydryl (thiol, mercapto): —SH.

Thioether (sulfide): —SR, wherein R is a thioether substituent, for example, a C$_{1-7}$alkyl group (also referred to as a C$_{1-7}$alkylthio group), a C$_{3-20}$heterocyclyl group, or a C$_{5-20}$aryl group, preferably a C$_{1-7}$alkyl group. Examples of C$_{1-7}$alkylthio groups include, but are not limited to, —SCH$_3$ and —SCH$_2$CH$_3$.

Disulfide: —SS—R, wherein R is a disulfide substituent, for example, a C$_{1-7}$alkyl group, a C$_{3-20}$heterocyclyl group, or a C$_{5-20}$aryl group, preferably a C$_{1-7}$alkyl group (also referred to herein as C$_{1-7}$alkyl disulfide). Examples of C$_{1-7}$alkyl disulfide groups include, but are not limited to, —SSCH$_3$ and —SSCH$_2$CH$_3$.

Sulfonic acid (sulfo): —S(=O)$_2$OH, —SO$_3$H.

Sulfonate (sulfonic acid ester): —S(=O)$_2$OR, wherein R is a sulfonate substituent, for example, a C$_{1-7}$alkyl group, a C$_{3-20}$heterocyclyl group, or a C$_{5-20}$aryl group, preferably a C$_{1-7}$alkyl group. Examples of sulfonate groups include, but are not limited to, —S(=O)$_2$OCH$_3$ and —S(=O)$_2$OCH$_2$CH$_3$.

Sulfinic acid: —S(=O)OH, —SO$_2$H.

Sulfinate (sulfinic acid ester): —S(=O)OR; wherein R is a sulfinate substituent, for example, a C$_{1-7}$alkyl group, a C$_{3-20}$heterocyclyl group, or a C$_{5-20}$aryl group, preferably a C$_{1-7}$alkyl group. Examples of sulfinate groups include, but are not limited to, —S(=O)OCH$_3$ and —S(=O)OCH$_2$CH$_3$.

Sulfate: —OS(=O)$_2$OR; wherein R is a sulfate substituent, for example, a C$_{1-7}$alkyl group, a C$_{3-20}$heterocyclyl group, or a C$_{5-20}$aryl group, preferably a C$_{1-7}$alkyl group. Examples of sulfate groups include, but are not limited to, —OS(=O)$_2$OCH$_3$ and —SO(=O)$_2$OCH$_2$CH$_3$.

Sulfone (sulfonyl): —S(=O)$_2$R, wherein R is a sulfone substituent, for example, a C$_{1-7}$alkyl group, a C$_{3-20}$heterocyclyl group, or a C$_{5-20}$aryl group, preferably a C$_{1-7}$alkyl group, for example, a fluorinated or perfluorinated C$_{1-7}$alkyl group. Examples of sulfone groups include, but are not limited to, —S(=O)$_2$CH$_3$ (methanesulfonyl, mesyl), —S(=O)$_2$CF$_3$ (triflyl), —S(=O)$_2$CH$_2$CH$_3$ (esyl), —S(=O)$_2$C$_4$F$_9$ (nonaflyl), —S(=O)$_2$CH$_2$CF$_3$ (tresyl), —S(=O)$_2$Ph (phenylsulfonyl, besyl), 4-methylphenylsulfonyl (tosyl), 4-chlorophenylsulfonyl (closyl), 4-bromophenylsulfonyl (brosyl), 4-nitrophenyl (nosyl), 2-naphthalenesulfonate (napsyl), and 5-dimethylamino-naphthalen-1-ylsulfonate (dansyl).

Sulfine (sulfinyl, sulfoxide): —S(=O)R, wherein R is a sulfine substituent, for example, a C$_{1-7}$alkyl group, a C$_{3-20}$heterocyclyl group, or a C$_{5-20}$aryl group, preferably a C$_{1-7}$alkyl group. Examples of sulfine groups include, but are not limited to, —S(=O)CH$_3$ and —S(=O)CH$_2$CH$_3$.

Sulfonyloxy: —OS(=O)$_2$R, wherein R is a sulfonyloxy substituent, for example, a C$_{1-7}$alkyl group, a C$_{3-20}$heterocyclyl group, or a C$_{5-20}$aryl group, preferably a C$_{1-7}$alkyl group. Examples of sulfonyloxy groups include, but are not limited to, —OS(=O)$_2$CH$_3$ (mesylate) and —OS(=O)$_2$CH$_2$CH$_3$ (esylate).

Sulfinyloxy: —OS(=O)R, wherein R is a sulfinyloxy substituent, for example, a C$_{1-7}$alkyl group, a C$_{3-20}$heterocyclyl group, or a C$_{5-20}$aryl group, preferably a C$_{1-7}$alkyl group. Examples of sulfinyloxy groups include, but are not limited to, —OS(=O)CH$_3$ and —OS(=O)CH$_2$CH$_3$.

Sulfamino: —NR$^1$S(=O)$_2$OH, wherein R$^1$ is an amino substituent, as defined for amino groups. Examples of sulfamino groups include, but are not limited to, —NHS(=O)$_2$OH and —N(CH$_3$)S(=O)$_2$OH.

Sulfonamino: —NR$^1$S(=O)$_2$R, wherein R$^1$ is an amino substituent, as defined for amino groups, and R is a sulfonamino substituent, for example, a C$_{1-7}$alkyl group, a C$_{3-20}$heterocyclyl group, or a C$_{5-20}$aryl group, preferably a C$_{1-7}$alkyl group. Examples of sulfonamino groups include, but are not limited to, —NHS(=O)$_2$CH$_3$ and —N(CH$_3$)S(=O)$_2$C$_6$H$_5$.

Sulfinamino: —NR$^1$S(=O)R, wherein R$^1$ is an amino substituent, as defined for amino groups, and R is a sulfinamino substituent, for example, a C$_{1-7}$alkyl group, a C$_{3-20}$heterocyclyl group, or a C$_{5-20}$aryl group, preferably a C$_{1-7}$alkyl group. Examples of sulfinamino groups include, but are not limited to, —NHS(=O)CH$_3$ and —N(CH$_3$)S(=O)C$_6$H$_5$.

Sulfamyl: —S(=O)NR$^1$R$^2$, wherein R$^1$ and R$^2$ are independently amino substituents, as defined for amino groups. Examples of sulfamyl groups include, but are not limited to, —S(=O)NH$_2$, —S(=O)NH(CH$_3$), —S(=O)N(CH$_3$)$_2$, —S(=O)NH(CH$_2$CH$_3$), —S(=O)N(CH$_2$CH$_3$)$_2$, and —S(=O)NH Ph.

Sulfonamido: —S(=O)$_2$NR$^1$R$^2$, wherein R$^1$ and R$^2$ are independently amino substituents, as defined for amino groups. Examples of sulfonamido groups include, but are not limited to, —S(=O)$_2$NH$_2$, —S(=O)$_2$NH(CH$_3$), —S(=O)$_2$N(CH$_3$)$_2$, —S(=O)$_2$NH(CH$_2$CH$_3$), —S(=O)$_2$N(CH$_2$CH$_3$)$_2$, and —S(=O)$_2$NHPh.

In many cases, substituents are themselves substituted.

For example, a C$_{1-7}$alkyl group may be substituted with, for example:

hydroxy (also referred to as a hydroxy-C$_{1-7}$alkyl group);
halo (also referred to as a halo-C$_{1-7}$alkyl group);
amino (also referred to as a amino-C$_{1-7}$alkyl group);
carboxy (also referred to as a carboxy-C$_{1-7}$alkyl group);
C$_{1-7}$alkoxy (also referred to as a C$_{1-7}$alkoxy-C$_{1-7}$alkyl group);
C$_{5-20}$aryl (also referred to as a C$_{5-20}$aryl-C$_{1-7}$alkyl group).

Similarly, a C$_{5-20}$aryl group may be substituted with, for example:

hydroxy (also referred to as a hydroxy-C$_{5-20}$aryl group);
halo (also referred to as a halo-C$_{5-20}$aryl group);
amino (also referred to as an amino-C$_{5-20}$aryl group, e.g., as in aniline);
carboxy (also referred to as an carboxy-C$_{5-20}$aryl group, e.g., as in benzoic acid);

$C_{1-7}$alkyl (also referred to as a $C_{1-7}$alkyl-$C_{5-20}$aryl group, e.g., as in toluene);

$C_{1-7}$alkoxy (also referred to as a $C_{1-7}$alkoxy-$C_{5-20}$aryl group, e.g., as in anisole);

$C_{5-20}$aryl (also referred to as a $C_{5-20}$aryl-$C_{5-20}$aryl, e.g., as in biphenyl).

These and other specific examples of such substituted-substituents are described below.

Hydroxy-$C_{1-7}$alkyl: The term "hydroxy-$C_{1-7}$alkyl," as used herein, pertains to a $C_{1-7}$alkyl group in which at least one hydrogen atom (e.g., 1, 2, 3) has been replaced with a hydroxy group. Examples of such groups include, but are not limited to, —$CH_2OH$, —$CH_2CH_2OH$, and —$CH(OH)CH_2OH$.

Halo-$C_{1-7}$alkyl group: The term "halo-$C_{1-7}$alkyl," as used herein, pertains to a $C_{1-7}$alkyl group in which at least one hydrogen atom (e.g., 1, 2, 3) has been replaced with a halogen atom (e.g., F, Cl, Br, I). If more than one hydrogen atom has been replaced with a halogen atom, the halogen atoms may independently be the same or different. Every hydrogen atom may be replaced with a halogen atom, in which case the group may conveniently be referred to as a $C_{1-7}$per haloalkyl group." Examples of such groups include, but are not limited to, —$CF_3$, —$CHF_2$, —$CH_2F$, —$CCl_3$, —$CBr_3$, —$CH_2CH_2F$, —$CH_2CHF_2$, and —$CH_2CF_3$.

Amino-$C_{1-7}$alkyl: The term "amino-$C_{1-7}$alkyl," as used herein, pertains to a $C_{1-7}$alkyl group in which at least one hydrogen atom (e.g., 1, 2, 3) has been replaced with an amino group. Examples of such groups include, but are not limited to, —$CH_2NH_2$, —$CH_2CH_2NH_2$, and —$CH_2CH_2N(CH_3)_2$.

Carboxy-$C_{1-7}$alkyl: The term "carboxy-$C_{1-7}$alkyl," as used herein, pertains to a $C_{1-7}$alkyl group in which at least one hydrogen atom (e.g., 1, 2, 3) has been replaced with a carboxy group. Examples of such groups include, but are not limited to, —$CH_2COOH$ and —$CH_2CH_2COOH$.

$C_{1-7}$alkoxy-$C_{1-7}$alkyl: The term "$C_{1-7}$alkoxy-$C_{1-7}$alkyl," as used herein, pertains to a $C_{1-7}$alkyl group in which at least one hydrogen atom (e.g., 1, 2, 3) has been replaced with a $C_{1-7}$alkoxy group. Examples of such groups include, but are not limited to, —$CH_2OCH_3$, —$CH_2CH_2OCH_3$, and, —$CH_2CH_2OCH_2CH_3$ $C_{5-20}$aryl-$C_{1-7}$alkyl: The term "$C_{5-20}$aryl-$C_{1-7}$alkyl," as used herein, pertains to a $C_{1-7}$alkyl group in which at least one hydrogen atom (e.g., 1, 2, 3) has been replaced with a $C_{5-20}$aryl group. Examples of such groups include, but are not limited to, benzyl (phenylmethyl, $PhCH_2$—), benzhydryl ($Ph_2CH$—), trityl (triphenylmethyl, $Ph_3C$—), phenethyl (phenylethyl, $Ph-CH_2CH_2$—), styryl ($Ph-CH=CH$—), cinnamyl ($Ph-CH=CH-CH_2$—).

Hydroxy-$C_{5-20}$aryl: The term "hydroxy-$C_{5-20}$aryl," as used herein, pertains to a $C_{5-20}$aryl group in which at least one hydrogen atom (e.g., 1, 2, 3) has been substituted with an hydroxy group. Examples of such groups include, but are not limited to, those derived from: phenol, naphthol, pyrocatechol, resorcinol, hydroquinone, pyrogallol, phloroglucinol.

Halo-$C_{5-20}$aryl: The term "halo-$C_{5-20}$aryl," as used herein, pertains to a $C_{5-20}$aryl group in which at least one hydrogen atom (e.g., 1, 2, 3) has been substituted with a halo (e.g., F, Cl, Br, I) group. Examples of such groups include, but are not limited to, halophenyl (e.g., fluorophenyl, chlorophenyl, bromophenyl, or iodophenyl, whether ortho-, meta-, or para-substituted), dihalophenyl, trihalophenyl, tetrahalophenyl, and pentahalophenyl.

$C_{1-7}$alkyl-$C_{5-20}$aryl: The term "$C_{1-7}$alkyl-$C_{5-20}$aryl," as used herein, pertains to a $C_{5-20}$aryl group in which at least one hydrogen atom (e.g., 1, 2, 3) has been substituted with a $C_{1-7}$alkyl group. Examples of such groups include, but are not limited to, tolyl (from toluene), xylyl (from xylene), mesityl (from mesitylene), and cumenyl (or cumyl, from cumene), and duryl (from durene).

Hydroxy-$C_{1-7}$alkoxy: —OR, wherein R is a hydroxy-$C_{1-7}$alkyl group. Examples of hydroxy-$C_{1-7}$alkoxy groups include, but are not limited to, —$OCH_2OH$, —$OCH_2CH_2OH$, and —$OCH_2CH_2CH_2OH$.

Halo-$C_{1-7}$alkoxy: —OR, wherein R is a halo-$C_{1-7}$alkyl group. Examples of halo-$C_{1-7}$alkoxy groups include, but are not limited to, —$OCF_3$, —$OCHF_2$, —$OCH_2F$, —$OCCl_3$, —$OCBr_3$, —$OCH_2CH_2F$, —$OCH_2CHF_2$, and —$OCH_2CF_3$.

Carboxy-$C_{1-7}$alkoxy: —OR, wherein R is a carboxy-$C_{1-7}$alkyl group. Examples of carboxy-$C_{1-7}$alkoxy groups include, but are not limited to, —$OCH_2COOH$, —$OCH_2CH_2COOH$, and —$OCH_2CH_2CH_2COOH$.

$C_{1-7}$alkoxy-$C_{1-7}$alkoxy: —OR, wherein R is a $C_{1-7}$alkoxy-$C_{1-7}$alkyl group. Examples of $C_{1-7}$alkoxy-$C_{1-7}$alkoxy groups include, but are not limited to, —$OCH_2OCH_3$, —$OCH_2CH_2OCH_3$, and —$OCH_2CH_2OCH_2CH_3$.

$C_{5-20}$aryl-$C_{1-7}$alkoxy: —OR, wherein R is a $C_{5-20}$aryl-$C_{1-7}$alkyl group. Examples of such groups include, but are not limited to, benzyloxy, benzhydryloxy, trityloxy, phenethoxy, styryloxy, and cimmamyloxy.

$C_{1-7}$alkyl-$C_{5-20}$aryloxy: —OR, wherein R is a $C_{1-7}$alkyl-$C_{5-20}$aryl group. Examples of such groups include, but are not limited to, tolyloxy, xylyloxy, mesityloxy, cumenyloxy, and duryloxy.

Amino-$C_{1-7}$alkyl-amino: The term "amino-$C_{1-7}$alkyl-amino," as used herein, pertains to an amino group, —$NR^1R^2$, in which one of the substituents, $R^1$ or $R^2$, is itself a amino-$C_{1-7}$alkyl group (—$C_{1-7}$alkyl-$NR^3R^4$). The amino-$C_{1-7}$alkylamino group may be represented, for example, by the formula —$NR^1$—$C_{1-7}$alkyl-$NR^3R^4$. Examples of such groups include, but are not limited to, groups of the formula —$NR^1(CH_2)_nNR^1R^2$, where n is 1 to 6 (for example, —$NHCH_2NH_2$, —$NH(CH_2)_2NH_2$, —$NH(CH_2)_3NH_2$, —$NH(CH_2)_4NH_2$, —$NH(CH_2)_5NH_2$, —$NH(CH_2)_6NH_2$), —$NHCH_2NH(Me)$, —$NH(CH_2)_2NH(Me)$, —$NH(CH_2)_3NH(Me)$, —$NH(CH_2)_4NH(Me)$, —$NH(CH_2)_5NH(Me)$, —$NH(CH_2)_6NH(Me)$, —$NHCH_2NH(Et)$, —$NH(CH_2)_2NH(Et)$, —$NH(CH_2)_3NH(Et)$, —$NH(CH_2)_4NH(Et)$, —$NH(CH_2)_5NH(Et)$, and —$NH(CH_2)_6NH(Et)$.

Includes Other Forms

Unless otherwise specified, included in the above are the well known ionic, salt, solvate, and protected forms of these substituents. For example, a reference to carboxylic acid (—COOH) also includes the anionic (carboxylate) form (—$COO^-$), a salt or solvate thereof, as well as conventional protected forms. Similarly, a reference to an amino group includes the protonated form (—$N^+HR^1R^2$), a salt or solvate of the amino group, for example, a hydrochloride salt, as well as conventional protected forms of an amino group. Similarly, a reference to a hydroxyl group also includes the anionic form (—$O^-$), a salt or solvate thereof, as well as conventional protected forms of a hydroxyl group.

Isomers, Salts, Solvates, Protected Forms, and Prodrugs

Certain compounds may exist in one or more particular geometric, optical, enantiomeric, diastereomeric, epimeric, stereoisomeric, tautomeric, conformational, or anomeric forms, including but not limited to, cis- and trans-forms; E- and Z-forms; c-, t-, and r- forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —$OCH_3$, is not to be construed as a reference to its structural isomer, a hydroxymethyl group, —$CH_2OH$. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

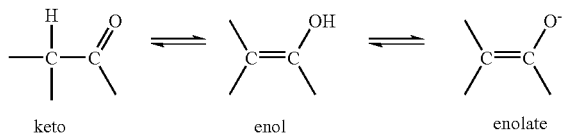

keto    enol    enolate

Note that specifically included in the term "isomer" are compounds with one or more isotopic substitutions. For example, H may be in any isotopic form, including $^1H$, $^2H$ (D), and $^3H$ (T); C may be in any isotopic form, including $^{12}C$, $^{13}C$, and $^{14}C$; O may be in any isotopic form, including $^{16}O$ and $^{18}O$; F may be in any isotopic form, including $^{18}F$ and $^{19}F$; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting the methods taught herein, or known methods, in a known manner.

Unless otherwise specified, a reference to a particular compound also includes ionic, salt, solvate, and protected forms of thereof, for example, as discussed below.

It may be convenient or desirable to prepare, purify, and/or handle a corresponding salt of the active compound, for example, a pharmaceutically-acceptable salt. Examples of pharmaceutically acceptable salts are discussed in Berge et al., 1977, "Pharmaceutically Acceptable Salts," *J. Pharm. Sci.*, Vol. 66, pp. 1-19.

For example, if the compound is anionic, or has a functional group which may be anionic (e.g., —COOH may be —$COO^-$), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations such as $Al^{+3}$. Examples of suitable organic cations include, but are n6t limited to, ammonium ion (i.e., $NH_4^+$) and substituted ammonium ions (e.g., $NH_3R^+$, $NH_2R_2^+$, $NHR_3^+$, $NR^{4+}$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is $N(CH_3)_4^+$.

If the compound is cationic, or has a functional group which may be cationic (e.g., —$NH_2$ may be —$NH_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, gycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, and valeric. Examples of suitable polymeric organic anions include, but are not limited to, those derived from the following polymeric acids: tannic acid, carboxymethyl cellulose.

It may be convenient or desirable to prepare, purify, and/or handle a corresponding solvate of the active compound. The term "solvate" is used herein in the conventional sense to refer to a complex of solute (e.g., active compound, salt of active compound) and solvent. If the solvent is water, the solvate may be conveniently referred to as a hydrate, for example, a mono-hydrate, a di-hydrate, a tri-hydrate, etc.

It may be convenient or desirable to prepare, purify, and/or handle the active compound in a chemically protected form. The term "chemically protected form" is used herein in the conventional chemical sense and pertains to a compound in which one or more reactive functional groups are protected from undesirable chemical reactions under specified conditions (e.g., pH, temperature, radiation, solvent, and the like). In practice, well known chemical methods are employed to reversibly render unreactive a functional group, which otherwise would be reactive, under specified conditions. In a chemically protected form, one or more reactive functional groups are in the form of a protected or protecting group (also known as a masked or masking group or a blocked or blocking group). By protecting a reactive functional group, reactions involving other unprotected reactive functional groups can be performed, without affecting the protected group; the protecting group may be removed, usually in a subsequent step, without substantially affecting the remainder of the molecule. See, for example, *Protective Groups in Organic Synthesis* (T. Green and P. Wuts; 3rd Edition; John Wiley and Sons, 1999).

A wide variety of such "protecting," "blocking," or "masking" methods are widely used and well known in organic synthesis. For example, a compound which has two nonequivalent reactive functional groups, both of which would be reactive under specified conditions, may be derivatized to render one of the functional groups "protected," and therefore unreactive, under the specified conditions; so protected, the compound may be used as a reactant which has effectively only one reactive functional group. After the desired reaction (involving the other functional group) is complete, the protected group may be "deprotected" to return it to its original functionality.

For example, a hydroxy group may be protected as an ether (—OR) or an ester (—OC(═O)R), for example, as: a t-butyl ether; a benzyl, benzhydryl (diphenylmethyl), or trityl (triphenylmethyl) ether; a trimethylsilyl or t-butyldimethylsilyl ether; or an acetyl ester (—OC(═O)CH$_3$, —OAc).

For example, an aldehyde or ketone group may be protected as an acetal (R—CH(OR)$_2$) or ketal (R$_2$C(OR)$_2$), respectively, in which the carbonyl group (>C═O) is converted to a diether (>C(OR)$_2$), by reaction with, for example, a primary alcohol. The aldehyde or ketone group is readily regenerated by hydrolysis using a large excess of water in the presence of acid.

For example, an amine group may be protected, for example, as an amide (—NRCO—R) or a urethane (—NRCO—OR), for example, as: a methyl amide (—NHCO—CH$_3$); a benzyloxy amide (—NHCO—OCH$_2$C$_6$H$_5$, —NH-Cbz); as a t-butoxy amide (—NHCO—OC(CH$_3$)$_3$, —NH-Boc); a 2-biphenyl-2-propoxy amide (—NHCO—OC(CH$_3$)$_2$C$_6$H$_4$C$_6$H$_5$, —NH-Bpoc), as a 9-fluorenylmethoxy amide (—NH-Fmoc), as a 6-nitroveratryloxy amide (—NH-Nvoc), as a 2-trimethylsilylethyloxy amide (—NH-Teoc), as a 2,2,2-trichloroethyloxy amide (—NH-Troc), as an allyloxy amide (—NH-Alloc), as a 2-(phenylsulphonyl)ethyloxy amide (—NH-Psec); or, in suitable cases (e.g., cyclic amines), as a nitroxide radical (>N—O.).

For example, a carboxylic acid group may be protected as an ester for example, as: an C$_{1-7}$alkyl ester (e.g., a methyl ester; a t-butyl ester); a C$_{1-7}$haloalkyl ester (e.g., a C$_{1-7}$trihaloalkyl ester); a triC$_{1-7}$alkylsilyl—C$_{1-7}$alkyl ester; or a C$_{5-20}$aryl-C$_{1-7}$alkyl ester (e.g., a benzyl ester; a nitrobenzyl ester); or as an amide, for example, as a methyl amide.

For example, a thiol group may be protected as a thioether (—SR), for example, as: a benzyl thioether; an acetamidomethyl ether (—S—CH$_2$NHC(═O)CH$_3$).

It may be convenient or desirable to prepare, purify, and/or handle the active compound in the form of a prodrug. The term "prodrug," as used herein, pertains to a compound which, when metabolised (e.g., in vivo), yields the desired active compound. Typically, the prodrug is inactive, or less active than the active compound, but may provide advantageous handling, administration, or metabolic properties.

For example, some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

Examples of such metabolically labile esters include those of the formula —C(═O)OR wherein R is:
C$_{1-7}$alkyl
(e.g., -Me, -Et, -nPr, -iPr, -nBu, -sBu, -iBu, -tBu);
C$_{1-7}$aminoalkyl
(e.g., aminoethyl; 2-(N,N-diethylamino)ethyl; 2-(4-morpholino)ethyl); and
acyloxy-C$_{1-7}$alkyl
(e.g., acyloxymethyl;
acyloxyethyl;
pivaloyloxymethyl;
acetoxymethyl;
1-acetoxyethyl;

1-(1-methoxy-1-methyl)ethyl-carbonxyloxyethyl;
1-(benzoyloxy)ethyl; isopropoxy-carbonyloxymethyl;
1-isopropoxy-carbonyloxyethyl; cyclohexyl-carbonyloxymethyl;
1-cyclohexyl-carbonyloxyethyl;
cyclohexyloxy-carbonyloxymethyl;
1-cyclohexyloxy-carbonyloxyethyl;
(4-tetrahydropyranyloxy)carbonyloxymethyl;
1-(4-tetrahydropyranyloxy)carbonyloxyethyl;
(4-tetrahydropyranyl)carbonyloxymethyl; and
1-(4-tetrahydropyranyl)carbonyloxyethyl).

Also, some prodrugs are activated enzymatically to yield the active compound, or a compound which, upon further chemical reaction, yields the active compound. For example, the prodrug may be a sugar derivative or other glycoside conjugate, or may be an amino acid ester derivative.

Acronyms

For convenience, many chemical moieties are represented using well known abbreviations, including but not limited to, methyl (Me), ethyl (Et), n-propyl (nPr), iso-propyl (iPr), n-butyl (nBu), sec-butyl (sBu), iso-butyl (iBu), tert-butyl (tBu), n-hexyl (nHex), cyclohexyl (cHex), phenyl (Ph), biphenyl (biPh), benzyl (Bn), naphthyl (naph), methoxy (MeO), ethoxy (EtO), benzoyl (Bz), and acetyl (Ac).

For convenience, many chemical compounds are represented using well known abbreviations, including but not limited to, methanol (MeOH), ethanol (EtOH), iso-propanol (i-PrOH), methyl ethyl ketone (MEK), ether or diethyl ether (Et$_2$O), acetic acid (AcOH), dichloromethane (methylene chloride, DCM), acetonitrile (ACN), trifluoroacetic acid (TFA), dimethylformamide (DMF), tetrahydrofuran (THF), and dimethylsulfoxide (DMSO).

Synthesis

Several methods for the chemical synthesis of compounds of the present invention are described herein. These methods may be modified and/or adapted in known ways in order to facilitate the synthesis of additional compounds within the scope of the present invention.

Method A

General Method for the Synthesis of
1-Sulfonyl-1H-Indoles

Treatment of the appropriate 1-unsubstituted-1H-indole with the appropriate sulfonyl chloride compound (R—SO$_2$Cl), for example, in the presence of tetrabutylammonium hydrogensulfate (TBAHS), for example, in toluene, and aqueous sodium hydroxide, gives the corresponding 1-substituted 1H-indole. An example of such a method is described below.

For example, to a vigorously stirred solution of 1-unsubstituted-1H-indole (8.5 mmol) and tetrabutylammonium hydrogensulfate (TBAHS) (1.28 mmol) in toluene (25 mL) at 0° C. is added 50% aqueous sodium hydroxide (25 mL) and sulfonyl chloride compound (12.8 mmol). The resultant solution is stirred at room temperature for 16 hours. After this time, the organic layer is separated and washed with 1N HCl (2×25 mL), saturated aqueous NaHCO$_3$ (2×25 mL), water (25 mL), and brine (25 mL), and is dried over MgSO$_4$, and is evaporated to dryness to yield the desired 1-sulfonyl-1H-indole.

Scheme 1

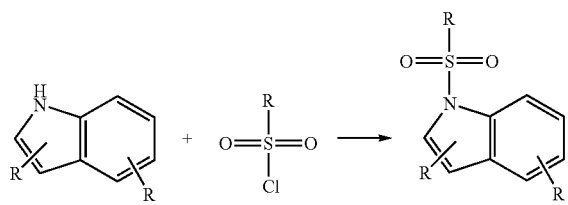

Method B

General Method for the Synthesis of 4,4-Dimethoxy-Cyclohexa-2,5-Dienones

Treatment of the appropriate 4-methoxyphenol with iodobenzene diacetate, for example, in methanol, under a nitrogen atmosphere, gives the corresponding 4,4-dimethoxy-cyclohexa-2,5-dienone. An example of such a method is described below.

For example, a solution of 4-methoxyphenol (40 mmol) and iodobenzene diacetate (14.3 g, 44 mmol) in methanol (150 mL) is stirred at 0° C., under a nitrogen atmosphere for 15 minutes. The solution is allowed to warm to room temperature and stirring is continued for 30 minutes. Solvent is removed in vacuo to yield the desired product.

Scheme 2

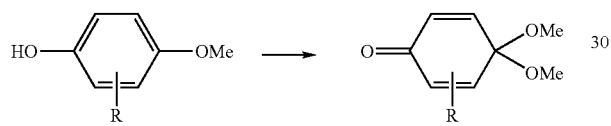

Method C

General Method for the Synthesis of 4-(1-Sulfonyl-1H-Indol-2-yl)-4-(Hydroxy)-Cyclohexa-2,5-Dieneones Treatment of the appropriate 1-sulfonyl-1H-indoles with n-butyl lithium, followed by the addition of the appropriate 4,4-dimethoxy-cyclohexa-2,5-dienone, gives the corresponding 4-(1-sulfonyl-1H-indol-2-yl)-4-(hydroxy)-cyclohexa-2,5-dieneone. An example of such a method is described below.

For example, to a stirring solution of n-butyl lithium (3.3 mL, 1.6 M in hexanes, 5.2 mmol) in tetrahydrofuran (THF) (7 mL) at −78° C. is added a solution of 1-sulphonyl-1H-indole (3.5 mmol) in THF (7 mL) dropwise, under a nitrogen atmosphere. Following addition, the solution is stirred at −78° C. for 1.5 hours. After this time, the resultant solution is added via cannular to a stirring solution of freshly prepared 4,4-dimethoxy-cyclohexa-2,5-dienone (0.54 g, 3.5 mmol) in THF (14 mL) at −78° C. Following addition, the solution is stirred at −78° C. for 2 hours. After this time, the resultant solution is poured into brine (25 mL) and extracted with $CH_2Cl_2$ (3×25 mL). The combined organic layer is washed with water (3×20 mL), brine (2×20 mL), and is dried over $MgSO_4$, and is filtered and evaporated to dryness. The dark oil is redissolved in acetone (20 mL) and 10% aqueous acetic acid (20 mL) and heated at reflux for 1 hour. After this time, the solution is allowed to cool to room temperature and extracted with $CH_2Cl_2$ (3×25 mL). The combined organic layer is washed with water (3×20 mL), brine (2×20 mL), and is dried over $MgSO_4$, filtered and evaporated to dryness. The product is purified by flash column chromatography (4:1 hexane:EtOAc) to yield the desired product.

Scheme 3

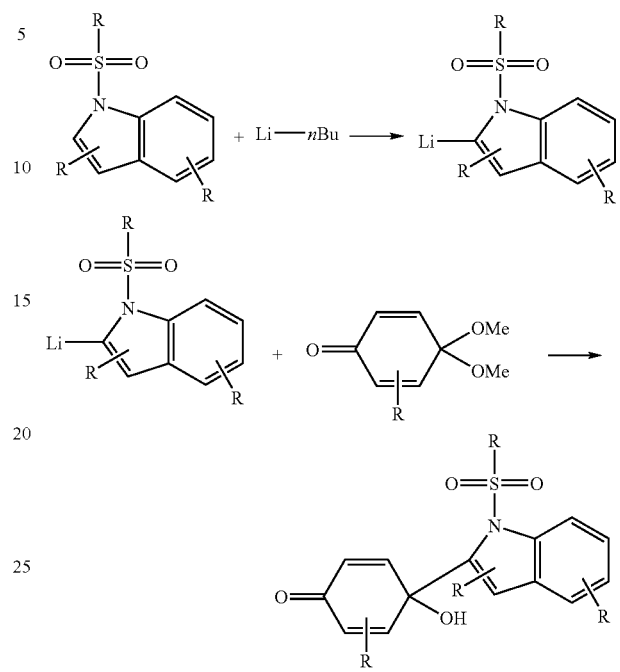

Method D

General Method for the Synthesis of 4,4-Dimethoxy-4H-Naphthalen-1-One

Treatment of the appropriate 4-methoxynaphthol with iodobenzene diacetate, for example, in methanol, under a nitrogen atmosphere, gives the corresponding 4,4-dimethoxy-4H-naphthalen-1-one. An example of such a method is described below.

For example, a solution of 4-methoxynaphthol (16 mmol) and iodobenzene diacetate (6.1 g, 19 mmol) in methanol (75 mL) is stirred at room temperature, under a nitrogen atmosphere for 1 hour. The resultant dark blue solution is poured into a saturated solution of $NaHCO_3$ (75 mL), then evaporated to reduced volume. The blue oil is extracted with $CH_2Cl_2$ (3×75 mL) and the organic layer is washed with water (3×75 mL), brine (2×75 mL), and is dried over $MgSO_4$, and filtered and evaporated to dryness (bath temp. <40° C.) to yield the product as a dark blue semi-solid.

Scheme 4

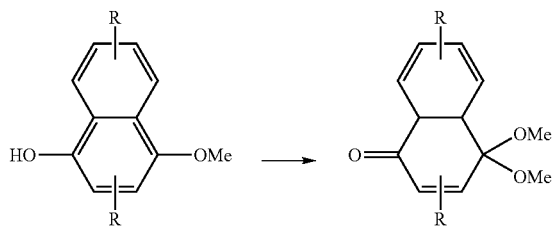

Method E

General Method for the Synthesis of 4-(1-Sulfonyl-1H-Indol-2-yl)-4-(Hydroxy)-Cyclohexa-2,5-Dieneones Treatment of the appropriate 1-sulfonyl-1H-indoles with n-butyl lithium, followed by the addition of the appropriate 4,4-dimethoxy-4H-naphthalen-1-one, gives the corresponding 4-(1-sulfonyl-1H-indol-2-yl)-4-(hydroxy)-4H-naphthalen-1-one. An example of such a method is described below.

For example, to a stirring solution of n-butyl lithium (3.3 mL, 1.6 M in hexanes, 5.2 mmol) in THF (7 mL) at −78° C. is added a solution of 1-sulphonyl-1H-indole (3.5 mmol) in THF (7 mL) dropwise, under a nitrogen atmosphere. Following addition, the solution is stirred at −78° C. for 1.5 hours. After this time, the resultant solution is added via cannular to a stirring solution of freshly prepared 4,4-dimethoxy-4H-naphthalen-1-one (3.5 mmol) in THF (14 mL) at −78° C. Following addition, the solution is stirred at −78° C. for 2 hours. After this time, the resultant solution is poured into brine (25 mL) and extracted with CH$_2$Cl$_2$ (3×25 mL). The combined organic layer is washed with water (3×20 mL), brine (2×20 mL), and dried over MgSO$_4$, and filtered and evaporated to dryness. The dark oil is redissolved in acetone (20 mL) and 10% aqueous acetic acid (20 mL) and heated at reflux for 1 hour. After this time, the solution is allowed to cool to room temperature and extracted with CH$_2$Cl$_2$ (3×25 mL). The combined organic layer is washed with water (3×20 mL), brine (2×20 mL), and dried over MgSO$_4$, and filtered and evaporated to dryness. The product is purified by flash column chromatography (4:1 hexane: EtOAc) to yield the desired product.

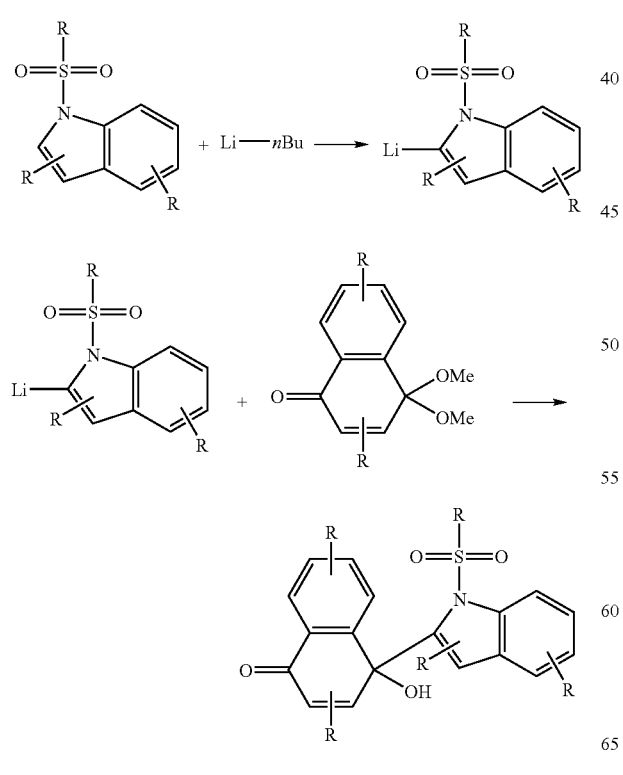

Scheme 5

Method F

General Method for Preparation of Substituted Arylsulfonyl Chlorides

Appropriate substituted arylsulfonyl chlorides, suitable for use in the above methods, may be prepared, for example, by reaction of the appropriate substituted aromatic compound with chlorosulfonic acid. An example of such a method is described below.

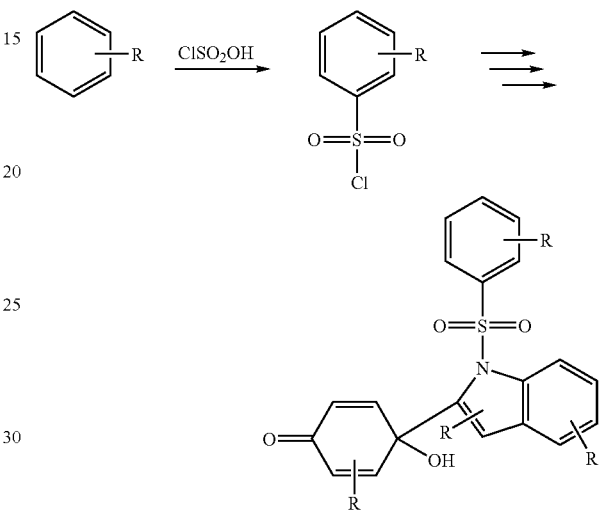

Scheme 6

Method G

General Method for Preparation of Oxy-Substituted Compounds

Oxy-substituted-sulfonyl compounds may be prepared from the corresponding methoxy compound. For example, the methoxy compound may be demethylated, e.g., with boron tribromide in methylene chloride, and the resulting hydroxy compound may be reacted with a suitable alkyl halide compound, including substituted alkyl halides, such as iodoacetic acid, to give the corresponding oxy-substituted-sulfonyl compound. An example of such a method is described below.

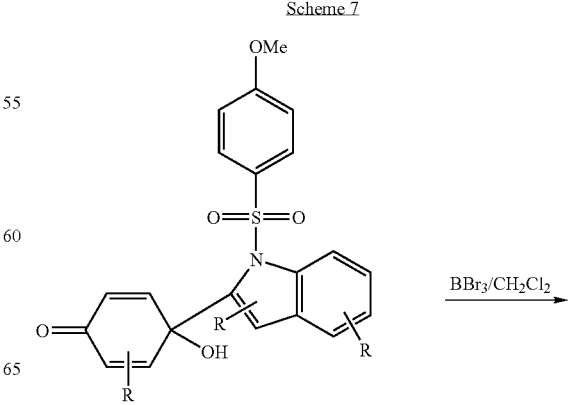

Scheme 7

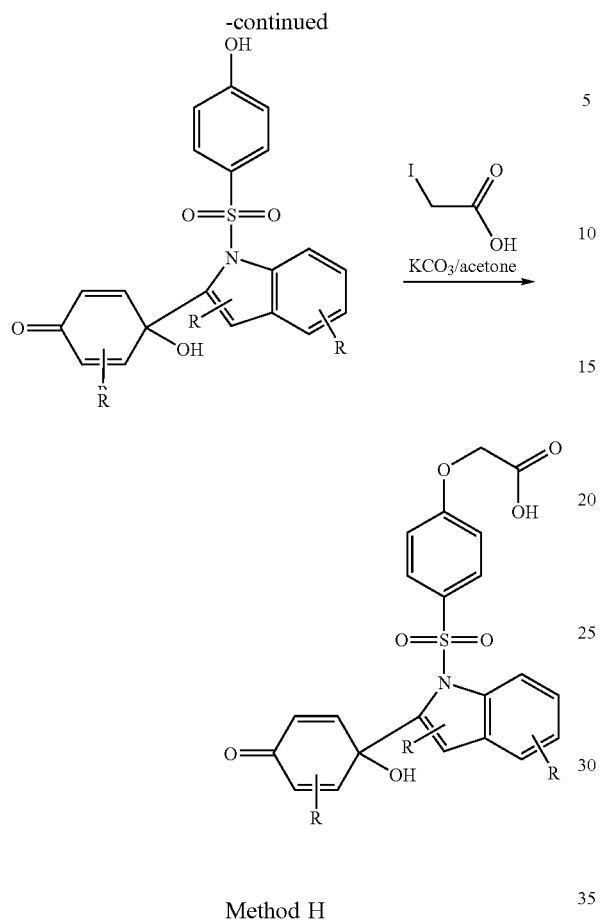

Method H

General Method for Preparation of Amino-Substituted Compounds

Amino-substituted-sulfonyl compounds may be prepared from the corresponding acetyl-amino compound, which may itself be prepared from commercially available acetylaminobenzene sulfonylchloride, using methods described above. For example, the acetyl-amino compound may converted to the free amino, e.g., by hydrolysis with hot dilute HCl, and the resulting hydroxy compound may be reacted with a suitable alkyl halide compound, including substituted alkyl halides, such as aminoalkyl iodide, to give the corresponding amino-substituted-sulfonyl compound. An example of such a method is described below.

Scheme 8

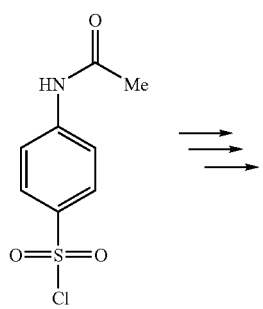

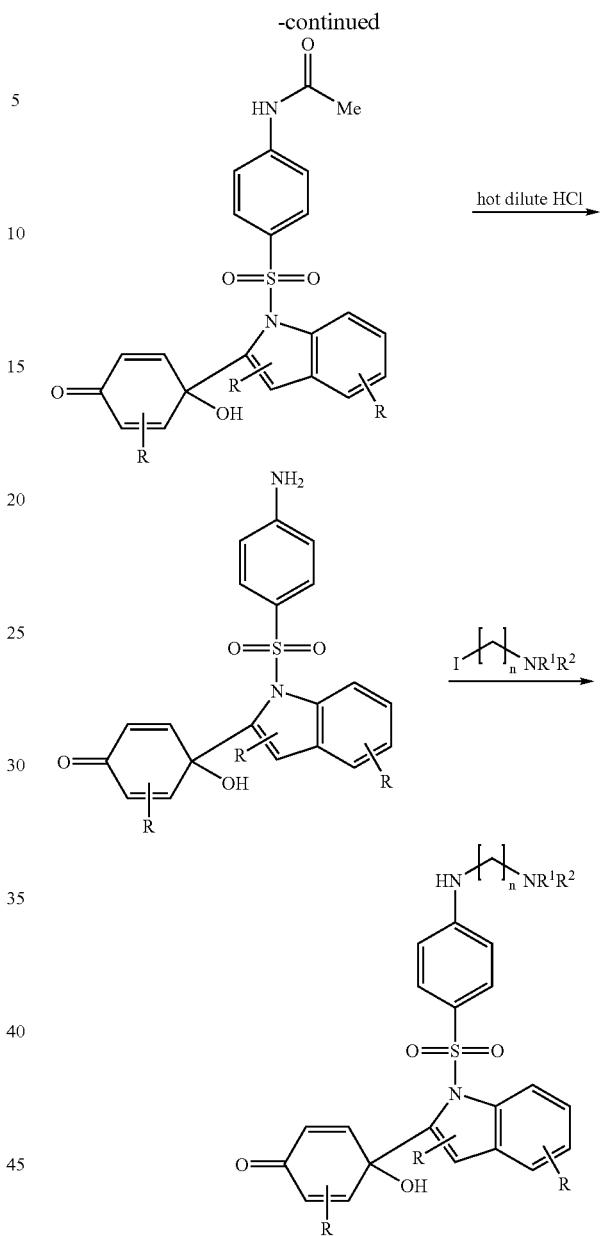

Method I

General Method for the Synthesis of bis-thiol Adducts

Treatment of the appropriate 1-sulfonyl-1H-indol-2-yl-quinol with the appropriate thiol (RSH), for example in ethanol in the presence of triethylamine, gives the corresponding di-thiol adduct. An example of such a method is described below.

To a solution of the quinol (0.1 g) in ethanol (5 mL) is added the thiol (2.0 equivalents) followed by triethylamine (0.1 equivalents). After two hours the solvent is removed under vacuum and the residue stirred with diethylether:hexane (1:1, 5 mL). The precipitate is collected on a filter and dried under vacuum.

Scheme 9

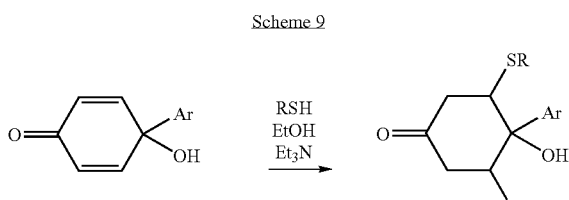

Method J

General Method for the Synthesis of mono-thiol Adducts

Treatment of the appropriate 1-sulfonyl-1H-indol-2-yl-quinol with the appropriate thiol (RSH), for example in ethanol, gives the corresponding mono-thiol adduct. An example of such a method is described below.

To a solution of the quinol (0.1 g) in ethanol (5 mL) was added the thiol (2.0 equivalents). After two hours the solvent was removed under vacuum and the residue dissolved in diethylether (1 mL) and purified by column chromatography (silica gel, EtOAc:hexane 2:8).

jScheme 10

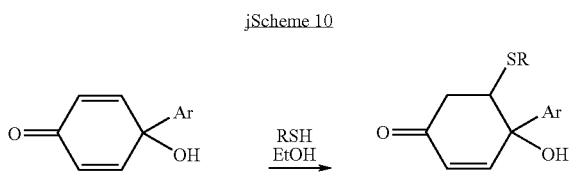

Uses

The present invention provides active compounds, specifically, active antiproliferative agents, anticancer agents, and/or thioredoxin/thioredoxin reductase inhibitors.

The term "active," as used herein, pertains to compounds which are capable of, e.g., inhibiting cell proliferation, treating cancer, inhibiting thioredoxin/thioredoxin reductase, and specifically includes both compounds with intrinsic activity (drugs) as well as prodrugs of such compounds, which prodrugs may themselves exhibit little or no intrinsic activity.

One of ordinary skill in the art is readily able to determine whether or not a candidate compound is active. For example, assays which may conveniently be used in order to assess the activity offered by a particular compound are described in the examples below.

Antiproliferative Applications

The present invention also provides active compounds which (a) regulate (e.g., inhibit) cell proliferation; (b) inhibit cell cycle progression; (c) promote apoptosis; or (d) a combination of one or more of these.

Thus, the present invention also provides methods of (a) regulating (e.g., inhibiting) cell proliferation; (b) inhibiting cell cycle progression; (c) promoting apoptosis; or (d) a combination of one or more of these, in vitro or in vivo, comprising contacting a cell with (e.g., exposing a cell to) an effective amount of an active compound, as described herein.

One of ordinary skill in the art is readily able to determine whether or not a candidate compound regulate (e.g., inhibit) cell proliferation, etc. For example, assays which may conveniently be used to assess the activity offered by a particular compound are described in the examples below.

For example, a sample of cells (e.g., from a tumour) may be grown in vitro and an active compound brought into contact with said cells, and the effect of the compound on those cells observed. As an example of "effect," the morphological status of the cells (e.g., alive or dead, etc.) may be determined. Where the active compound is found to exert an influence on the cells, this may be used as a prognostic or diagnostic marker of the efficacy of the compound in methods of treating a patient carrying cells of the same cellular type.

The present invention further provides antiproliferative agents. The term "antiproliferative agent" as used herein, pertains to a compound which treats a proliferative condition (i.e., a compound which is useful in the treatment of a proliferative condition).

One of ordinary skill in the art is readily able to determine whether or not a candidate compound treats a proliferative condition for any particular cell type. For example, assays which may conveniently be used to assess the activity offered by a particular compound are described in the examples below.

The terms "cell proliferation," "proliferative condition," "proliferative disorder," and "proliferative disease," are used interchangeably herein and pertain to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g., lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreas cancer, brain cancer, sarcoma, osteosarcoma, Kaposi's sarcoma, melanoma), leukemias, psoriasis, bone diseases, fibroproliferative disorders (e.g., of connective tissues), and atherosclerosis.

In one embodiment, the proliferative condition is colon cancer or renal cancer.

In one embodiment, the proliferative condition is colon cancer.

In one embodiment, the proliferative condition is renal cancer.

In one embodiment, the proliferative condition is melanoma.

Any type of cell may be treated, including but not limited to, lung, gastrointestinal (including, e.g., bowel, colon), breast (mammary), ovarian, prostate, liver (hepatic), kidney (renal), bladder, pancreas, brain, and skin.

In one embodiment, the cell is a colon cell (e.g., colon tumour cell, colon cancer cell) or a renal cell (e.g., renal tumour cell, renal cancer cell).

In one embodiment, the cell is a colon cell (e.g., colon tumour cell, colon cancer cell).

In one embodiment, the cell is a renal cell (e.g., renal tumour cell, renal cancer cell).

In one embodiment, the cell is a melanoma cell.

Anticancer Applications

Antiproliferative compounds of the present invention have application in the treatment of cancer, and so the present invention further provides anticancer agents.

The term "anticancer agent" as used herein, pertains to a compound which treats a cancer (i.e., a compound which is useful in the treatment of a cancer).

One of ordinary skill in the art is readily able to determine whether or not a candidate compound treats a cancerous condition for any particular cell type. For example, assays which may conveniently be used to assess the activity offered by a particular compound are described in the examples below.

The anti-cancer effect may arise through one or more mechanisms, including but not limited to, the regulation of cell proliferation, the inhibition of cell cycle progression, the inhibition of angiogenesis (the formation of new blood vessels), the inhibition of metastasis (the spread of a tumour from its origin), the inhibition of invasion (the spread of tumour cells into neighbouring normal structures), or the promotion of apoptosis (programmed cell death).

Thioredoxin/Thioredoxin Reductase Applications

The present invention also provides active compounds which inhibit thioredoxin/thioredoxin reductase activity.

The term "inhibiting thioredoxin/thioredoxin reductase," as used herein, includes: inhibiting thioredoxin/thioredoxin reductase activity; inhibiting the formation of thioredoxin/thioredoxin reductase complexes; and inhibiting the activity of thioredoxin/thioredoxin reductase complexes.

One of ordinary skill in the art is readily able to determine whether or not a candidate compound inhibits thioredoxin/thioredoxin reductase activity. For example, one assay which may conveniently be used in order to assess the thioredoxin/thioredoxin reductase inhibition offered by a particular compound is described in the examples below.

Thus, the present invention also provides methods of inhibiting thioredoxin/thioredoxin reductase in a cell, comprising contacting said cell with (e.g., exposing said cell to) an effective amount of an active compound. Such a method may be practised in vitro or in vivo. In one embodiment, the method is performed in vitro. In one embodiment, the method is performed in vivo. Preferably, the active compound is provided in the form of a pharmaceutically acceptable composition.

The present invention also provides active compounds which are anti-thioredoxin/thioredoxin reductase agents, and which treat a condition mediated by thioredoxin/thioredoxin reductase.

The term "a condition mediated by thioredoxin/thioredoxin reductase," as used herein pertains to a condition in which thioredoxin/thioredoxin reductase and/or the action of thioredoxin/thioredoxin reductase is important or necessary, e.g., for the onset, progress, expression, etc. of that condition, or a condition which is known to be treated by thioredoxin/thioredoxin reductase inhibitors.

The thioredoxins are ubiquitous proteins containing a conserved -Trp-Cys-Gly-Pro-Cys-Lys- redox catalytic site. Mammalian thioredoxin family members include thioredoxin-1 (Trx1), mitochondrial thioredoxin-2 (Trx2), and a larger thioredoxin-like protein, p32$^{TrxL}$. Thioredoxin is reduced by NADPH and thioredoxin reductase and, in turn reduces oxidized cysteine groups on proteins. When thioredoxin levels are elevated there is increased cell growth and resistance to the normal mechanism of programmed cell death. An increase in thioredoxin levels seen in many human primary cancers compared to normal tissue appears to contribute to increased cancer cell growth and resistance to chemotherapy. Mechanisms by which thioredoxin increases cell growth include an increased supply of reducing equivalents for DNA synthesis, activation of transcription factors that regulate cell growth, and an increase in the sensitivity of cells to other cytokines and growth factors. The mechanisms for the inhibition of apoptosis by thioredoxin are just now being elucidated. Because of its role in stimulating cancer cell growth and as an inhibitor of apoptosis, thioredoxin offers a target for the development of drugs to treat and prevent cancer. See, for example, the review article by Powis et al., 2000, and references cited therein.

Thioredoxin was first described in 1964 as a small redox protein from *Escherichia coli*. Mammalian thioredoxin was reported in 1967 as a redox protein present in rat Novikoff hepatoma cells. Thioredoxin was subsequently rediscovered under other names, including: (i) adult T cell leukemia-derived factor (ADF), an interleukin-2 (IL-2) receptor-inducing factor produced by human T-lymphotrophic virus type 1 (HTLV 1)-infected T cells; and, (ii) early pregnancy factor, part of a complex in the serum of pregnant animals that increases the complement-dependent inhibition of lymphocyte binding to heterologous blood cells. These proteins were shown to be identical when the correct predicted amino acid sequence of thioredoxin was published, and they are all now referred to as thioredoxin (Trx). A truncated form of thioredoxin, eosinophil cytotoxicity enhancing factor, has also been described.

Members of the thioredoxin family of proteins have as a conserved catalytic site -Trp-Cys-Gly-Pro-Cys-Lys- that undergoes reversible oxidation to the cysteine-disulfide (Trx-$S_2$) form through the transfer of reducing equivalents to a disulfide substrate (X—$S_2$). The oxidized thioredoxin is reduced back to the cysteine-thiol form [Trx-$(SH)_2$] by the NADPH-dependent flavoprotein thioredoxin reductase (TR).

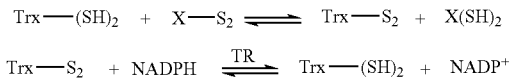

Mammalian thioredoxin reductases are homodimeric, flavin adenine dinucleotide-containing proteins with a penultimate C-terminal selenocysteine (SeCys) residue. The conserved redox catalytic site of thioredoxin reductase, -Cys-Val-Asn-Val-Gly-Cys-, undergoes reversible oxidation reduction in much the same way as thioredoxin. Although selenocysteine is essential for the full activity of mammalian thioredoxin reductases, human thioredoxin can be relatively efficiently reduced by the nonselenocysteine-containing bacterial thioredoxin reductase. To date, two human thioredoxin reductases have been cloned, TR1, found predominantly in the cytosol, and TR2, which has a putative mitochondrial import sequence.

Two forms of thioredoxin have been cloned, thioredoxin-1 (Trx-1) and thioredoxin 2 (Trx-2). Human Trx-1 is a 104 amino acid protein with a molecular weight of 12 kDa that contains two catalytic site Cys residues -Trp-Cys$^{32}$-Gly-Pro-Cys$^{35}$-Lys- found in all thioredoxin proteins, as well as three additional Cys residues, Cys$^{62}$, Cys$^{69}$, and Cys$^{73}$, that are not found in bacterial thioredoxins. Trx-1's from a number of other mammalian species, including chicken, rat, mouse, and bovine, have been cloned.

Thioredoxin variously acts as a growth factor, and antioxidant, a cofactor, as a transcription factor regulator, and as an inhibitor of apoptosis.

Studies with a variety of human primary tumors have shown that thioredoxin is overexpressed in the tumor compared to levels in the corresponding normal tissue. Recent immunohistochemical studies using paraffin-embedded tissue sections have shown that thioredoxin expression is increased in more than half of human primary gastric cancers. The thioredoxin levels showed a highly significant positive correlation (p<0.001) with cell proliferation measured by nuclear proliferation antigen and a highly significant negative correlation (p<0.001) with apoptosis measured by the terminal deoxynucleotidyl transferase assay. A comparison of 49,000 human gene transcripts in human normal colon epithelium and colorectal cancer by the serial analysis of gene expression (SAGE) technique revealed 548 differentially expressed transcripts. Thioredoxin mRNA was increased 2-fold in colon cancer cell lines and 4-fold in colon tumors.

Plasma and serum levels of thioredoxin, which in normal individuals are between 10 and 80 ng/ml (0.86.6 nM), have been reported to be elevated almost 2-fold in patients with hepatocellular carcinoma and to decrease following surgical removal of the tumor. Serum thioredoxin was not elevated in patients with other forms of liver disease such as chronic hepatitis or liver cirrhosis.

The growth-stimulating and transforming effects of thioredoxin, together with the finding that it is overexpressed by a number of human primary tumors, raise the possibility that thioredoxin is a factor leading to aggressive tumor growth and poor patient prognosis. Because thioredoxin has also been shown to inhibit apoptosis caused by a number of anticancer drugs and to be a cause of resistance to the cytotoxic effects of some anticancer drugs, it is possible that increased thioredoxin could be a cause of resistance to chemotherapy. These findings make thioredoxin an attractive target for the development of drugs to inhibit cancer cell growth. Several such compounds have been identified. They include PX-12 (1-methylhydroxypropyl 2-imidazoloyl disulfide), which was identified as an inhibitor of thioredoxin binding to the $Cys^{73}$ residue. The median $IC_{50}$ for growth inhibition of a variety of cell lines by PX-12 is 8.1 µM. PX-12 has been shown to have in vivo antitumor activity against human tumor xenografts in scid mice and chemopreventive activity in min (multiple intestinal neoplasia) mice, which have a germline mutation in the APC gene seen in familial adenomatous polyposis. The growth inhibition by compound PX-12 in the NCI 60 human tumor cell line panel was significantly correlated with the expression of thioredoxin mRNA. Several other inhibitors of thioredoxin have been identified by the COMPARE program from over 50,000 compounds tested by the National Cancer Institute as having a pattern of cell killing activity in the 60 human tumor cell line panel similar to PX-12. One of these compounds, NSC-131233 (2,5-bis[(dimethylamino)methyl] cyclopentanone) is an irreversible inhibitor of thioredoxin with a $K_I$ of 1.0 µM.

The thioredoxins are a family of small redox proteins whose functions include the regulation of cell growth, programmed cell death, and the development of the organism. When thioredoxin levels are elevated in cells, there is increased cell growth and resistance to normal mechanisms of programmed cell death. An increase in thioredoxin levels seen in many human primary cancers compared to normal tissue may be a contributing factor leading to increased cancer cell growth and resistance to chemotherapeutic drugs. The mechanism for the increase in thioredoxin in cancer cells remains unknown at this time. Because of its role as a stimulator of cell growth and an inhibitor of apoptosis, thioredoxin is a target for the development of drugs to treat and, possibly, prevent cancer.

Methods of Treatment, Etc.

The invention further provides methods of treatment for example, of a proliferative condition, cancer, a condition mediated by thioredoxin/thioredoxin reductase, a condition known to be treated by thioredoxin/thioredoxin reductase inhibitors, or other condition as described herein, comprising administering to a subject in need of treatment a therapeutically-effective amount of an active compound, preferably in the form of a pharmaceutical composition.

The invention further provides active compounds for use in a method of treatment of the human or animal body, for example, in the treatment of a proliferative condition, cancer, a condition mediated by thioredoxin/thioredoxin reductase, a condition known to be treated by thioredoxin/thioredoxin reductase inhibitors, or other condition as described herein.

The invention further provides the use of an active compound for the manufacture of a medicament, for example, for the treatment of a proliferative conditions, cancer, a condition mediated by thioredoxin/thioredoxin reductase, a condition known to be treated by thioredoxin/ thioredoxin reductase inhibitors, or other condition as described herein.

Treatment

The term "treatment," as used herein in the context of treating a condition, pertains generally to treatment and therapy, whether of a human or an animal (e.g., in veterinary applications), in which some desired therapeutic effect is achieved, for example, the inhibition of the progress of the condition, and includes a reduction in the rate of progress, a halt in the rate of progress, amelioration of the condition, and cure of the condition. Treatment as a prophylactic measure (i.e., prophylaxis) is also included.

The term "therapeutically-effective amount," as used herein, pertains to that amount of an active compound, or a material, composition or dosage form comprising an active compound, which is effective for producing some desired therapeutic effect, commensurate with a reasonable benefit risk ratio.

The term "treatment" includes combination treatments and therapies, in which two or more treatments or therapies are combined, for example, sequentially or simultaneously. Examples of treatments and therapies include, but are not limited to, chemotherapy (the administration of active agents, including, e.g., drugs, antibodies (e.g., as in immunotherapy), prodrugs (e.g., as in photodynamic therapy, GDEPT, ADEPT, etc.); surgery; radiation therapy; and gene therapy.

For example, in one embodiment, the treatment is combination treatment employing a compound as described herein, with cisplatin.

Active compounds may also be used, as described above, in combination therapies, that is, in conjunction with other agents, for example, cytotoxic agents.

Additional Uses

Active compounds may also be used as cell culture additives to inhibit thioredoxin/thioredoxin reductase, for example, in order to regulate cell proliferation in vitro.

Active compounds may also be used as part of an in vitro assay, for example, in order to determine whether a candidate host is likely to benefit from treatment with the compound in question.

Active compounds may also be used as a standard, for example, in an assay, in order to identify other active compounds, other antiproliferative agents, anticancer agents, thioredoxin/thioredoxin reductase inhibitors, etc.

Kits

One aspect of the invention pertains to a kit comprising (a) the active ingredient, preferably provided in a suitable container and/or with suitable packaging; and (b) instructions for use, for example, written instructions about how to administer the active compound.

The written instructions may also include a list of indications for which the active ingredient is a suitable treatment.

Routes of Administration

The active compound or pharmaceutical composition comprising the active compound may be administered to a subject by any convenient route of administration, whether systemically/peripherally or topically (i.e., at the site of desired action).

Routes of administration include, but are not limited to, oral (e.g, by ingestion); buccal; sublingual; transdermal (including, e.g., by a patch, plaster, etc.); transmucosal (including, e.g., by a patch, plaster, etc.); intranasal (e.g., by nasal spray); ocular (e.g., by eyedrops); pulmonary (e.g., by inhalation or insufflation therapy using, e.g., via an aerosol, e.g., through the mouth or nose); rectal (e.g., by suppository or enema); vaginal (e.g., by pessary); parenteral, for example, by injection, including subcutaneous, intradermal, intramuscular, intravenous, intraarterial, intracardiac, intrathecal, intraspinal, intracapsular, subcapsular, intraorbital, intraperitoneal, intratracheal, subcuticular, intraarticular, subarachnoid, and intrastemal; by implant of a depot or reservoir, for example, subcutaneously or intramuscularly.

The Subject

The subject may be a prokaryote (e.g., bacteria) or a eukaryote (e.g., protoctista, fungi, plants, animals).

The subject may be an animal, a mammal, a placental mammal, a marsupial (e.g., kangaroo, wombat), a monotreme (e.g., duckbilled platypus), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

Furthermore, the subject may be any of its forms of development, for example, a spore, a seed, an egg, a larva, a pupa, or a foetus.

Formulations

While it is possible for the active compound to be administered alone, it is preferable to present it as a pharmaceutical formulation (e.g., composition, preparation, medicament) comprising at least one active compound, as defined above, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. The formulation may further comprise other active agents, for example, other therapeutic or prophylactic agents.

Thus, the present invention further provides pharmaceutical compositions, as defined above, and methods of making a pharmaceutical composition comprising admixing at least one active compound, as defined above, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable" as used herein pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

Suitable carriers, diluents, excipients, etc. can be found in standard pharmaceutical texts, for example, *Remington's Pharmaceutical Sciences,* 18th edition, Mack Publishing Company, Easton, Pa., 1990; and *Handbook of Pharmaceutical Excipients,* 2nd edition, 1994.

The formulations may be prepared by any methods well known in the art of pharmacy. Such methods include the step of bringing into association the active compound with a carrier +which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations may suitably be in the form of liquids, solutions (e.g., aqueous, non-aqueous), suspensions (e.g., aqueous, non-aqueous), emulsions (e.g., oil-in-water, water-in-oil), elixirs, syrups, electuaries, mouthwashes, drops, tablets (including, e.g., coated tablets), granules, powders, losenges, pastilles, capsules (including, e.g., hard and soft gelatin capsules), cachets, pills, ampoules, boluses, suppositories, pessaries, tinctures, gels, pastes, ointments, creams, lotions, oils, foams, sprays, mists, or aerosols.

Formulations may suitably be provided as a patch, adhesive plaster, bandage, dressing, or the like which is impregnated with one or more active compounds and optionally one or more other pharmaceutically acceptable ingredients, including, for example, penetration, permeation, and absorption enhancers. Formulations may also suitably be provided in a the form of a depot or reservoir.

The active compound may be dissolved in, suspended in, or admixed with one or more other pharmaceutically acceptable ingredients. The active compound may be presented in a liposome or other microparticulate which is designed to target the active compound, for example, to blood components or one or more organs.

Formulations suitable for oral administration (e.g, by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Formulations suitable for buccal administration include mouthwashes, losenges, pastilles, as well as patches, adhesive plasters, depots, and reservoirs. Losenges typically comprise the active compound in a flavored basis, usually sucrose and acacia or tragacanth. Pastilles typically comprise the active compound in an inert matrix, such as gelatin and glycerin, or sucrose and acacia. Mouthwashes typically comprise the active compound in a suitable liquid carrier.

Formulations suitable for sublingual administration include tablets, losenges, pastilles, capsules, and pills.

Formulations suitable for oral transmucosal administration include liquids, solutions (e.g., aqueous, non-aqueous), suspensions (e.g., aqueous, non-aqueous), emulsions (e.g., oil-in-water, water-in-oil), mouthwashes, losenges, pastilles, as well as patches, adhesive plasters, depots, and reservoirs.

Formulations suitable for non-oral transmucosal administration include liquids, solutions (e.g., aqueous, non-aqueous), suspensions (e.g., aqueous, non-aqueous), emulsions (e.g., oil-in-water, water-in-oil), suppositories, pessaries, gels, pastes, ointments, creams, lotions, oils, as well as patches, adhesive plasters, depots, and reservoirs.

Formulations suitable for transdermal administration include gels, pastes, ointments, creams, lotions, and oils, as well as patches, adhesive plasters, bandages, dressings, depots, and reservoirs.

Tablets may be made by conventional means, e.g., compression or molding, optionally with one or more accessory ingredients. Compressed tablets may be prepared by compressing in a suitable machine the active compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Molded tablets may be made by molding in a suitable machine a mixture of the powdered compound moistened with an inert liquid diluent. The tablets may optionally be coated or scored and may be formulated so as to provide slow or controlled release of the active compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Ointments are typically prepared from the active compound and a paraffinic or a water-miscible ointment base.

Creams are typically prepared from the active compound and an oil-in-water cream base. If desired, the aqueous phase of the cream base may include, for example, at least about 30% w/w of a polyhydric alcohol, i.e., an alcohol having two or more hydroxyl groups such as propylene glycol, butane-1,3-diol, mannitol, sorbitol, glycerol and polyethylene glycol and mixtures thereof. The topical formulations may desirably include a compound which enhances absorption or penetration of the active compound through the skin or other affected areas. Examples of such dermal penetration enhancers include dimethylsulfoxide and related analogues.

Emulsions are typically prepared from the active compound and an oily phase, which may optionally comprise merely an emulsifier (otherwise known as an emulgent), or it may comprises a mixture of at least one emulsifier with a fat or an oil or with both a fat and an oil. Preferably, a hydrophilic emulsifier is included together with a lipophilic emulsifier which acts as a stabiliser. It is also preferred to include both an oil and a fat. Together, the emulsifier(s) with or without stabiliser(s) make up the so-called emulsifying wax, and the wax together with the oil and/or fat make up the so-called emulsifying ointment base which forms the oily dispersed phase of the cream formulations.

Suitable emulgents and emulsion stabilisers include Tween 60, Span 80, cetostearyl alcohol, myristyl alcohol, glyceryl monostearate and sodium lauryl sulphate. The choice of suitable oils or fats for the formulation is based on achieving the desired cosmetic properties, since the solubility of the active compound in most oils likely to be used in pharmaceutical emulsion formulations may be very low. Thus the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for intranasal administration, where the carrier is a liquid, include, for example, nasal spray, nasal drops, or by aerosol administration by nebuliser, include aqueous or oily solutions of the active compound.

Formulations suitable for intranasal administration, where the carrier is a solid, include, for example, those presented as a coarse powder having a particle size, for example, in the range of about 20 to about 500 microns which is administered in the manner in which snuff is taken, i.e., by rapid inhalation through the nasal passage from a container of the powder held close up to the nose.

Formulations suitable for pulmonary administration (e.g., by inhalation or insufflation therapy) include those presented as an aerosol spray from a pressurised pack, with the use of a suitable propellant, such as dichlorodifluoromethane, trichlorofluoromethane, dichoro-tetrafluoroethane, carbon dioxide, or other suitable gases.

Formulations suitable for ocular administration include eye drops wherein the active compound is dissolved or suspended in a suitable carrier, especially an aqueous solvent for the active compound.

Formulations suitable for rectal administration may be presented as a suppository with a suitable base comprising, for example, natural or hardened oils, waxes, fats, semi-liquid or liquid polyols, for example, cocoa butter or a salicylate; or as a solution or suspension for treatment by enema.

Formulations suitable for vaginal administration may be presented as pessaries, tampons, creams, gels, pastes, foams or spray formulations containing in addition to the active compound, such carriers as are known in the art to be appropriate.

Formulations suitable for parenteral administration (e.g., by injection), include aqueous or non-aqueous, isotonic, pyrogen-free, sterile liquids (e.g., solutions, suspensions), in which the active compound is dissolved, suspended, or otherwise provided (e.g., in a liposome or other microparticulate). Such liquids may additional contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active compound in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the active compounds, and compositions comprising the active compounds, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 µg to about 100 mg per kilogram body weight of the subject per day. Where the active compound is a salt, an ester, an amide, a prodrug, or the like, the amount administered is calculated on the basis of the parent compound and so the actual weight to be used is increased proportionately.

EXAMPLES

The following are examples are provided solely to illustrate the present invention and are not intended to limit the scope of the invention, as described herein.

All compounds were characterised by elemental microanalysis (C, H, and N values within 0.4% of theoretical values). Melting points were determined using a Gallenkamp melting point apparatus and are reported uncorrected. $^1$H and $^{13}$C NMR spectra were recorded using a Bruker ARX250 spectrometer. IR spectra (as KBr discs) were determined using a Mattson 2020 Galaxy series FT-IR spectrophotometer. Mass spectra were recorded on an AEI MS-902 or a VG Micromass 7070E spectrometer. TLC systems for routine monitoring of reaction mixtures, and for confirming the homogeneity of analytical samples used Kieselgel 60F$_{254}$ (0.25 mm) silica gel TLC aluminum sheets. Sorbsil silica gel C 60-H (40-60 µm) was used for flash chromatographic separations. All reactions were carried out under inert atmosphere using anhydrous reagents and solvents. Tetrahydrofuran (THF) was dried and purified before use by distillation from sodium-benzophenone. All other commerical materials were used as received.

Example 1

1-benzenesulfonyl-5-methoxy-1H-indole

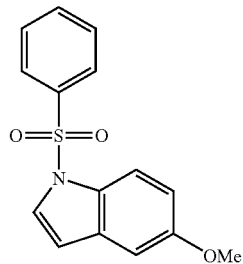

The title compound was prepared from benzene sulfonyl chloride and 5-methoxy-1H-indole, according to Method A, described above. Yield 67%; mp 73-75° C.; $^1$H NMR (CDCl$_3$) δ 7.55-7.82 (m, 3H), 7.41-7.48 (m, 2H), 7.31-7.37 (m, 2H), 6.83-6.90 (m, 2), 6.51-6.52 (dd, J=4 Hz, 1H); $^{13}$C NMR (CDCl$_3$) δ 156.9, 138.6, 134.2, 132.2, 129.9, 129.6, 127.5, 127.1, 114.8, 114.2, 109.8, 104.1, 56.0; MS (ES$^+$) m/z 287.99 (M$^+$+1).

Example 2

1-benzenesulfonyl-5-fluoro-1H-indole

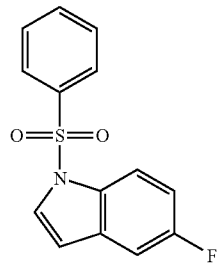

The title compound was prepared from benzene sulfonyl chloride and 5-fluoro-1H-indole, according to Method A, described above. Yield 73%; $^1$H NMR (CDCl$_3$) δ 7.77-7.82 (dd, J=9 Hz, 1H), 7.71-7.74 (m, 2H), 7.47 (d, J=4 Hz, 1H), 7.30-7.45 (m, 3H), 7.03-7.07 (dd, J=9 Hz, 1H), 6.87-6.95 (dt, J=9 Hz, 1H), 6.51 (d, J=4 Hz, 1H); MS (AP$^+$) m/z 276.0 (M$^+$+1), 214.

Example 3

1-(toluene-4-sulfonyl)-1H-indole

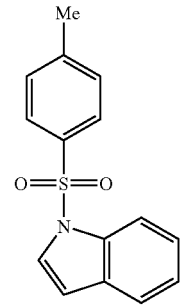

The title compound was prepared from toluene-4-sulfonyl chloride and 1H-indole, according to Method A, described above. Yield 91%; mp 60-62° C.; $^1$H NMR (CDCl$_3$) δ 8.0-8.03 (dd, J=8 Hz, 1H), 7.78 (d, J=7 Hz, 2H), 7.57 (d, J=4 Hz, 1H), 7.52-7.56 (m, 1H), 7.26-7.36 (m, 2H), 7.20-7.23 (d, J=8 Hz, 2H), 6.66-6.68 (dd, J=4 Hz, 1H), 2.30 (s, 3H); $^{13}$C NMR (CDCl$_3$) δ 145.4, 135.7, 135.3, 131.2, 130.3, 127.2, 126.8, 124.9, 123.7, 121.8, 113.9, 109.5, 21.9; MS (ES$^+$) m/z 271.93 (M$^+$).

Example 4

1-(4-methoxy-benzenesulfonyl)-1H-indole

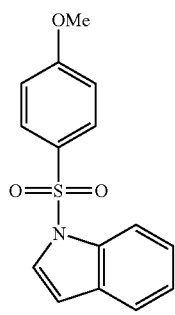

The title compound was prepared from 4-methoxy-benzene sulfonyl chloride and 1H-indole, according to Method A, described above. Yield 95%; mp 124-126° C.; $^1$H NMR (CDCl$_3$) δ 7.90-7.93 (dd, J=8 Hz, 1H), 7.74 (d, J=9 Hz, 2H), 7.43-7.49 (m, 2H), 7.14-7.27 (m, 2H), 6.79 (d, J=9 Hz, 2H), 6.56-6.58 (dd, J=4 Hz, 1H), 3.41 (s, 3H); $^{13}$C NMR (CDCl$_3$) δ 164.1, 135.2, 131.2, 130.1, 129.5, 126.7, 124.9, 123.6, 121.8, 114.8, 113.9, 109.3, 56.0; MS (AP$^+$) m/z288.05 (M$^+$+1).

Example 5

1-(4-fluoro-benzenesulfonyl)-1H-indole

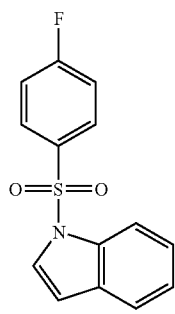

The title compound was prepared from 4-fluoro-benzene sulfonyl chloride and 1H-indole, according to Method A, described above. Yield 81%; mp 135-137° C.; $^1$H NMR (CDCl$_3$) δ 7.86-7.99 (m, 3H), 7.51-7.54 (m, 2H), 7.19-7.35 (m, 2H), 7.05-7.12 (m, 2H), 6.66-6.68 (dd, J=4 Hz, 1H); $^{13}$C NMR (CDCl$_3$) δ 168.1, 164.0, 135.2, 134.7, 134.6, 131.2, 130.1, 129.9, 126.6, 125.2, 123.9, 121.9, 117.2, 116.9, 113.9, 110.0; MS (ES$^+$) m/z 275.99 (M$^+$+1).

Example 6

1-(naphthalene-2-sulfonyl)-1H-indole

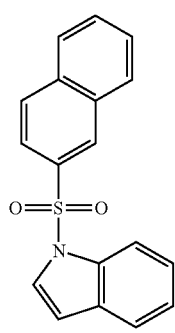

The title compound was prepared from naphthalene-2-sulfonyl chloride and 1H-indole, according to Method A, described above. Yield 92%; mp 103-105° C.; $^1$H NMR (CDCl$_3$) δ 8.33-8.34 (m, 1H), 7.85-7.89 (dd, J=8 Hz, 1H), 7.69-7.76 (m, 1H), 7.52-7.64 (m, 3H), 7.29-7.46 (m, 4H), 6.97-7.24 (m, 2H), 6.46-6.48 (dd, J=4 Hz, 1H); $^{13}$C NMR (CDCl$_3$) δ 135.6, 135.5, 135.3, 132.3, 131.2, 130.1, 129.8, 128.9, 128.3, 128.2, 126.8, 125.1, 123.8, 121.9, 121.8, 113.9, 109.7; MS (AP$^+$) m/z 308.04 (M$^+$+1).

Example 7

5-fluoro-1-(toluene-4-sulfonyl)-1H-indole

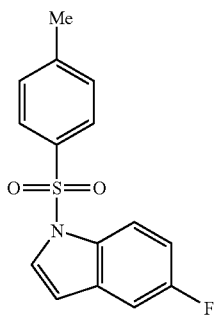

The title compound was prepared from toluene-4-sulfonyl chloride and 5-fluoro-1H-indole, according to Method A, described above. Yield 100%; mp 106-108° C.; $^1$H NMR (CDCl$_3$) δ 8.13-8.19 (dd, J=4, 8 Hz, 1H), 7.96 (d, J=8 Hz, 2H), 7.82 (d, J=4 Hz, 1H), 7.40-7.48 (m, 3H), 7.25-77.38 (m,1H), 6.83 (d, J=4 Hz, 1H), 2.55 (s, 3H); $^{13}$C NMR (CDCl$_3$) δ 161.9, 158.1, 145.6, 135.4, 132.2, 132.1, 131.6, 130.3, 128.5, 127.2, 115.0, 114.9, 113.2, 112.8, 109.4, 109.3, 107.5, 107.1, 21.9.

Example 8

1-(2,4,6-Triisopropyl-benzenesulfonyl)-1H-indole

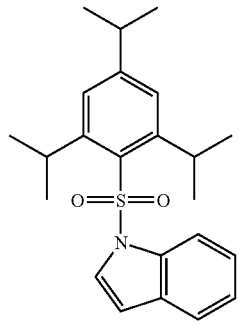

The title compound was prepared from 2,4,6-triisopropyl-benzene sulfonyl chloride and 1H-indole, according to Method A, described above. Yield 88%; mp 131-133° C.; $^1$H NMR (CDCl$_3$) δ 7.41-7.65 (m, 3H), 7.18-7.28 (m, 4H), 6.65-6.68 (dd, J=8 Hz, 1H), 4.15-4.31 (m, 2H), 2.81-2.97 (m, 1H), 1.28 and 1.29 (2s, 6H), 0.98-1.12 (m, 12H).

Example 9

4,4-dimethoxy-cyclohexa-2,5-dienone

The title compound was prepared from 4-methoxyphenol, according to Method B, described above, to give a pale orange oil, which solidified at 0° C. Yield 94%; $^1$H NMR (CDCl$_3$) δ 6.8 (d, J=12 Hz, 2H), 6.3 (d, J=12 Hz, 2H), 3.33 (s, 6H).

Example 10

4-(1-benzenesulfonyl-1H-indol-2-yl)-4-hydroxy-cyclohexa-2,5-dienone

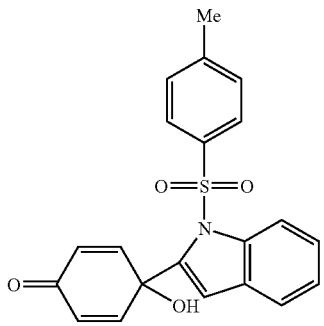

The title compound was prepared from 4,4-dimethoxy-cyclohexa-2,5-dienone and 1-benzenesulfonyl-1H-indole (available commercially), according to Method C, described above. Yield 18%; mp 170-172° C.; $^1$H NMR (CDCl$_3$) δ 8.0 (d, J=8 Hz, 1H), 7.87 (d, J=8 Hz, 2H), 7.51-7.60 (m, 3H), 7.30-7.46 (m, 3H), 7.18-7.27 (m, 2H), 6.80 (s, 1H), 6.32 (d, J=10 Hz, 2H), 5.50 (s, 1H); $^{13}$C NMR (CDCl$_3$) δ 185.3, 147.9, 141.2, 138.6, 137.8, 134.7, 129.7, 128.7, 128.1, 127.0, 126.6, 125.0, 122.1, 115.6, 114.1, 67.9.

Example 11

4-(1-benzenesulfonyl-5-methoxy-1H-indol-2-yl)-4-hydroxy-cyclohexa-2,5-dienone

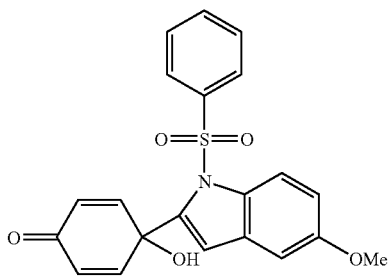

The title compound was prepared from 4,4-dimethoxy-cyclohexa-2,5-dienone and 1-benzenesulfonyl-5-methoxy-1H-indole, according to Method C, described above. Yield 32%; mp 126-128° C.; $^1$H NMR (CDCl$_3$) δ 7.73-7.83 (m, 3H), 7.40-7.49 (m, 2H), 7.33-7.40 (m, 2H), 6.76-6.84 (m, 3H), 6.64 (s, 1H), 6.20 (d, J=10 Hz, 2H), 5.40 (s, 1H), 3.67 (s, 3H); $^{13}$C NMR (CDCl$_3$) δ 196.6, 185.3, 157.3, 147.9, 141.8, 137.7, 134.3, 133.2, 129.8, 129.7, 129.3, 127.9, 126.9, 116.8, 115.4, 114.4, 104.2, 81.2, 67.9, 55.9; MS (AP$^+$) m/z 396.09 (M$^+$+1), 378.08.

Example 12

4-(1-benzenesulfonyl-5-fluoro-1H-indol-2-yl)-4-hydroxy-cyclohexa-2,5-dienone

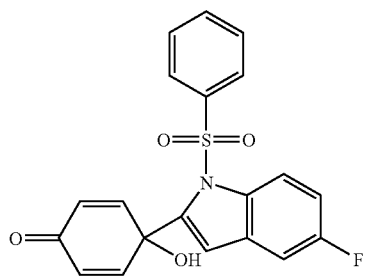

The title compound was prepared from 4,4-dimethoxy-cyclohexa-2,5-dienone and 1-benzenesulfonyl-5-fluoro-1H-indole, according to Method C, described above. Yield 21%; mp 166-167° C.; $^1$H NMR (CDCl$_3$) δ 8.03-8.09 (m, 1H), 7.94 (d, J=8 Hz, 2H), 7.51-7.70 (m, 5H), 7.12-7.20 (m, 2H), 6.86 (s, 1H), 6.42 (d, J=10 Hz, 2H), 5.49 (s, 1H); $^{13}$C NMR (CDCl$_3$) δ 185.1, 162.4, 158.5, 147.6, 143.0, 137.7, 134.8, 129.9, 129.8, 129.7, 128.2, 126.9, 116.9, 116.8, 114.8, 114.4, 113.6, 107.8, 107.4, 67.9; MS (AP$^+$) m/z 384.04 (M$^+$+1).

Example 13

4-(hydroxy4-[1-(toluene-4-sulfonyl)-1H-indol-2-yl]-cyclohexa-2,5-dienone

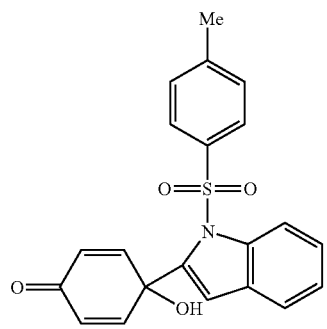

The title compound was prepared from 4,4-dimethoxy-cyclohexa-2,5-dienone and 1-(toluene-4-sulfonyl)-1H-indole, according to Method C, described above. Yield 12%; mp 159-161° C.; $^1$H NMR (CDCl$_3$) δ 7.90 (d, J=8 Hz, 1H), 7.65 (d, J=8 Hz, 2H), 7.48 (d, J=10 Hz, 2H), 7.33 (d, J=7 Hz,1H), 6.70-7.25 (m, 4H), 6.70 (s, 1H), 6.23 (d, J=Hz, 2H), 5.55 (s, 1H), 2.25 (s, 3H); $^{13}$C NMR (CDCl$_3$) δ 185.3, 148.0, 145.9, 141.2, 138.6, 134.9, 130.3, 128.7, 127.9, 127.0, 126.5, 124.9, 122.0, 116.6, 115.6, 113.9, 67.9, 21.9; MS (AP$^+$) m/z 380.04 (M$^+$+1).

Example 14

4-(hydroxy-4-[1-(4-methoxy-benzenesulfonyl)-1H-indol-2-yl]-cyclohexa-2,5-dienone

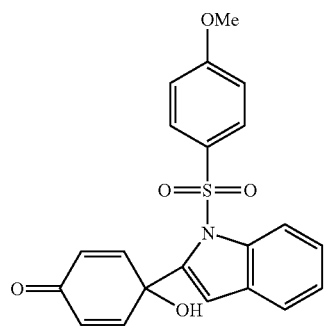

The title compound was prepared from 4,4-dimethoxy-cyclohexa-2,5-dienone and 1-(4-methoxy-benzenesulfonyl)-1H-indole, according to Method C, described above.

Yield 14%; mp 69-71° C.; $^1$H NMR (CDCl$_3$) δ 7.84-7.94 (m,1H), 7.73 (d, J=9 Hz, 2H), 7.49 (d, J=10 Hz, 2H), 7.13-7.40 (m, 3H), 6.73-6.86 (m, 2H), 6.69 (s, 1H), 6.23 (d, J=10 Hz, 2H), 5.51 (s, 1H), 3.70 (s, 3H); $^{13}$C NMR (CDCl$_3$) δ 185.3, 164.4, 149.2, 148.0, 141.1, 140.3, 138.6, 129.6, 129.2, 128.8, 126.3, 124.6, 121.9, 115.8, 114.7, 81.9, 72.5, 67.9, 58.1, 56.0, 38.8; MS (AP$^+$) m/z 396.03 (M$^+$+1).

Example 15

4-[1-(4-fluoro-benzenesulfonyl)-1H-indol-2-yl]-4-hydroxy-cyclohexa-2,5-dienone

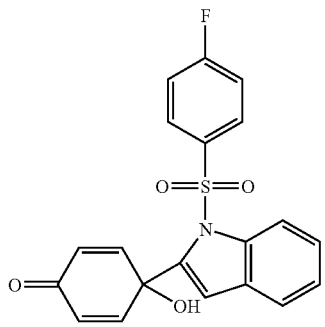

The title compound was prepared from 4,4-dimethoxy-cyclohexa-2,5-dienone and 1-(4-fluoro-benzenesulfonyl)-1H-indole, according to Method C, described above. Yield 14%; mp 165-166° C.; $^1$H NMR (CDCl$_3$) δ 7.82-7.93 (m, 3H), 7.49 (d, J=10 Hz, 2H), 7.35 (d, J=8 Hz, 1H), 7.12-7.28 (m, 2H), 6.99-7.05 (m, 2H), 6.73 (s, 1H), 6.25 (d, J=10 Hz, 2H), 5.31 (s, 1H); $^{13}$C NMR (CDCl$_3$) δ 185.2, 170.9, 170.5, 147.7, 141.0, 138.6, 133.6, 130.1, 129.9, 128.8, 128.1, 126.8, 125.2, 122.2, 117.3, 116.9, 115.6, 114.5, 69.5, 67.9; MS (AP$^+$) m/z 384.04 (M$^+$+1).

Example 16

4-(hydroxy-4-[1-(naphthalene-2-sulfonyl)-1H-indol-2-yl]-cyclohexa-2,5-dienone

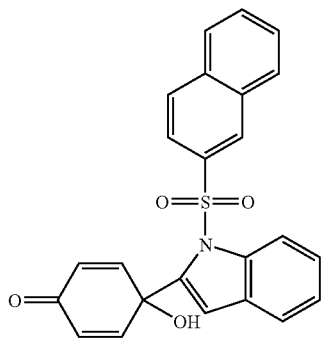

The title compound was prepared from 4,4-dimethoxy-cyclohexa-2,5-dienone and 1-(naphthalene-2-sulfonyl)-1H-indole, according to Method C, described above. Yield 14%; mp 66-69° C.; $^1$H NMR (CDCl$_3$) δ 8.42 (s, 1H), 7.96 (d, J=8 Hz, 1H), 7.84 (d, J=7 Hz,1H), 7.64-7.74 (m, 3H), 7.49-7.54 (m, 4H), 7.07-7.32 (m, 3H), 6.71 (s, 1H), 6.24 (d, J=10 Hz, 2H), 5.50 (s, 1H); $^{13}$C NMR (CDCl$_3$) δ 185.4, 150.0, 148.1, 141.3, 138.6, 135.7, 134.7, 132.0, 130.3, 130.1, 129.9, 129.3, 128.7, 128.4, 128.3, 128.0, 126.6, 124.9, 122.1, 121.3, 116.6, 115.6, 113.9, 68.0; MS (AP$^+$) m/z 416.07 (M$^+$+1).

Example 17

4-[5-fluoro-1-(toluene-4-sulfonyl)-1H-indol-2-yl]-4-hydroxy-cyclohexa-2,5-dienone

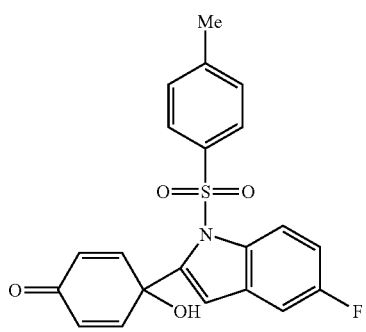

The title compound was prepared from 4,4-dimethoxy-cyclohexa-2,5-dienone and 1-benzenesulfonyl-5-fluoro-1H-indole, according to Method C, described above. Yield 58%; $^1$H NMR (CDCl$_3$) δ 7.85-7.90 (dd, J=4, 9 Hz, 1H), 7.65 (d, J=8 Hz, 2H), 7.47 (d, J=10 Hz, 2H), 7.15 (d, J=8 Hz, 2H), 6.91-7.02 (m, 2H), 6.66 (s, 1H), 6.25 (d, J=10 Hz, 2H), 5.42 (s, 1H), 2.28 (s, 3H); $^{13}$C NMR (CDCl$_3$) δ 185.2, 162.3, 158.4, 149.4, 147.8, 146.2, 142.9, 134.9, 134.6, 130.4, 129.9, 129.7, 128.6, 128.1, 127.0, 116.9, 116.8, 114.7, 114.3, 113.6, 113.5, 107.7, 107.4, 67.9, 22.0.

Example 18

4-[1-(2,4,6-triisopropyl-benzene-4-sulfonyl)-1H-indol-2-yl]-4-hydroxy-cyclohexa-2,5-dienone

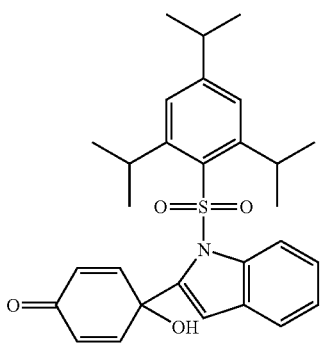

The title compound was prepared from 4,4-dimethoxy-cyclohexa-2,5-dienone and 1-(2,4,6-triisopropyl-benzene-sulfonyl-1H-indole, according to Method C, described above. Yield 12%; mp 55-57° C.; $^1$H NMR (CDCl$_3$) δ 7.37-7.47 (m, 3H), 6.92-7.09 (m, 5H), 6.70 (s, 2H), 6.25 (d, J=10 Hz, 2H), 5.41 (s, 1H), 3.73-3.78 (m, 2H), 2.70-2.91 (m, 1H), 1.15 and 1.18 (2s, 6H), 0.99-1.01 (m, 12H); $^{13}$C NMR (CDCl$_3$) δ 185.5, 155.4, 151.3, 148.4, 141.1, 137.8, 132.7, 127.8, 125.6, 124.8, 123.9, 121.9, 113.3, 111.1, 68.2, 34.6, 29.7, 24.7, 23.8; MS (AP$^+$) m/z 492.21 (M$^+$+1).

Example 19

4,4-dimethoxy-4H-naphthalen-1-one

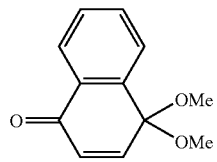

The title compound was prepared from 4-methoxynaphthol, according to Method D, described above. Yield 98%; $^1$H NMR (CDCl$_3$) δ 8.15 (d, J=8 Hz, 1H), 7.4-7.85 (m, 3H), 6.9 (d, J=12 Hz, 1H), 6.55 (d, J=12 Hz, 1H), 3.15 (s, 6H).

Example 20

4-(1-benzenesulfonyl-1H-indol-2-yl)-4-hydroxy4H-naphthalen-1-one

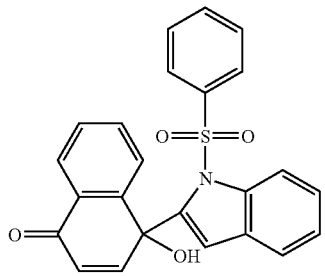

The title compound was prepared from 4,4-dimethoxy-4H-naphthalen-1-one and 1-benzenesulfonyl-1H-indole, according to Method E, described above. Yield 20%; mp 175-177° C.; $^1$H NMR (CDCl$_3$) δ 8.19-8.23 (dd, J=7 Hz, 1H), 8.02-8.05 (dd, J=9 Hz, 1H), 7.80-7.92 (m, 4H), 7.68-7.73 (t, J=7 Hz, 1H), 7.55-7.64 (m, 2H), 7.42-7.48 (t, J=7 Hz, 2H), 7.25-7.32 (m, 3H), 7.14-7.20 (m, 1H), 6.37 (d, J=11 Hz, 1H); $^{13}$C NMR (CDCl$_3$) δ 189.7, 153.9, 149.7, 148.9, 143.7, 143.2, 139.0, 137.9, 135.7, 134.2, 133.7, 133.6, 132.4, 131.6, 131.3, 130.8, 129.4, 126.7, 120.5, 74.9; MS (AP$^+$) m/z 416.07 (M$^+$+1), 398.06.

Example 21

4-hydroxy 4-[1-(toluene-4-sulfonyl)-1H-indol-2-yl]-4H-naphthalen-1-one

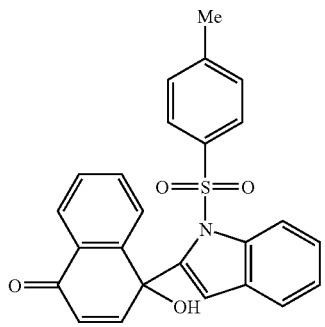

The title compound was prepared from 4,4-dimethoxy-4H-naphthalen-1-one and 1-(toluene4-sulfonyl)-1H-indole, according to Method E, described above. Yield 23%; mp 110-112° C.; $^1$H NMR (CDCl$_3$) δ 8.35-8.39 (dd, J=8 Hz, 1H), 8.04 (d, J=8 Hz,1H), 7.74-7.97 (m, 6H), 7.32-7.48 (m, 6H), 6.53 (d, J=10 Hz,1H), 2.52 (s, 3H); $^{13}$C NMR (CDCl$_3$) δ 189.7, 154.0, 150.2, 149.8, 148.8, 143.6, 140.1, 137.9, 135.7, 134.8, 133.6, 132.3, 131.7, 131.3, 130.7, 129.3, 126.6, 120.4, 120.3, 74.8, 26.6; MS (AP$^+$) m/z 430.09 (M$^+$+1), 412.14.

Biological Data

Compounds were assessed for their activity using various in vitro and in vivo assays, described below.

NCl Screening

Compounds were tested for in vitro activity (48 hour drug exposure) across 60 human cancer cell lines through the National Cancer Institute (NCl) Developmental Therapies Screening Program (Boyd et al., 1995). The mean growth inhibition (GI50) and cytotoxicity lethal concentration (LC$_{50}$) values are summarized in Table 1. Surprisingly and unexpectedly, many of the compounds had particular activity in colon and renal cell lines.

TABLE 1

Activity of Compounds In NCI in Vitro 60 Cell Panel

| Cmpd | mean log$_{10}$ GI$_{50}$ (µM)$^a$ | Mean log$_{10}$ LC$_{50}$ (µM)$^a$ | Most Senstive Cells Lines mean log$_{10}$ LC$_{50}$ (µM)$^a$ | |
|---|---|---|---|---|
| SIQ-01 | −7.41 | −5.53 | HCT-116: −7.48 | CAKI-1: −7.28 |
| SIQ-02 | −6.87 | −5.21 | ACHN: −6.35 | LOX IMVI: −6.33 |
| SIQ-03 | −7.18 | −5.49 | HCT-116: −7.30 | LOX IMVI: −7.20 |
| SIQ-04 | −6.95 | −5.14 | HCT-116: −7.32 | LOX IMVI: −6.63 |
| SIQ-05 | −6.79 | −5.20 | HCT-116: −6.95 | LOX IMVI: −6.42 |
| SIQ-06 | −6.63 | −5.11 | HCT-116: −6.44 | UO-31: −6.20 |
| SIQ-07 | −6.72 | −5.25 | HCT-116: −6.43 | U251: −6.29 |
| SIQ-08 | ND | ND | ND | ND |
| SIQ-09 | −6.37 | −4.95 | HCT-116: −6.26 | RXF 393: −6.11 |
| SIQ-10 | −6.35 | −5.11 | HCT-116: −6.10 | LOX IMVI: −6.11 |
| SIQ-11 | −6.41 | −5.25 | HCT-116: −6.31 | LOX IMVI: −6.14 |

$^a$For definitions of mean GI$_{50}$ and mean LC$_{50}$ see Boyd et al., 1995, and Weinstein et al., 1997.
ND = not done.
Colon: HCT-116.
Renal: CAKI-1, ACHN, RXF 393, UO-31.
Melanoma: LOX IMVI.
CNS Cancer: U251.

Growth Inhibitory Assay

Compounds were prepared as 10 mM top stocks, dissolved in DMSO, and stored at 4° C., protected from light, for a maximum period of 4 weeks. Human derived cell lines (HCT 116, HT29 colon carcinoma) were routinely cultivated at 37° C. in an atmosphere of 5% CO$_2$ in RPMI 1640 medium supplemented with 2 mM L-glutamine and 10% fetal calf serum and subcultured twice weekly to maintain continuous logarithmic growth. Cells were seeded into 96-well microtiter plates at a density of 5×10$^3$ per well and allowed 24 hours to adhere before drugs were introduced (final concentration 0.1 nM-100 µM, n=8). Serial drug dilutions were prepared in medium immediately prior to each assay. At the time of drug addition and following 72 hour exposure, MTT was added to each well (final concentration 400 g/mL). Incubation at 37° C. for 4 hr allowed reduction of MTT by mitochondrial dehydrogenase to an insoluble formazan product. Well contents were aspirated and formazan solubilized by addition of DMSO:glycine buffer (pH 10.5) (4:1). Absorbance was measured using an Anthos Labtec systems plate reader at 550 nm, and used as a measure of cell viability; thus cell growth or drug toxicity was determined. The results are summarised in Table 2.

TABLE 2

In Vitro Activity

| | | IC50 (μM) | |
|---|---|---|---|
| Compound | | HCT 116 | HT 29 |
| SIQ-01 | BW 114 | 0.086 | 0.259 |
| SIQ-03 | JMB 40.2 | 0.068 | 0.347 |
| SIQ-04 | JMB 69 | 0.036 | 0.206 |
| SIQ-05 | JMB 78 | 0.203 | 0.420 |
| SIQ-07 | JMB 79 | 0.193 | 0.274 |
| SIQ-10 | JMB 49 | 0.205 | 0.444 |
| SIQ-11 | JMB 68 | 0.155 | 0.391 |
| DMSO | — | >100 | >100 |

Thioredoxin Activity

Assays were performed using methods analogous to those described in Kirkpatrick et al., 1999 and Kunkel et al., 1997.

Thioredoxin (TR) (specific activity 43.6 μmol NADPH reduced/min/mg protein at 21° C.) was purified from human placenta as previously described (Oblong et al., 1993). Recombinant hTrx was expressed in *Escherichia coli* and purified as previously described (Gasdaska et al., 1994). The Trx and TR were stored at −20° C. with 5 mM dithiothreitol (DTT) which was removed before use with a desalting column (PDIO, Pharmacla, Uppsala, Sweden).

Microtitre plate colorimetric assays, based on the increase in absorbance at 405 nm which occurs as dithionitrobenzoic acid (DTNB) is reduced by the enzyme-mediated transfer of reducing equivalents from NADPH, were used to measure TR/Trx-dependent insulin-reduction and TR activity (see, e.g., Kunkel et al., 1997).

Thioredoxin reductase/thioredox independent insulin reducing activity was measured in an incubation with a final volume of 60 μL containing 100 mM HEPES buffer, pH 7.2, 5 mM EDTA (HE buffer), 1 mM NADPH, 1.0 μM thioredoxin reductase, 0.8 μM thioredoxin, and 2.5 mg/ml bovine insulin in flat-bottom 96-well microtitre plates. Compounds were diluted in HE buffer and added to the wells as 20 μL aliquots. Incubations were for 30 min at 37° C. The reaction was stopped by the addition of 100 μL of 6 M guanidine HCl, 50 mM Tris, pH 8.0, and 10 mM DTNB, and the absorbance measured at 405 nm.

Assays of TR activity were run in flat-bottom 96-well microtitre plates in a final incubation volume of 60 μL containing HE buffer, 10 mM DTNB, 1.0 μM thioredoxin reductase, and 1 mM NADPH. Compounds were diluted in HE buffer and added to the wells as aliquots. To ensure uniform coverage of the bottom of the well, the plate was briefly spun at 3000 g. To start the reaction, NADPH and DTNB were added as a 20 μL aliquots in HE buffer and the plate was moved to the plate reader preheated to 37° C. The optical density at 405 nm was measured every 10 s and initial linear reaction rates were determined. The data are summarised in Table 3.

TABLE 3

Inhibition of Thioredoxin/Thioredoxin Reductase (Tx/TR)-catalysed reduction of Insulin

| | | IC$_{50}$ (mM) | | Mean GI$_{50}$ |
|---|---|---|---|---|
| Compound | | Tx/TR | TR | (μM) |
| SIQ-01 | BW 114 | 0.152 | ND | 0.152 |
| SIQ-03 | JMB 40.2 | 0.527 | ND | 0.527 |
| SIQ-04 | JMB 69 | <0.1 | ND | <0.1 |
| SIQ-11 | JMB 68 | >1.0 | ND | >1.0 |

In Vivo Studies

The in vivo activity of SIQ-01 was studied. The maximum tolerated dose of SIQ-01 in mice is 30 mg/kg on a daily (×5) schedule. Combination treatment of SIQ-01 and cisplatin was active against the HCT116 colon carcinoma tumour when administered to tumour-bearing mice (15 mg SIC-01/kg administered by intraperitoneal injection on days 1-5 and 8-10; 4 mg cisplatin/kg administered subcutaneously on days 1 and 8), and gave a maximum T/C (Test/Control) of 49%. Treatment with cisplatin alone (same regimen) gave a maximum T/C (Test/Control) of 56%.

Without wishing to be bound to any particular theory, it is believed that thioredoxin is associated with resistance to cisplatin therapy, and that combination therapy with both a thioredoxin inhibitor (such as the compounds described herein) and cisplatin provides improved therapy, as compared to therapy with cisplatin alone. The in vivo studies describe above support this position.

The foregoing has described the principles, preferred embodiments, and modes of operation of the present invention. However, the invention should not be construed as limited to the particular embodiments discussed. Instead, the above-described embodiments should be regarded as illustrative rather than restrictive, and it should be appreciated that variations may be made in those embodiments by workers skilled in the art without departing from the scope of the present invention.

REFERENCES

A number of patents and publications are cited above in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Alcaraz, L., et al., 1998, "Manumycin A: synthesis of the (+)-enantiomer and revision of stereochemical assignment," *J. Org. Chem.*, Vol. 63, pp. 3526-3527.

Boyd, M. R., Paull, K. D., 1995, "Some practical considerations and applications of the National Cancer Institute in vitro anticancer drug discovery system," *Drug Dev. Res.*, Vol. 34, pp. 91-104.

Faaland et al., 1991, "Rapid uptake of tyrphostin into A431 human epidermoid cells is followed by delayed inhibition of epidermal growth factor (EGF) stimulated EFG receptor tyrosine kinase activity," *Mol. Cell Biol.*, Vol. 11, pp. 2697-2703.

Gasdaska et al., 1994, "The predicted amino acid sequence of human thioredoxin is identical to that of the autocrine growth factor human adult T-cell derived cofactor (ADF): thioredoxin mRNA is elevated in some human tumors," *Biochimica et Biophysica Acta*, Vol. 1218, p. 292.

Kirkpatrick et al., 1999, "Parallel synthesis of disulfide inhibitors of the thioredoxin redox system as potential antitumor agents," *Anti-Cancer Drug Design*, Vol. 14, pp. 421-432.

Kunkel et al., 1997, "Cell line-directed screening assay for inhibitors of thioredoxin reductase signaling as potential anti-cancer drugs," *Anti-Cancer Drug Design*, Vol. 12, pp. 659-670.

Milič, D. R., et al., "X-Ray crystal structure of 10β-hydroxy-4β,5β-epoxyestr-1-en-3,17-dione and antitumor activity of its congeners," *Molecules*, Vol. 4, pp. 338-352.

Oblong et al., 1993, "Purification of human thioreductase; properties and characterization by absorption and circular dichroism spectroscopy," *Biochemistry*, Vol. 32, p. 7271.

Powis, G., Mustacich, D, Coon, A., 2000, "The role of the redox protein thioredoxin in cell growth and cancer," Free Radical Biology & Medicine, Vol. 29, Nos. 3/4, pp. 312-322.

Rambas et al., 1994, "The degree of inhibition of protein tyrosine kinase activity by Tyrphostin 23 and 25 is related to their instability," Cancer Research, Vol 54, pp. 867-869.

Reddy et al., 1992, "Inhibition of breast cancer cell growth in vitro by a tyrosine kinase inhibitor," Cancer Research, Vol. 52, pp. 3631-3641.

Stevens, M. F. G., et al., 2003, "4-Aryl Quinols and Analogs Thereof as Therapeutic Agents," International (PCT) Patent Application number PCT/GB02/03097, publication number WO 03/004479, published 16 Jan. 2003.

Umezawa et al., 1991, "Use of erbstatin as protein tyrosine kinase inhibitor," Methods Enzymol., Vol. 201, pp. 379-385.

Wada, H., et al., 1987, "Chemical and chemotaxonomical studies of ferns. LXXIII. New flavonoids with modified B-ring from the genus Pseudophegopteris (Thelypteridacae)," Chem. Pharm. Bull., Vol. 35, pp. 4757-4762.

Weinstein, J. N., et al., 1997, "An information-intensive approach to the molecular pharmacology of cancer," Science, Vol. 275, pp. 343-349.

Wells et al., 6 Mar. 2000, "Antitumour benzothiazoles. Part 10: The synthesis and antitumour activity of benzothiazole substituted quinol derivatives," Bioorganic & Medicinal Chemistry Letters, Vol. 10, No. 5, pp. 513-515.

Wipf, P., et al., "Synthesis of the antitumor antibiotic LL-C10037α," J. Org. Chem., Vol. 59, pp. 3518-3519.

The invention claimed is:

1. A compound selected from compounds of the following formulae and pharmaceutically acceptable salts, esters, amides, solvates, and hydrates thereof:

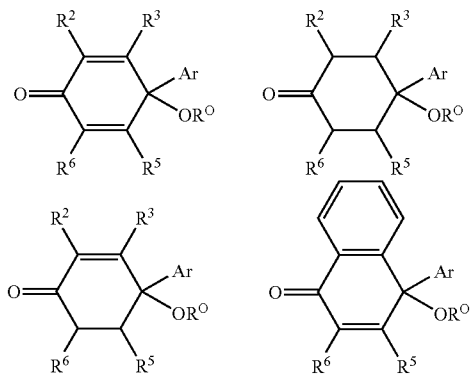

wherein:
Ar is a group of the following formula:

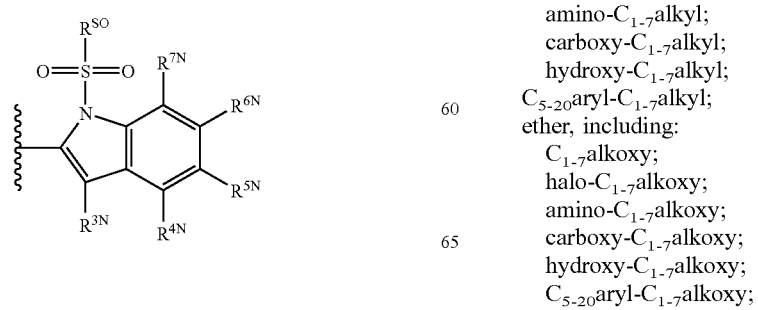

wherein:
$R^{SO}$ is independently $C_{1-7}$alkyl, $C_{3-20}$heterocyclyl, or $C_{5-20}$aryl; and is optionally substituted; and
each of $R^{3N}$, $R^{4N}$, $R^{5N}$, $R^{6N}$, and $R^{7N}$ is independently —H, or a group independently selected from:
hydroxy (—OH);
halo;
cyano (—CN);
carboxy (—COOH);
azido;
ester;
amino, including:
    amino-$C_{1-7}$alkyl-amino;
$C_{1-7}$alkyl, including:
    halo-$C_{1-7}$alkyl;
    amino-$C_{1-7}$alkyl;
    carboxy-$C_{1-7}$alkyl;
    hydroxy-$C_{1-7}$alkyl;
    $C_{5-20}$aryl-$C_{1-7}$alkyl;
ether, including:
    $C_{1-7}$alkoxy;
    halo-$C_{1-7}$alkoxy;
    amino-$C_{1-7}$alkoxy;
    carboxy-$C_{1-7}$alkoxy;
    hydroxy-$C_{1-7}$alkoxy;
    $C_{5-20}$aryl-$C_{1-7}$alkoxy;
acyl, including:
    $C_{1-7}$alkyl-acyl;
    halo-$C_{1-7}$alkyl-acyl;
    amino-$C_{1-7}$alkyl-acyl;
    carboxy-$C_{1-7}$alkyl-acyl;
    hydroxy-$C_{1-7}$alkyl-acyl;
$C_{5-20}$aryl-$C_{1-7}$alkyl-acyl;
$C_{5-20}$aryl-acyl; and
$C_{5-20}$aryl;
the group —$OR^O$ is independently:
    (a) —OH; or:
    (b) an ether group; or:
    (c) an acyloxy group;
each of $R^2$, $R^3$, $R^5$, and $R^6$, is independently:
    (a) H; or:
    (b) a monovalent monodentate substituent;
wherein each monovalent monodentate substituent, if present, is selected from:
hydroxy (—OH);
halo;
cyano (—CN);
carboxy (—COOH);
azido;
ester;
amino, including:
    $C_{1-7}$alkyl-amino;
    amino-$C_{1-7}$alkyl-amino;
$C_{1-7}$alkyl, including:
    halo-$C_{1-7}$alkyl;
    amino-$C_{1-7}$alkyl;
    carboxy-$C_{1-7}$alkyl;
    hydroxy-$C_{1-7}$alkyl;
$C_{5-20}$aryl-$C_{1-7}$alkyl;
ether, including:
    $C_{1-7}$alkoxy;
    halo-$C_{1-7}$alkoxy;
    amino-$C_{1-7}$alkoxy;
    carboxy-$C_{1-7}$alkoxy;
    hydroxy-$C_{1-7}$alkoxy;
    $C_{5-20}$aryl-$C_{1-7}$alkoxy;

acyl, including:
- $C_{1-7}$alkyl-acyl;
- halo-$C_{1-7}$alkyl-acyl;
- amino-$C_{1-7}$alkyl-acyl;
- carboxy-$C_{1-7}$alkyl-acyl;
- hydroxy-$C_{1-7}$alkyl-acyl;
- $C_{5-20}$aryl-$C_{1-7}$alkyl-acyl;
- $C_{5-20}$aryl-acyl;
- $C_{5-20}$aryl;
- thiol (—SH); and,
- thioether.

2. A compound according to claim 1, wherein each monovalent monodentate substituent, if present, is selected from: hydroxy, halo, $C_{1-7}$alkoxy, thiol, and thioether.

3. A compound according to claim 1, wherein each of $R^{3N}$, $R^{4N}$, $R^{5N}$, $R^{6N}$, and $R^{7N}$ is independently —H or is selected from: hydroxyl, halo, $C_{1-7}$alkyl, and $C_{1-7}$alkoxy.

4. A compound according to claim 2, wherein each of $R^{3N}$, $R^{4N}$, $R^{5N}$, $R^{6N}$, and $R^{7N}$ is independently —H or is selected from: hydroxyl, halo, $C_{1-7}$alkyl, and $C_{1-7}$alkoxy.

5. A compound according to claim 4, selected from compounds of the following formula and pharmaceutically acceptable salts, esters, amides, solvates, and hydrates thereof:

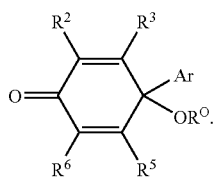

6. A compound according to claim 4, selected from compounds of the following formula and pharmaceutically acceptable salts, esters, amides, solvates, and hydrates thereof:

7. A compound according to claim 4, selected from compounds of the following formula and pharmaceutically acceptable salts, esters, amides, solvates, and hydrates thereof:

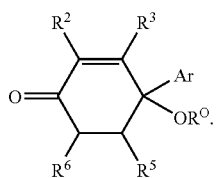

8. A compound according to claim 4, selected from compounds of the following formula and pharmaceutically acceptable salts, esters, amides, solvates, and hydrates thereof:

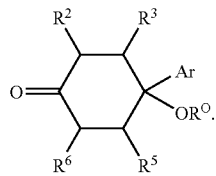

9. A compound according to claim 8, wherein each monovalent monodentate substituent, if present, is selected from: halo, thiol, and thioether.

10. A compound according to claim 4, selected from compounds of the following formula and pharmaceutically acceptable salts, esters, amides, solvates, and hydrates thereof:

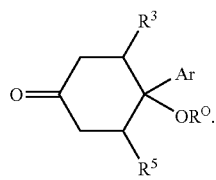

11. A compound according to claim 10, wherein each monovalent monodentate substituent, if present, is selected from: halo, thiol, and thioether.

12. A compound according to claim 10, wherein one or both of $R^3$ and $R^5$ is a thiol or a thioether group.

13. A compound according to claim 10, wherein each of $R^3$ and $R^5$ is a thiol or a thioether group.

14. A compound according to claim 4, wherein $R^{SO}$ is phenyl or naphthyl, and is optionally substituted.

15. A compound according to claim 5, wherein $R^{SO}$ is phenyl or naphthyl, and is optionally substituted.

16. A compound according to claim 6, wherein $R^{SO}$ is phenyl or naphthyl, and is optionally substituted.

17. A compound according to claim 7, wherein $R^{SO}$ is phenyl or naphthyl, and is optionally substituted.

18. A compound according to claim 8, wherein $R^{SO}$ is phenyl or naphthyl, and is optionally substituted.

19. A compound according to claim 10, wherein $R^{SO}$ is phenyl or naphthyl, and is optionally substituted.

20. A compound according to claim 13, wherein $R^{SO}$ is phenyl or naphthyl, and is optionally substituted.

21. A compound according to claim 4, wherein wherein $R^O$ is —H.

22. A compound according to claim 5, wherein wherein $R^O$ is —H.

23. A compound according to claim 6, wherein wherein $R^O$ is —H.

24. A compound according to claim 8, wherein wherein $R^O$ is —H.

25. A compound according to claim 10, wherein wherein $R^O$ is —H.

26. A compound according to claim 13, wherein wherein $R^O$ is —H.

27. A compound according to claim 14, wherein wherein $R^O$ is —H.

28. A compound according to claim 15, wherein wherein $R^O$ is —H.

29. A compound according to claim 16, wherein wherein $R^O$ is —H.

30. A compound according to claim 17, wherein wherein $R^O$ is —H.

31. A compound according to claim 18, wherein wherein $R^O$ is —H.

32. A compound according to claim 19, wherein wherein $R^O$ is —H.

33. A compound according to claim 20, wherein wherein $R^O$ is —H.

34. A compound selected from compounds of the following formulae and pharmaceutically acceptable salts, esters, solvates, and hydrates thereof:

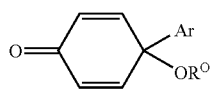

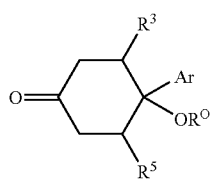

wherein:
Ar is a group of the following formula:

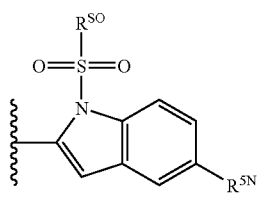

and wherein:
each of $R^3$ and $R^5$, if present, is independently a thiol or thioether group;
$R^O$ is independently —H;
$R^{SO}$ is independently phenyl, and is optionally substituted; and
$R^{5N}$ is independently —H, —OH, —F, —Cl, —Br, —I, -Me, -Et, —OMe, or —OEt.

35. A compound selected from the following compounds and pharmaceutically acceptable salts, esters, amides, solvates, hydrates, and protected forms thereof:

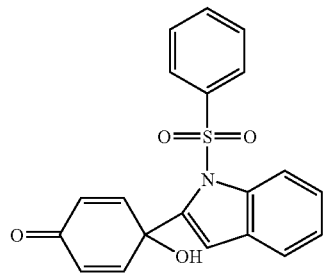

-continued

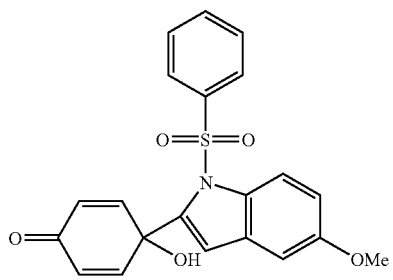

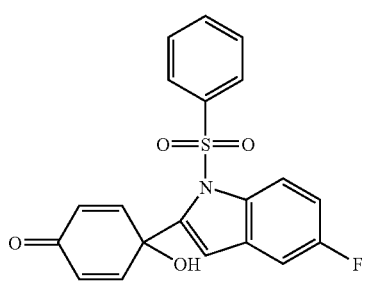

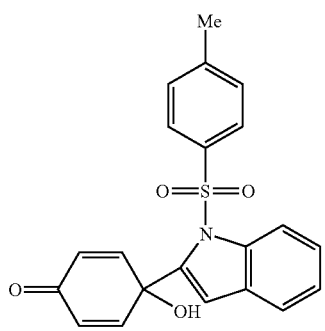

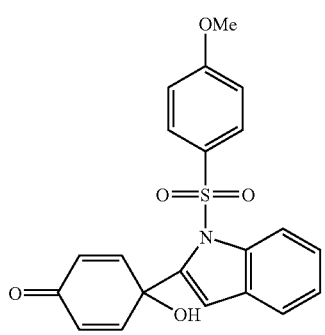

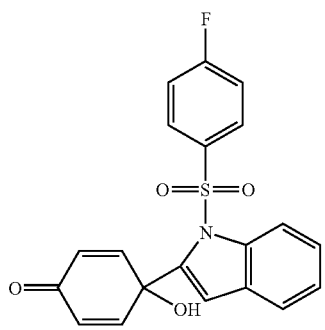

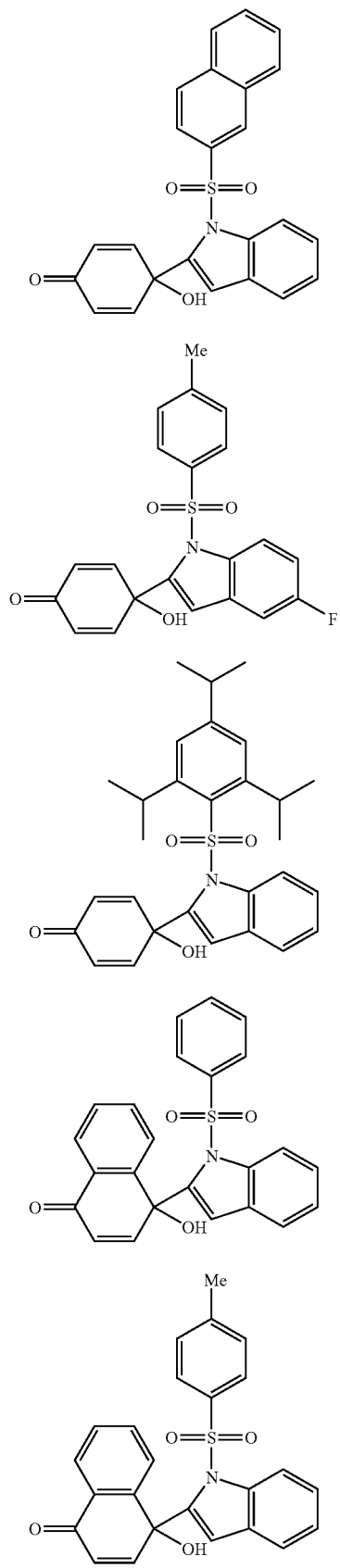
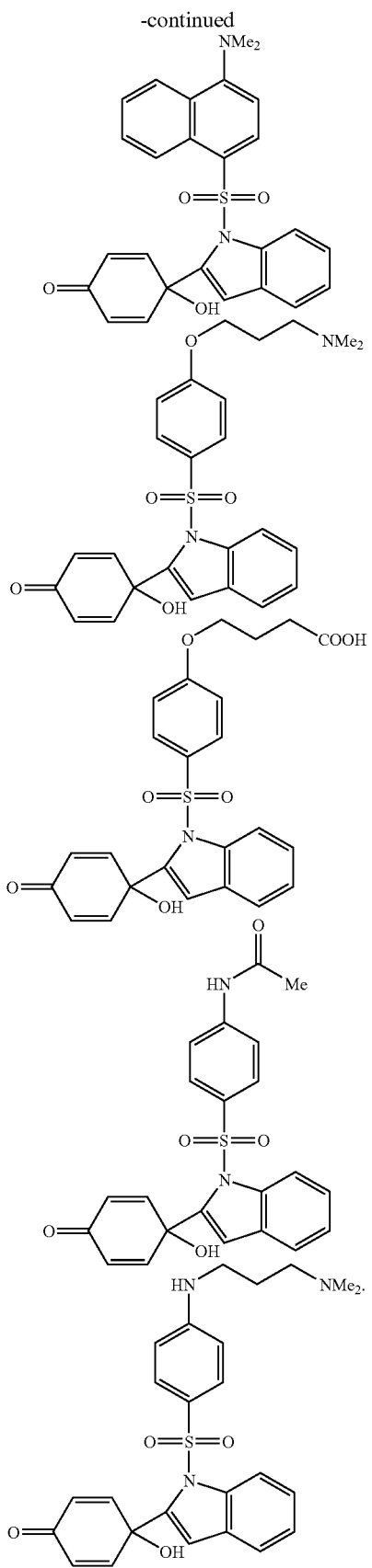

36. A compound selected from the following compound and pharmaceutically acceptable salts, esters, solvates, and hydrates thereof:

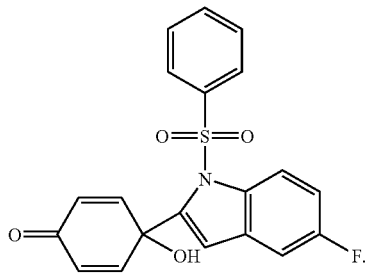

37. A composition comprising a compound according to claim 1 and a pharmaceutically acceptable carrier or diluent.

38. A method of treatment of colon cancer comprising administering to a subject suffering from said cancer a therapeutically-effective amount of a compound according to claim 1.

39. A method of treatment of renal cancer comprising administering to a subject suffering from said cancer a therapeutically-effective amount of a compound according to claim 1.

40. A method of treatment of breast cancer comprising administering to a subject suffering from said cancer a therapeutically-effective amount of a compound according to claim 1.

41. A method of treatment of CNS cancer comprising administering to a subject suffering from said cancer a therapeutically-effective amount of a compound according to claim 1.

42. A method of treatment of melanoma comprising administering to a subject suffering from said cancer a therapeutically-effective amount of a compound according to claim 1.

43. A method of treatment of colon cancer comprising administering to a subject suffering from said cancer a therapeutically-effective amount of a compound according to claim 34.

44. A method of treatment of renal cancer comprising administering to a subject suffering from said cancer a therapeutically-effective amount of a compound according to claim 34.

45. A method of treatment of breast cancer comprising administering to a subject suffering from said cancer a therapeutically-effective amount of a compound according to claim 34.

46. A method of treatment of CNS cancer comprising administering to a subject suffering from said cancer a therapeutically-effective amount of a compound according to claim 34.

47. A method of treatment of melanoma comprising administering to a subject suffering from said cancer a therapeutically-effective amount of a compound according to claim 34.

48. A method of treatment of colon cancer comprising administering to a subject suffering from said cancer a therapeutically-effective amount of a compound according to claim 36.

49. A method of treatment of renal cancer comprising administering to a subject suffering from said cancer a therapeutically-effective amount of a compound according to claim 36.

50. A method of treatment of breast cancer comprising administering to a subject suffering from said cancer a therapeutically-effective amount of a compound according to claim 36.

51. A method of treatment of CNS cancer comprising administering to a subject suffering from said cancer a therapeutically-effective amount of a compound according to claim 36.

52. A method of treatment of melanoma comprising administering to a subject suffering from said cancer a therapeutically-effective amount of a compound according to claim 36.

* * * * *